(12) United States Patent
Kudithipudi et al.

(10) Patent No.: US 12,319,923 B2
(45) Date of Patent: Jun. 3, 2025

(54) INCREASING TRICHOME DENSITY AND IMPROVING TRANSPORT OF METABOLITES IN PLANT TRICHOMES

(71) Applicants: ALTRIA CLIENT SERVICES LLC, Richmond, VA (US); UNIVERSITY OF VIRGINIA PATENT FOUNDATION, Charlottesville, VA (US)

(72) Inventors: Chengalrayan Kudithipudi, Midlothian, VA (US); Yanxin Shen, Henrico, VA (US); Dongmei Xu, Glen Allen, VA (US); Michael Paul Timko, Charlottesville, VA (US); Roel Rabara, Charlottesville, VA (US)

(73) Assignees: Altria Client Services LLC, Richmond, VA (US); University Of Virginia Patent Foundation, Charlottesville, VA (US)

( * ) Notice: Subject to any disclaimer, the term of this patent is extended or adjusted under 35 U.S.C. 154(b) by 85 days.

(21) Appl. No.: 17/591,057

(22) Filed: Feb. 2, 2022

(65) Prior Publication Data

US 2022/0243216 A1 Aug. 4, 2022

Related U.S. Application Data

(60) Provisional application No. 63/145,263, filed on Feb. 3, 2021, provisional application No. 63/145,262, filed on Feb. 3, 2021, provisional application No. 63/145,259, filed on Feb. 3, 2021.

(51) Int. Cl.
*C12N 15/82* (2006.01)
*C07K 14/41* (2006.01)
*C07K 14/415* (2006.01)
*C12P 5/00* (2006.01)

(52) U.S. Cl.
CPC ........ *C12N 15/8262* (2013.01); *C07K 14/415* (2013.01); *C12N 15/8223* (2013.01); *C12N 15/8243* (2013.01); *C12P 5/007* (2013.01); *C12N 2800/22* (2013.01)

(58) Field of Classification Search
CPC .................. C12N 15/8262; C12N 15/8243
See application file for complete search history.

(56) References Cited

U.S. PATENT DOCUMENTS

| | | |
|---|---|---|
| 4,516,590 A | 5/1985 | Teng |
| 4,528,993 A | 7/1985 | Sensabaugh, Jr. et al. |
| 4,660,577 A | 4/1987 | Sensabaugh et al. |
| 4,848,373 A | 7/1989 | Lenkey |
| 4,897,355 A | 1/1990 | Eppstein et al. |
| 4,946,787 A | 8/1990 | Eppstein et al. |
| 4,987,907 A | 1/1991 | Townend |
| 5,049,386 A | 5/1991 | Eppstein et al. |
| 5,159,135 A | 10/1992 | Umbeck |
| 5,188,958 A | 2/1993 | Moloney et al. |
| 5,372,149 A | 12/1994 | Roth et al. |
| 5,463,174 A | 10/1995 | Moloney et al. |
| 5,538,880 A | 7/1996 | Lundquist et al. |
| 5,550,318 A | 8/1996 | Adams et al. |
| 5,591,616 A | 1/1997 | Hiei et al. |
| 5,750,871 A | 5/1998 | Moloney et al. |
| 5,824,877 A | 10/1998 | Hinchee et al. |
| 6,153,812 A | 11/2000 | Fry et al. |
| 6,160,208 A | 12/2000 | Lundquist et al. |
| 6,194,636 B1 | 2/2001 | McElroy et al. |
| 6,232,526 B1 | 5/2001 | McElroy et al. |
| 6,384,301 B1 | 5/2002 | Martinell et al. |
| 6,399,861 B1 | 6/2002 | Anderson et al. |
| 9,115,366 B2 | 8/2015 | Tissier et al. |
| 9,603,335 B2 | 3/2017 | Lewis et al. |
| 2004/0216189 A1 | 10/2004 | Houmard et al. |
| 2005/0178398 A1 | 8/2005 | Breslin et al. |
| 2006/0191548 A1 | 8/2006 | Strickland et al. |
| 2006/0200878 A1 | 9/2006 | Lutfiyya et al. |
| 2006/0260002 A1 | 11/2006 | Ronen et al. |
| 2007/0006341 A1 | 1/2007 | Wagner et al. |
| 2008/0281135 A1 | 11/2008 | Tissier et al. |
| 2021/0010018 A1 | 1/2021 | Kexuan et al. |
| 2022/0243214 A1 | 8/2022 | Kudithipudi et al. |
| 2022/0243215 A1 | 8/2022 | Kudithipudi et al. |
| 2024/0018536 A1 | 1/2024 | Kudithipudi et al. |

FOREIGN PATENT DOCUMENTS

| | | |
|---|---|---|
| CN | 104 152 463 A | 11/2014 |
| CN | 108070594 A | 5/2018 |
| FR | 2 903 703 A1 | 1/2008 |

(Continued)

OTHER PUBLICATIONS

Guo et al., 2004, Protein tolerance to random amino acid change. Proceedings of the National Academy of Sciences, 101(25), 9205-9210. (Year: 2004).*

Yang et al., 2022, Genome-wide identification and expression analysis of the R2R3-MYB gene family in tobacco (*Nicotiana tabacum* L.); BMC genomics, 23(1), 432. (Year: 2022).*

Huchelmann et al., 2017, Plant glandular trichomes: natural cell factories of high biotechnological interest. Plant physiology, 175(1), 6-22. (Year: 2017).*

Wang et al., 2021, Analysis and review of trichomes in plants. BMC plant biology, 21(1), 1-11. (Year: 2021).*

Payne et al., 1999, Heterologous myb genes distinct from GL1 enhance trichome production when overexpressed in Nicotiana tabacum. Development, 126(4), 671-682. (Year: 1999).*

(Continued)

*Primary Examiner* — Cathy Kingdon
*Assistant Examiner* — Santosh Sharma
(74) *Attorney, Agent, or Firm* — Arnold & Porter Kaye Scholer LLP

(57) ABSTRACT

The present disclosure relates to compositions and methods related to modification of trichome density and transport of metabolite and their uses in plants, including tobacco and *cannabis*. The provided transcription factors enable the increase in trichome density in plants.

17 Claims, 21 Drawing Sheets

Specification includes a Sequence Listing.

(56) References Cited

FOREIGN PATENT DOCUMENTS

| WO | WO 91/16024 | 10/1991 |
|---|---|---|
| WO | WO 91/17424 | 11/1991 |
| WO | WO 2004/041006 A1 | 5/2004 |
| WO | WO 2010/111571 A1 | 9/2010 |
| WO | WO 2017/181018 A1 | 10/2017 |
| WO | WO 2018/057385 A2 | 3/2018 |
| WO | WO 2018/176055 A2 | 9/2018 |
| WO | WO 2019/147873 A2 | 8/2019 |
| WO | WO 2020/185865 A1 | 9/2020 |
| WO | WO 2021/003180 A1 | 1/2021 |

OTHER PUBLICATIONS

Hernandez et al., 2017, Aa MYB 1 and its orthologue At MYB 61 affect terpene metabolism and trichome development in Artemisia annua and *Arabidopsis thaliana*. The Plant Journal, 90(3), 520-534. (Year: 2017).*

Liu et al., 2018, NbGIS regulates glandular trichome initiation through GA signaling in tobacco. Plant Molecular Biology, 98, 153-167 . (Year: 2018).*

Sierro et al., 2014, The tobacco genome sequence and its comparison with those of tomato and potato. Nature communications, 5(1), 3833. (Year: 2014).*

Predicted: transcription factor MYB86-like [Nicotiana tabacum]. NCBI Reference Sequence: XP_016450602.1. linear PLN May 3, 2016. (Year: 2016).*

Hernandez et al., 2017, Aa MYB 1 and its orthologue At MYB 61 affect terpene metabolism and trichome development in Artemisia annua and *Arabidopsis thaliana*, Supplementary Data. The Plant Journal, 90(3), 520-534. (Year: 2017).*

Tian et al., 2018, Overexpression of BraLTP2, a lipid transfer protein of *Brassica napus*, results in increased trichome density and altered concentration of secondary metabolites. International journal of molecular sciences, 19(6), 1733. (Year: 2018).*

Lipid transfer protein [Nicotiana tabacum]. 2011. NCBI protein GenBank: BAK19150.1 (Year: 2011).*

Aharoni et al., "Volitale science? Metabolic engineering of terpenoids in plants," Trends in Plant Science, vol. 10, No. 12, pp. 594-602 (Dec. 2005) (Oxford, UK) Available online: https://doi.org/10.1016/j.tplants.2005.10.005.

Altschul et al. "Basic local alignment search tool." *J. Mol. Biol.* 215, pp. 403-410 (Oct. 1990) (Oxford, United Kingdom). Available online: https://doi.org/10.1016/S0022-2836(05)80360-2.

Altschil et al., "Gapped BLAST and PSI-BLAST: a new general of protein database search programs," *Nucleic Acids Res.*, vol. 25, Issue 17, pp. 3389-3402 (Sep. 1997) (Oxford, United Kingdom). Available online: https://doi.org/10.1093/nar/25.17.3389.

Amaducci et al., "Influence of agronomic factors on yield and quality of hemp (*Cannabis sativa* L.) fibre and implication for an innovative production system," *Field Crops Research*, 107, pp. 161-169 (May 2008) (Oxford, United Kingdom). Available online: DOI:10.1016/j.fcr.2008.02.002.

Brückner et al., "High-level diterpene production by transient expression in *Nicotiana benthamiana.*" *Plant Methods*. 9(1): 46, 10 pages, (Dec. 2013). Available online: doi: https://doi.org/10.1186/1746-4811-9-46.

Chaplin et al. "The Use of Male-Sterile Tobacco in Relation to Topping and Suckering Practices" *Tobacco Science* 7(35), pp. 158-162, (1963). Available online: https://www.coresta.org/sites/default/files/abstracts/Tobacco_Science_1963_7-35_p._158-162_ISSN.0082-4623.pdf.

Chapters 4B and 4C of Tobacco, Production, Chemistry and Technology, Davis & Nielsen, eds., Blackwell Publishing, pp. 70-103, (1999) (Oxford, UK).

Feeney et al., Tissue Culture and *Agrobacterium*-mediated Transformation of Hemp (*Canniabis sativa*L.), *In Vitro Cell. and Dev. Biol.—Plant*, 39, pp. 578-585 (Nov./Dec. 2003) (Baden-Wuerttemberg, Germany). Available online: DOI:10.1079/IVP2003454.

GenBankAccession MG493458.1, dated Oct. 2, 2018.

Gen Bank Accession No. GQ911584.1, dated Mar. 10, 2010.

GenBank Accession No. KU162868.1, dated May 8, 2017.

Griffiths-Jones et al., "Rfam: an RNA family database," *Nucleic Acids Res.*, 31(1), pp. 439-441 (Jan. 2003) (Oxford, United Kingdom). Available online: https://doi.org/10.1093/nar/gkg006.

International Search Report and Written Opinion issued in International Patent Application No. PCT/US2022/014895 dated Jul. 21, 2022.

International Search Report and Written Opinion issued in International Patent Application No. PCT/US2022/014896 dated Jul. 4, 2022.

Jiang et al., "Extraction and Analysis of Terpenes/Terpenoids," *Curr Protoc Plant Biol.*, 1(2), pp. 345-358 (Jun. 2016) (Hoboken, New Jersey). Available online: https://doi.org/10.1002/cppb.20024.

Katoh et al., "Specific residues at every third position of siRNA shape its efficient RNAi activity," *Nucleic Acids Res.*, 35(4), pp. e27 (Feb. 2007) (Oxford, UK). Available online: https://doi.org/10.1093/nar/gk11120.

Khvorova et al., "Functional siRNAs and miRNAs Exhibit Strand Bias," *Cell*, vol. 115, Issue 2, pp. 209-216 (Oct. 2003) (Cambridge, MA). Available online: DOI:https://doi.org/10.1016/S0092-8674(03)00801-8

Kim, "MicroRNA Biogenesis: Coordinated Cropping and Dicing," *Nature Rev. Mol. Cell. Biol.*, 6, pp. 376-385 (May 2005) (Baden-Wuerttemberg, Germany). Available online: https://doi.org/10.1038/nrm1644.

Lange et al., "Metabolic engineering of plant monoterpenes, sesquiterpenes and diterpenes—current status and future opportunities," *Plant Biotechnology Journal* 11(2), 169-196 (Feb. 2013) (Oxford, UK). First published online Nov. 2012: https://doi.org/10.1111/pbi.12022.

Laterre et al., "Photosynthetic Trichomes Contain a Specific Rubisco with a Modified pH-Dependent Activity," *Plant Physiology* 173(4), pp. 2110-2120 (Apr. 2017) (Rockville, MD). Available online: DOI: 10.1104/pp.17.00062.

Lee et al., "Increased sesqui- and triterpene production by co-expression of HMG-CoA reductase and biotin carboxyl carrier protein in tobacco (*Nicotiana benthamiana*)," *Metabolic Engineering* 52, pp. 20-28 (Mar. 2019) (Oxford, UK). Available online: DOI:10.1016/j.ymben.2018.10.008.

Livak et al., "Analysis of Relative Gene Expression Data Using Real-Time Quanitative PCR and the $2^{-\Delta\Delta C_T}$ Method," *Methods*, vol. 25, Issue 4, pp. 402-408 (Dec. 2001) (Oxford, United Kingdom). Available online: doi: 10.1006/meth.2001.1262.

Lücker et al., "Metabolic Engineering of monoterpene biosynthesis: two-step production of (+)-trans-isopiperitenol by tobacco," *The Plant Journal* 39(1), pp. 135-145 (Jul. 2004) (online publication). Available online: https://doi.org/10.1111/j.1365-313X.2004.02113.x.

Mizusaki et al., "changes in the activities of ornithine decarboxylase, putrescine N-methyltransferase and N-methylputrescine oxidase in tobacco roots in relation to nicotine biosynthesis," Plant and Cell Physiology, 14(1), pp. 103-110 (Feb. 1973) (Oxford, United Kingdom). Available online: https://doi.org/10.1093/oxfordjournals.pcp.a074831.

Ohara et al., "Limonene production in tobacco wih Perilla limonene synthase cDNA," *Journal of Experimental Botany*, 54(393), pp. 2635-2642 (Dec. 2003) (Oxford, UK); Available online: DOI: 10.1093/jXb/erg300.

Fan et al. "Bioinformatics study of 1-deoxy-$_D$-xylulose-5-phosphate synthase (DXS) genes in Solanaceae" *Mol. Bio. Reports* 46:5175-5184) (Jul. 2019). Available online: https://doi.org/10.1007/s11033-019-04975-5.

PlantCare Online Database, Planet: A Network of European Plant Databases, accessed and printed August 4, 2023; Available online: https://bioinforrnatics.psb.ugent.be/webtools/plantcare/html/.

PlantPan 3.0 Online Database: The Plant Promoter Analysis Navigator accessed and printed Aug. 4, 2023. Available online: http://plantpan.itps.ncku.edu.tw/plantpan3/index.htrnl.

(56) References Cited

OTHER PUBLICATIONS

Pottier et al. "Identification of two new trichome-specific promoters of *Nicotiana tabacum,*" *Planta* 251(3), pp. 58, (Feb. 2020) (electronic publication). Available online: https://doi.org/10.1007/s00425-020-03347-9.

Ramsey, "Why Farmers Prefer Feminized Seeds," *Kush.com Online Blog*, accessed and printed online Aug. 4, 2023, https://kush.com/blog/feminized-cannabis-seeds-all-you-need-to-know/.

Reynolds et al., "Rational siRNA design for RNA interference," *Nature Biotechnol.*, 22:326-330 (Feb. 2004) (Baden-Wuerttemberg, Germany). Available online: DOI: 10.1038/nbt936.

Sabzehzari et al., "Photy-miRNAs-based regulation of metabolites biosynthesis in medicinal plants," *Gene* vol. 682, pp. 13-24 (Jan. 2019) (Oxford, UK). Available online: https://doi.org/10.1016/j.gene.2018.09.049.

Seely et al., "Changes in Mouse Kidney Ornithine Decarboxylase Activity Are Brought About by Changes in the Amount of Enzyme Protein as Measured by Radioimmunoassay," *J. Biol. Chem.*, vol. 258, No. 4, pp. 2496-2500 (Feb. 1983) (Oxford, United Kingdom). Available online: https://doi.org/10.1016/80021-9258(18)32953-3.

Sikora et al., "Infuence of Agroclimatic Conditions on Content of Main Cannabinoids in Industrial Hemp (*Cannabis sativa* L.)," *Genetika*, 43 (3), pp. 449-456 (Jan. 2011) (electronic publication). Available online: DOI: https://doi.org/10.2298/GENSR11034498.

Sui et al., "Formation of α- and β-Cembrattiene-Diols in Tobacco (*Nicotiana tabacum* L.) Is Regulated by Jasmonate-Signaling Components via Manipulating Multiple Cembranoid Synthetic Genes" *Molecules* 23(2511):1-14 (Sep. 2018). Available online: https://doi.org/10.3390/molecules23102511.

Tissier et al., "Chapter 18: Tobacco Trichomes as a PlatforIn for Terpenoid Biosynthesis Engineering," *Isoprenoid Synthesis in Plants and Microorganisms New Concepts and Experimental Approaches*, pp. 271-283 (Aug. 2012) (Baden-Wuerttemberg, Germany). Available online: DOI:10.1007/978-1-4614-4063-5_18.

Tissier, "17: Trichme Specific Expression: Promoters and Their Applications," *Transgenic Plants—Advances and Limitation*, pp. 353-378 with cover page (Mar. 2012) (Electronic Publication). Available online: http://www.intechopen.com/books/transgenic-plants-advances-and-limitations/trichome-specific-expressionpromoters-and-their-applications.

Uni ProtKB Accession No. D3W9H9_ TOBAC (version 40 dated Dec. 2, 2020) (Year: 2020).

Wang et al., "Metabolic engineering of terpene biosynthesis in plants using a trichome-specific transcription factor MsYABBY5 from Spearmint (*Mentha spicata*)," *Plant Biotechnology Journal* vol. 14, Issue 7, pp. 1619-1632 (Feb. 2016) (Oxford, UK). Available online: https://doi.org/10.1111/pbi.12525.

Yan et al. "A Review on Bioactivities of Tobacco Cembranoid Diterpenes," *Biomolecules* 9(30), pp. 1-9 (Jan. 2019). Available online: https://doi.org/10.3390/biom9010030.

Yang et al., "Determination of cannabinoids in biological samples using a new solid phase micro-extraction membrane and liquid chromatography-mass spectrometry," *Forensic Science International*, 162(1-3), pp. 135-139 (Oct. 2006) (Oxford, UK). Available online: https://doi.org/10.1016/j.forsciint.2006.03.036.

Yu et al., "A high-throughput colorimettic assay to measure the activity of glutamate decarboxylase," *Enzyme and Microbial Technology* 49(3), pp. 272-276 (Aug. 2011) (Oxford, United Kingdom). Available online: https://doi.org/10.1016/j.enzmictec.2011.06.007.

Zeng et al., "Both Natural and Designed Micro RNAs Can Inhibit the Expression of Cognate mRNAs When Expressed in Human Cells," *Mol. Cell*, 9(6), pp. 1327-1333 (Jun. 2002) (Cambridge, Massachusetts). Available online: https://www.cell.com/molecular-cell/pdf/S1097-2765(02)00541-5.pdf.

Altschul et al. "Basic local alignment search tool." *J. Mol. Biol.* 215:403-410 (1990)

Canevascini et al., "Tissue-Specific Expression and Promoter Analysis of the Tobacco Itp1 Gene1," *Plant Physiol* 112(2) 513-524 (1996).

Chalvin et al., "Genetic Control of Glandular Trichome Development," *Trends in Plant Science* 25(5):477-487 (2020).

Chandra et al., "Comparative transcriptome analysis to identify putative genes related to trichome development in *Ocimum* Species," *Molecular Biology Reports*, 47:6587-6598 (2020).

Chenna et al., "Multiple sequence alignment with the Clustal series of programs," *Nucleic Acids Research* 31: 3497-3 500 (2003).

Choi et al., "Tobacco NtLTP1, a glandular-specific lipid transfer protein, is required for lipid secretion from glandular trichomes," *Plant Journal*, 70:480-491 (2012).

Database NCBI Accession No. XP_030504371 dated May 18, 2020.

Database UniProtKB Accession No. A0A1S3YF18 dated Apr. 12, 2017.

Goldman et al., "Female sterile tobacco plants are produced by stigma-specific cell ablation," *EMBO Journal* 13:2976-2984 (1994).

Horsch et al., "A Simple and General Method for Transferring Genes into Plants," *Science*, 227:1229-1231 (1985).

Huchelmann et al., "Plant Glandular Trichomes: Natural Cell Factories of High Biotechnological Interest," *Plant Physiology* 175:6-22 (2017).

International Search Report and Written Opinion dated Jul. 8, 2022 in Int'Appln PCT/US2022/014898.

Larkin Ma et al., "Clustal W and Clustal X version 2.0," *Bioinformatics* 23: 2947-48 (2007).

Lim et al., "Petal-specific activity of the promoter of an anthocyanidin synthase gee of tobacco (*Nicotiana tabacum* L.)," *Plant Cell Tissue Organ Cult* 114(3):373-383 (2013).

Liu et al., "NbGIS regulates glandular trichome initiation through GA signaling in tobacco," *Plant Molecular Biology*, 98:153-167 (2018).

Matias-Hemandez et al., "AaMYB1 and its orthologue AtMYB61 affect terpene metabolism and trichome development in *Artemisia annua* and *Arabidopsis thaliana,*" *The Plant Journal* 90:520-534 (2017).

Mayo et al., "Genetic Transformation of tobacco NT1 cells with *Agrobacterium tumefaciens,*" *Nat. Protoc.*, 1:1105-1111 (2006).

Nautiyal et al., "Comprehensive trancriptome analysis provides insights into metabolic and gene regulatory networks in trichomes of *Nicotiana tabacum,*" *Plant Molecular Biology* 102:625-644 (2020).

Salminen et al., "Lipid transfer proteins: classification, nomenclature, structure, and function," *Planta*, 244(5), pp. 971-997 (Nov. 2016) (Baden-Wuerttemberg, Germany).

Thompson et al., "Clustal W: Improving the sensitivity of progressive multiple sequence alignment through sequence weighting, position-specific gap penalties and weight matrix choice," *Nucleic Acids Research* 22: 4673-4680 (1994).

Tissier et al., "Plant Volatiles: Going 'In' but not 'Out' of Trichome Cavities," *Trends in Plant Science*, 22(11), pp. 930-938 (Nov. 2017) (Cambridge, Massachusetts, US).

Tso (1999, Chapter 1 in Tobacco, Production, Chemistry and Technology, Davis & Nielsen, eds., Blackwell Publishing, Oxford).

Wernsman, E. A, and Rufty, R. C. 1987. Chapter Seventeen. Tobacco. pp. 669-698 In: Cultivar Development. Crop Species. W. H. Fehr (ed.), MacMillan Publishing Co., Inc., New York, N.Y. 761 pp.

Xu et al., "SIMYC1 Regulates Type VI Glandular Trichome Formation and Terpene Biosynthesis in Tomato Glandular Cells," *The Plant Cell* 30:2988-3005 (2018).

Zhang et al., "Characterization of NtREL1, a novel root-specific gene from tobacco, and upstream promoter activity analysis in homologous and heterologous hosts," *Plant Cell Rep* 35,757-769 (2016).

Christenhusz et al., "The number of known plant species in the world and its annual increase," *Phytotaxa*, 261(3), pp. 201-217, (May 2016) (electronic publication), http://dx.doi.org/10.11646/phytotaxa.261.3.1.

Galis et al., "A novel R2R3 MYB transcription factor NtMYBJS1 is a methyl jasmonate-dependent regulator of phenylpropanoid-conjugate biosynthesis in tobacco," *Plant J*, 46, pp. 573-592 (May 2006) (electronic publication), https://doi.org/10.1111/j.1365-313X.2006.02719.x.

(56) References Cited

OTHER PUBLICATIONS

Zhao et al., "Characterization of the Poplar R2R3-MYB Gene Family and Over-Expression of PsnMYB108 Confers Salt Tolerance in Transgenic Tobacco", *Frontiers in Plant Science*, 11:571881, 16 pages (Oct. 2020) (electronic publication), doi: 10.3389/fpls.2020.571881.

Bhatt, "Molecular Cloning, Expression and Insilco Analysis of Drought Stress Inducible MYB Transcription Factor Encoding Gene from C4 Plant Eleusine Coracana," *Research Square*, pp. 1-23, https://doi.org/10.21203/rs.3.rs-955905/v1 (Nov. 2021).

Ding et al., "A transcriptome-based association study of growth, wood quality, and oleoresin traits in a slash pine breeding population", *PLoS Genetics*, 18(2):e1010017, pp. 1-24 (Feb. 2, 2022).

Fu et al., "Transcriptomic analysis of flower opening response to relatively low temperatures in *Osmanthus fragrans*", *BMC Plant Biology*, 20(337), pp. 1-16, (Jul. 2020).

Gao et al., "Transcriptome analysis and identification of genes associated with floral transition and fruit development in rabbiteye blueberry (*Vaccinium ashei*)", *PLoS ONE*, 16(10):e0259119, pp. 1-18 (Oct. 2021).

Klepikova et al., "A high resolution map of the *Arabidopsis thaliana* developmental transcriptome based on RNA-seq profiling," *Plant Journal*, 88(6), pp. 1058-1070 (Nov. 2016).

Li et al., "Integrated analysis of high-throughput sequencing data shows abscisic acid-responsive genes and miRNAs in strawberry receptacle fruit ripening," *Horticulture Research*, 6(26), pp. 1-13 (Feb. 2019).

Ortiz et al., "The Endophytic Fungus *Chaetomium cupreum* Regulates Expression of Genes Involved in the Tolerance to Metals and Plant Growth Promotion in *Eucalyptus globulus* Roots," *Microorganisms*, 7(490), pp. 1-15 (Oct. 2019).

Sallaud et al., "Characterization of two genes for the biosynthesis of the labdane diterpene Z-abienol in tobacco (*Nicotania tabacum*) gladular trichomes," *Plant Journal*, 72, pp. 1-17 (Jul. 2012).

Schilmiller et al., "Harnessing plant trichome biochemistry for the production of useful compounds," *The Plant Journal*, 54, pp. 702-711, (May 2008).

Wessels et al., "An AP2/ERF transcription factor ERF139 coordinates xylem cell expansion and secondary cell wall deposition," *New Phytologist*, 224, pp. 1585-1599 (May 2019).

Zerbe et al., "Bifunctional cis-Abienol Synthase from Abies balsamea Discovered by Transcriptome Sequence and Its Implications for Diterpenoid Fragrance Production," *The Journal of Biological Chemistry*, 287(15), pp. 12121-12131 (Apr. 2012).

Zerbe et al., "Plant diterpene synthases: exploring modularity and metabolic diversity for bioengineering," *Trends in Biotechnology*, 33(7), pp. 419-429 (Jul. 2015).

Zhang et al., "Transcript Quantification by RNA-Seq Reveals Differentially Expressed Genes in the Red and Yellow Fruits of *Fragaria vesca*," *PLoS ONE*, 10(12):e0144356, pp. 1-15 (Dec. 2015).

\* cited by examiner

N. tabacum 'Izmir Ego'

N. tabacum 'TN90'

N. benthamiana

INCREASING TRICHOME DENSITY AND IMPROVING TRANSPORT OF METABOLITES IN PLANT TRICHOMES

CROSS-REFERENCE TO RELATED APPLICATIONS AND INCORPORATION OF SEQUENCE LISTING

This application claims the benefit of U.S. Provisional Patent Application No. 63/145,259, filed Feb. 3, 2021; U.S. Provisional Patent Application No. 63/145,262, filed Feb. 3, 2021; and U.S. Provisional Patent Application No. 63/145,263, filed Feb. 3, 2021, all of which are incorporated by reference herein in their entireties. This application also contains a Sequence Listing, which has been submitted electronically in ASCII format and is hereby incorporated by reference in its entirety. Said ASCII copy, created on Jan. 25, 2022, is named P335029WO00_SL.txt and is 141,791 bytes in size as measured in Microsoft Windows®.

FIELD

The present disclosure relates to enhancing trichome initiation and development on the surface of plant tissues as well as improving the transport of specialized metabolites into trichomes, the exudation of specialized metabolites from trichomes, and the application of such to change the chemical composition in plants, including tobacco.

BACKGROUND

Glandular trichomes are epidermal outgrowths in plants that are the site of metabolic compound synthesis and storage. Their presence on stem, leaf, and floral tissues provides protection for plants against various biotic and abiotic stresses. Glandular trichomes also play a role in the biosynthesis, storage, and secretion of specialized or secondary metabolites.

Metabolites produced and secreted by glandular trichomes are often hydrophobic (e.g., fatty acid derivatives, flavonoids, terpenoids). Terpenoids constitute the largest and most diverse class of plant metabolites. The olefinic backbone of terpenoids is made of multiples of the five-carbon (C) isoprene unit, with the major groups being monoterpenes (10C), sesquiterpenes (15C), and diterpenes (20C). These terpenoids are produced through the condensation of five-carbon isoprene units (dimethylallyl diphosphate [DMAPP] and isopentenyl diphosphate [IPP]) most often by the sequential head-to-tail addition of DMAPP to IPP.

The amount of secondary metabolites produced is often tightly correlated to the glandular trichome density present on the plant epidermis (Chalvin et al., Cell, 25:477-487 (2020)). One way to increase the amount of secondary metabolite production in plants is to increase the density of trichomes present on the plant epidermis. Transcriptional regulation of trichome initiation has been shown to involve members of MYB and C2H2 zinc-finger family of transcription factors. Transgenic overexpression of *Artemisia annua* MYB1 (AaMYB1) was shown to increase trichome density and subsequently the production of artemisin (Matias-Hernandez et al., Plant Journal, 90:520-534 (2017)).

Lipid transfer proteins (LTPs) are important in the transport of specialized metabolites in glandular trichomes. Studies have shown that overexpression of LTPs leads to an increase of exudates in plants glandular trichomes (Choi et al., Plant Journal, 70:480-491 (2012)).

Due to the important role of glandular trichomes in the biosynthesis and secretion of terpenoids, there is a need for a greater understanding of the genes, regulatory factors, and signaling mechanisms involved in the control of trichome initiation and development in plants. It is also important to understand the mode of secretion of these specialized metabolites into the cuticle of trichomes. In this disclosure, candidate genes are provided that can be used to modify trichome density in plants. Modification of trichrome density will also improve transport of specialized metabolites in glandular trichomes.

SUMMARY

In one aspect, this disclosure provides a modified plant, seed, or plant part, comprising a recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.

In one aspect, this disclosure provides cured tobacco material from a modified tobacco plant or tobacco plant part comprising a recombinant nucleic acid molecule comprising a nucleic acid sequence at encoding an amino acid sequence least 80% identical or similar to an amino acid sequence selected from the group consisting of SEQ ID NOs: 18-22 and 31-33, wherein said nucleic acid sequence is operably linked to a heterologous promoter.

In one aspect, this disclosure provides a tobacco product comprising material from a modified tobacco plant, tobacco seed, or tobacco plant part comprising a recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.

In one aspect, this disclosure provides a *cannabis* product comprising material from a modified *cannabis* plant, *cannabis* seed, or *cannabis* plant part comprising a recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.

In one aspect, this disclosure provides a recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.

In one aspect, this disclosure provides a method for producing a plant, the method comprising: (a) obtaining at least one plant comprising a recombinant nucleic acid molecule comprising a nucleic acid sequence at least 80% identical to a sequence selected from the group consisting of SEQ ID NOs: 13-17, 23-30, and 34-36, wherein said nucleic acid sequence is operably linked to a heterologous promoter; (b) crossing said at least one plant with at least one plant of a second variety to produce at least one progeny seed; and (c) selecting said at least one progeny seed produced in step (b), or a plant germinated therefrom, wherein said at least one progeny seed or plant germinated therefrom comprises said recombinant nucleic acid molecule.

In one aspect, this disclosure provides a method of generating a modified plant, the method comprising: (a) introducing a recombinant nucleic acid molecule comprising a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell; (b) selecting at least one plant cell from step (a), wherein the at least one plant cell comprises the recombinant nucleic acid molecule; and (c) regenerating a modified plant from the at least one plant cell selected in step (b).

In one aspect, this disclosure provides a method comprising preparing a tobacco product using cured tobacco material from a modified tobacco plant or part therefrom, wherein the modified tobacco plant or part therefrom comprises a recombinant nucleic acid molecule comprises a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell/

In one aspect, this disclosure provides a method comprising preparing a *cannabis* product using material from a modified *cannabis* plant or part therefrom, wherein the modified *cannabis* plant or part therefrom comprises a recombinant nucleic acid molecule comprises a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell.

In one aspect, this disclosure provides a method comprising transforming a plant cell with a recombinant nucleic acid molecule, wherein the recombinant nucleic acid molecule comprises a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell.

In one aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 80% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions.

BRIEF DESCRIPTION OF THE SEQUENCES

SEQ ID NOs: 1 to 12 are primers that can used for the cloning of nucleic acid sequences described herein for expression in transgenic plants.

SEQ ID NOs: 13 to 17 are nucleic acids sequences corresponding to the coding sequences for tobacco genes of interest described herein, specifically NlMYB86, NtGIS, NbGIS, and NtLTP1.

SEQ ID NOs: 18 to 22 are amino acid sequences corresponding to the nucleic acid sequences of SEQ ID NOs: 13 to 17.

SEQ ID NOs: 23 to 27 are nucleic acid sequences corresponding to the genomic sequences for tobacco genes of interest described herein, specifically NtMYB86, NtGIS, NbGIS, and NtLTP1.

SEQ ID NOs: 28 to 30 are nucleic acid sequences corresponding to the coding sequences for *cannabis* genes of interest described herein, specifically MYB61, GIS3, and non-specific lipid transfer protein 1-like.

SEQ ID NOs: 31 to 33 are amino acid sequences corresponding to the nucleic acid sequences of SEQ ID NOs: 28 to 30.

SEQ ID NOs: 34 to 36 are nucleic acid sequences corresponding to the genomic sequences for *cannabis* genes of interest described herein, specifically MYB61, GIS3, and non-specific lipid transfer protein 1-like.

SEQ ID NOs: 37 is a nucleic acid sequence corresponding to the coding sequence for sweet wormwood (*Artemisia annua*) specifically MYB transcription factor.

SEQ ID NOs: 38 is an amino acid sequence corresponding to the nucleic acid sequence of SEQ ID NOs: 37.

SEQ ID NOs: 39 to 43 are nucleic acid sequences corresponding to the coding sequences for tobacco genes of interest described herein, specifically MFS, NMD, CBTS2a (HM), GGPPS2 and cis abienol synthase (ABS).

SEQ ID NOs: 44 to 48 are nucleic acid sequences corresponding to the genomic sequences for tobacco genes of interest described herein, specifically MFS, NMD, CBTS2a (HM), GGPPS2 and cis abienol synthase (ABS).

SEQ ID NOs: 49 to 53 are amino acid sequences corresponding to the nucleic acid sequences of SEQ ID NOs: 39 to 43.

SEQ ID NOs: 54 to 62 and 63 to 71 are nucleic acid sequences corresponding to coding sequences and genomic sequences, respectively, for tobacco LTP genes.

SEQ ID NOs: 72 to 80 are amino acid sequences corresponding to the nucleic acid sequences of SEQ ID NOs: 54 to 62. SEQ ID NO: 81 is a consensus LTP amino acid sequence. SEQ ID NOs: 82 to 91 are subsequences of SEQ ID NOs: 21 and 72 to 80 as shown in FIG. 9. SEQ ID NO: 92 is the consensus amino acid sequence shown in FIG. 9.

Table 1 provides nucleic acid sequences and amino acid sequences used in this disclosure.

TABLE 1

Sequences used in this disclosure

| SEQ ID NO | Sequence Description | Sequence Type |
| --- | --- | --- |
| 1 | NtMYB86-Fwd | Nucleic acid |
| 2 | NtMYB86-Rev | Nucleic acid |
| 3 | Nb/NtGIS-Fwd | Nucleic acid |
| 4 | Nb/NtGIS-Rev | Nucleic acid |
| 5 | qNtMYB86-Fwd2 | Nucleic acid |
| 6 | qNtMYB86-Rev2 | Nucleic acid |
| 7 | qNbGIS-Fwd | Nucleic acid |
| 8 | qNbGIS-Rev | Nucleic acid |
| 9 | NtLTP1isoform1-Fwd | Nucleic acid |

TABLE 1-continued

Sequences used in this disclosure

| SEQ ID NO | Sequence Description | Sequence Type |
|---|---|---|
| 10 | NtLTP1isoform1-Rev | Nucleic acid |
| 11 | NtLTP1isoform2-Fwd | Nucleic acid |
| 12 | NtLTP1isoform2-Rev | Nucleic acid |
| 13 | NtMYB86 (XM_016595116) | Nucleic acid, CDS |
| 14 | NtGIS (XM_016590730) | Nucleic acid, CDS |
| 15 | NbGIS (Niben101Ctg13716g00003) | Nucleic acid, CDS |
| 16 | NtLTP1isoform1 (AB625593) | Nucleic acid, CDS |
| 17 | NtLTP1isoform2 (XM_016578495) | Nucleic acid, CDS |
| 18 | NtMYB86 (XP 016450602) | Amino acid |
| 19 | NtGIS (XP_016446216) | Amino acid |
| 20 | NbGIS | Amino acid |
| 21 | NtLTP1isoform1 (BAK19150) | Amino acid |
| 22 | NtLTP1isoform2 (XP_016433981) | Amino acid |
| 23 | NtMYB86 (XM_016595116) | Nucleic acid, genomic |
| 24 | NtGIS (XM_016590730) | Nucleic acid, genomic |
| 25 | NbGIS (Niben101Ctg13716g00003) | Nucleic acid, genomic |
| 26 | NtLTP1isoform1 (AB625593) | Nucleic acid, genomic |
| 27 | NtLTP1isoform2 (XM_016578495) | Nucleic acid, genomic |
| 28 | MYB61 (*Cannabis sativa*) | Nucleic acid, CDS |
| 29 | Zinc finger protein GIS3 (*Cannabis sativa*) | Nucleic acid, CDS |
| 30 | Non-specific lipid-transfer protein 1-like (*Cannabis sativa*) | Nucleic acid, CDS |
| 31 | MYB61 (*Cannabis sativa*) | Amino acid |
| 32 | Zinc finger protein GIS3 (*Cannabis sativa*) | Amino acid |
| 33 | Non-specific lipid-transfer protein 1-like (*Cannabis sativa*) | Amino acid |
| 34 | MYB61 (*Cannabis sativa*) | Nucleic acid, genomic |
| 35 | Zinc finger protein GIS3 (*Cannabis sativa*) | Nucleic acid, genomic |
| 36 | Non-specific lipid-transfer protein 1-like (*Cannabis sativa*) | Nucleic acid, genomic |
| 37 | MYB transcription factor [*Artemisia annua*] KC118530.1 | Nucleic acid, CDS |
| 38 | MYB transcription factor [*Artemisia annua*] AGR40501.1 | Amino acid |
| 39 | Cytochrome P450_menthofuran synthase (g96188/MFS) | Nucleic acid, CDS |
| 40 | (+)-neomenthol dehydrogenase/ menthone_reductase_(NMD/g29837) | Nucleic acid, CDS |
| 41 | Cembratrienol synthase 2a (CBTS-2a/HM/g58533) | Nucleic acid, CDS |
| 42 | Geranylgeranyl diphosphate synthase (g49326/GGPPS2/GQ911584) | Nucleic acid, CDS |
| 43 | Cis-abienol synthase_Isoform 1 (g2330/AAB) | Nucleic acid, CDS |
| 44 | Cytochrome P450_menthofuran synthase (g96188/MFS) | Nucleic acid, genomic |
| 45 | (+)-neomenthol dehydrogenase/ menthone_reductase (NMD/g29837) | Nucleic acid, genomic |
| 46 | Cembratrienol synthase 2a (CBTS-2a/HM/g58533) | Nucleic acid, genomic |
| 47 | Geranylgeranyl diphosphate synthase (g49326/GGPPS2/GQ911584) | Nucleic acid, genomic |
| 48 | Cis-abienol synthase_Isoform 1 (g2330/AAB) | Nucleic acid, genomic |
| 49 | Cytochrome P450_menthofuran synthase (g96188/MFS) | Amino acid |
| 50 | (+)-neomenthol dehydrogenase/ menthone_reductase (NMD/g29837) | Amino acid |
| 51 | Cembratrienol synthase 2a (CBTS-2a/HM/g58533) | Amino acid |
| 52 | Geranylgeranyl diphosphate synthase (g49326/GGPPS2/GQ911584) | Amino acid |
| 53 | Cis-abienol synthase_Isoform 1 (g2330/AAB) | Amino acid |
| 54 | XM_016601333.1 (XP_016456819.1) | Nucleic acid, CDS |
| 55 | XM_016596613.1 (XP_016452099.1) | Nucleic acid, CDS |
| 56 | XM_016641408.1 (XP_016496894.1) | Nucleic acid, CDS |
| 57 | XM_016607671.1 (XP_016463157.1) | Nucleic acid, CDS |
| 58 | XM_016648588.1 (XP_016504074.1) | Nucleic acid, CDS |
| 59 | XM_016657701.1 (XP_016513187.1) | Nucleic acid, CDS |
| 60 | LTP4 (AB625595.1) | Nucleic acid, CDS |
| 61 | LTP3 (AB625594.1) | Nucleic acid, CDS |
| 62 | LTP2 (AB518680.1) | Nucleic acid, CDS |
| 63 | XM_016601333.1 (XP_016456819.1) | Nucleic acid, genomic |
| 64 | XM_016596613.1 (XP_016452099.1) | Nucleic acid, genomic |
| 65 | XM_016641408.1 (XP_016496894.1) | Nucleic acid, genomic |
| 66 | XM_016607671.1 (XP_016463157.1) | Nucleic acid, genomic |
| 67 | XM_016648588.1 (XP_016504074.1) | Nucleic acid, genomic |
| 68 | XM_016657701.1 (XP_016513187.1) | Nucleic acid, genomic |
| 69 | LTP4 (AB625595.1) | Nucleic acid, genomic |
| 70 | LTP3 (AB625594.1) | Nucleic acid, genomic |
| 71 | LTP2 (AB518680.1) | Nucleic acid, genomic |
| 72 | XP_016456819.1 | Amino acid |
| 73 | XP_016452099.1 | Amino acid |
| 74 | XP_016496894.1 | Amino acid |
| 75 | XP_016463157.1 | Amino acid |
| 76 | XP_016504074.1 | Amino acid |
| 77 | XP_016513187.1 | Amino acid |

TABLE 1-continued

Sequences used in this disclosure

| SEQ ID NO | Sequence Description | Sequence Type |
|---|---|---|
| 78 | LTP4 (BAK19152) | Amino acid |
| 79 | LTP3 (BAK19151) | Amino acid |
| 80 | LTP2 (BAJ25798) | Amino acid |
| 81 | LTP Consensus sequence | Amino acid |
| 82 | XP_016456819.1 FIG. 9 sequence | Amino acid |
| 83 | XP_016452099.1 FIG. 9 sequence | Amino acid |
| 84 | XP_016496894.1 FIG. 9 sequence | Amino acid |
| 85 | XP_016463157.1 FIG. 9 sequence | Amino acid |
| 86 | XP_016504074.1 FIG. 9 sequence | Amino acid |
| 87 | XP_016513187.1 FIG. 9 sequence | Amino acid |
| 88 | LPT4_BAK19152 FIG. 9 sequence | Amino acid |
| 89 | LTP3_BAK19151 FIG. 9 sequence | Amino acid |
| 90 | LPT2_BAJ25798 FIG. 9 sequence | Amino acid |
| 91 | LTP1_BAK19150 FIG. 9 sequence | Amino acid |
| 92 | LTP Consensus FIG. 9 sequence | Amino acid |
| 93 | FIG. 8B consensus sequence | Amino acid |

DETAILED DESCRIPTION

Figure 1:
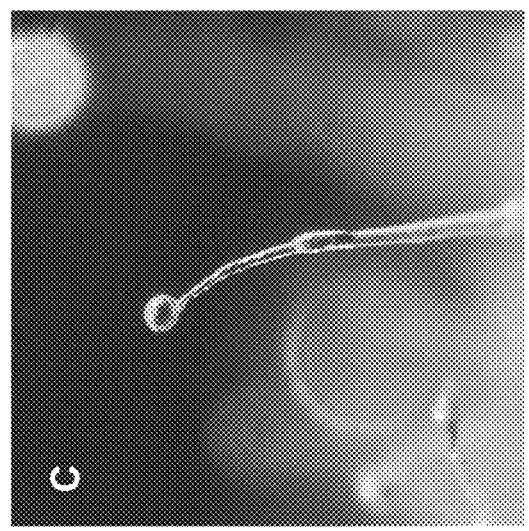
FIG. 1 comprises Panels A, B, and C. Panel A depicts glandular trichomes in *Nicotiana benthamiana*. Panel B depicts glandular trichomes in *Nicotiana tabacum* variety 'TN90', and Panel C depicts glandular trichomes in *Nicotiana tabacum* variety 'Izmir Ego'.
Figure 1:
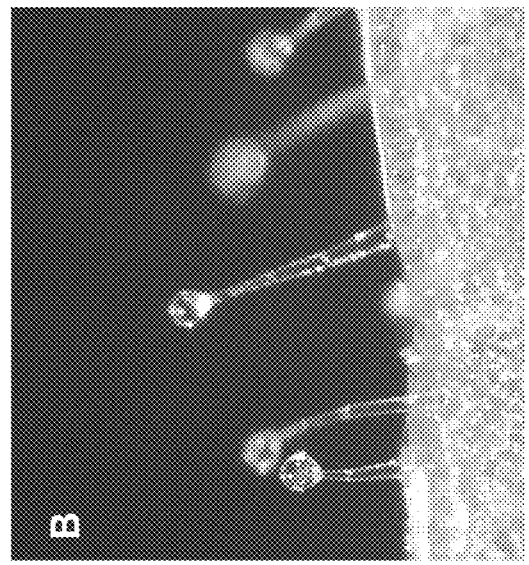
Figure 1:
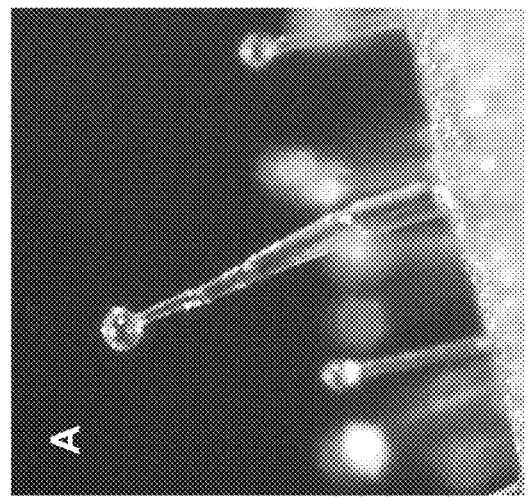

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

When the term "about" is used in reference to a number, it is understood to mean plus or minus 10%. For example, "about 100" would include from 90 to 110.

As used herein, the singular form "a," "an," and "the" include plural references unless the context clearly dictates otherwise. For example, the term "a compound" or "at least one compound" may include a plurality of compounds, including mixtures thereof.

Any tobacco plant, or part thereof, provided herein is specifically envisioned for use with any method provided herein. Similarly, any modified tobacco plant, or part thereof, is specifically envisioned for use with any method provided herein. Any nucleic acid sequence, amino acid sequence, or other composition provided herein is specifically envisioned for use with any method provided herein.

Any *cannabis* plant, or part thereof, provided herein is specifically envisioned for use with any method provided herein. Similarly, any modified *cannabis* plant, or part thereof, is specifically envisioned for use with any method provided herein. Any nucleic acid sequence, amino acid sequence, or other composition provided herein is specifically envisioned for use with any method provided herein.

Trichomes, in general, are hair-like epidermal outgrowths covering most aerial plant tissues. Trichomes tend to be multicellular, but unicellular trichomes are known as well. Multiple types of trichomes can be found on an individual plant, and trichomes vary in shape, size, and cellular organization. An individual trichome can be classified as a glandular trichome or a non-glandular trichome.

Glandular trichomes (see FIG. 1) are characterized by the presence of a head made of cells that can secrete or store large quantities of specialized metabolites (e.g., terpenes). Within the group of glandular trichomes, a trichome can be further characterized as being peltate or capitate. A capitate glandular trichome typically possesses a stalk with a length that is more than twice the height of the head, and the number of cells in the trichome is highly variable. A peltate trichome is a short-stalked trichome with a large head made of between four and eighteen cells arranged in one or two concentric circles.

In an aspect, a trichome is a glandular trichome. In an aspect, a glandular trichome is a capitate glandular trichome. In an aspect, a glandular trichome is a peltate glandular trichome. In an aspect, a glandular trichome is selected from the group consisting of a capitate glandular trichome and a peltate glandular trichome.

In an aspect, glandular trichome initiation and development is regulated by several transcription factors including, but not limited to, genes belonging to MYB and C2H2 transcription factor gene families.

In an aspect, this disclosure provides a modified plant, seed, or plant part comprising a recombinant nucleic acid molecule comprising a nucleic acid sequence encoding a polypeptide operably linked to a heterologous promoter for the initiation and development of trichome to improve its density. In another aspect, this disclosure provides a modified plant, seed, or plant part comprising a nucleic acid sequence encoding a polypeptide operably linked to a heterologous promoter for improving secretion of metabolites to the trichome cuticles. In a further aspect, a modified plant, seed, or plant part is a plant, seed or plant part of the *Nicotiana* genus. In a further aspect, a modified plant, seed, or plant part is a plant, seed or plant part of the *Cannabis* genus.

Transcription Factors Regulation of Trichome Initiation

Transcription factors are known regulators of various biological processes involved in plants growth and development. Several transcription factors have been identified as regulators of glandular trichome initiation. These include, but are not limited to, the transcription factors gene families R2R3-MYB, HD-ZIP IV, MYC, and C2H2 (Chavlin et al., 2020). Overexpression of MYB1 (AaMYB1) in *Artemisia annua* significantly increase production of a sesquiterpene lactone, artemisin, as well as increased trichome density (Matias-Hernandez et al., 2017). Another transcription factor that regulates trichome development as well as terpene biosynthesis is MYC1, a basic helix-loop-helix (bHLH). Knockdown of MYC1 (SIMYC1) in tomato led to significant reduction in monoterpenes as well as the ectopic development of smaller Type VI glandular trichomes at low densities (Xu et al., *Plant Cell*, 30:2988-3005 (2018)). A transcription factor belonging to the C2H2 gene family is also involved in the regulation of trichome development in tobacco. Overexpression of GIS in *Nicotiana benthamiana* (NbGIS) resulted in the increase of glandular trichome density in transgenic lines (Liu et al., Plant Molecular Biology, 98:153-167 (2018)).

Storage and Transportation of Metabolites in Glandular Trichome

Figure 10:
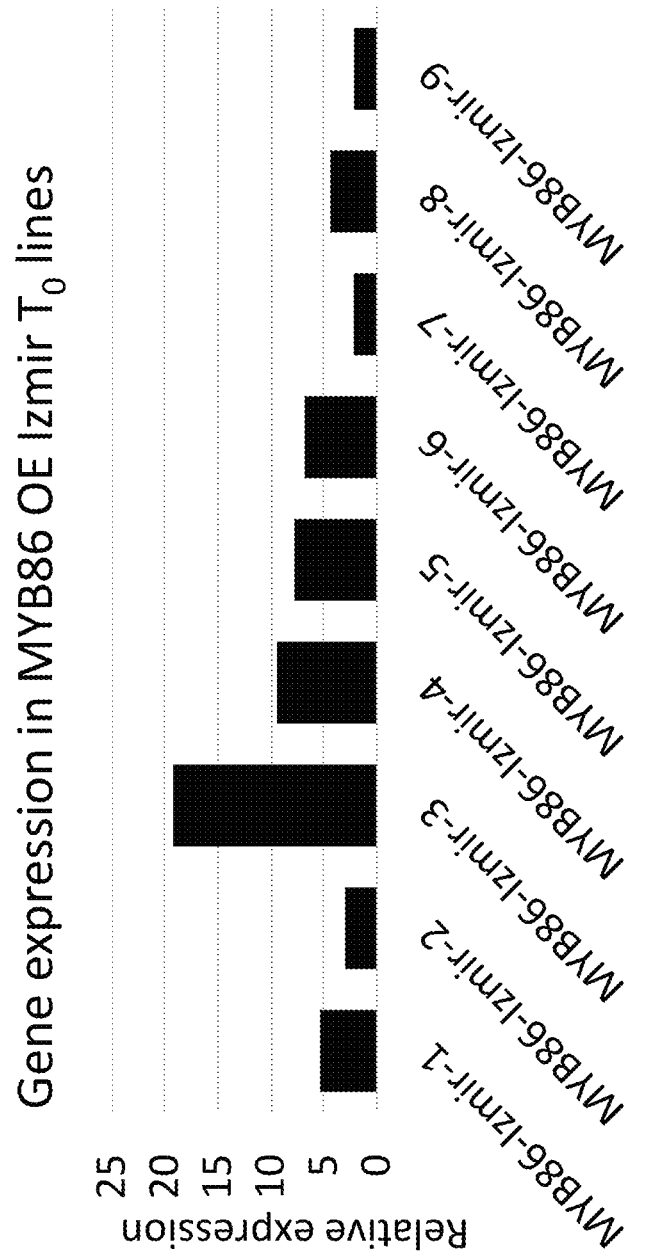
FIG. 10 depicts the relative gene expression of NtMYB86 (SEQ ID NO: 14) in nine independent Izmir Ego transgenic lines in the To generation. The relative gene expression was quantified following the $2^{(-\Delta\Delta C(t))}$ method. See Livak and Schmittgen, Methods, 25:402-408 (2001) for information regarding the $2^{(-\Delta\Delta C(t))}$ method. Expression of NlMYB86 in a wildtype control Izmir Ego plant is used as a baseline (e.g., wildtype expression is set to 1), and is not shown.

Glandular trichomes produce large amount of metabolites which can account for up to 20% of leaf dry weight (Tissier et al., Trends in Plant Science, 22:930-938 (2017)). Trichomes develop morphological features enabling the storage of secondary metabolites. The type, shape, and size of these morphological features depends on the type of glandular trichomes. Nonvolatile compounds, including diterpenoids, are typically produced by capitate glandular trichomes and directly secreted from the tip of the trichome while glandular trichomes that produce volatile compounds have dedicated structures for secretion and storage (Tissier et al., 2017). Transport of hydrophobic molecules in trichomes requires transporters and lipid transfer proteins (LTPs) that facilitate movement of volatile organic compounds to across hydrophilic cell walls and to prevent VOC repartitioning into the plasma membrane (Tissier et al., 2017). LTPs are small (about 10 kDa), soluble proteins that are characterized by a highly conserved cysteine-rich motif (Salminen et al., Planta, 244:971-997 (2016)). See FIG. 10. LTPs are involved in various functions during plant growth and development including, but not limited to, cuticular wax accumulation, pollen and seed development, and cell expansion (Salminen et al., 2016). The trichome-specific NtLTP1 was reported to increase secretion in trichome exudates in tobacco plants as well increasing protection against insect pests when overexpressed (Choi et al., 2012).

Plants

In an aspect, a plant provided herein is a modified plant. In an aspect, a seed provided herein is a modified seed. In an aspect, a plant part provided herein is a modified plant part. As used herein, "modified," in the context of a plant, seed, or plant part, refers to a plant, seed, or plant part, comprising a genetic alteration introduced for certain purposes and beyond natural polymorphisms. Without being limiting, a modified plant, seed, or plant part comprises a recombinant nucleic acid molecule. In another aspect, a modified plant, seed, or plant part comprises a genetic modification. In an aspect, a modified plant, seed, or plant part is a transgenic plant, seed, or plant part.

In an aspect, this disclosure provides a modified plant, seed, or plant part comprising a recombinant nucleic acid molecule comprising a nucleic acid sequence encoding an amino acid sequence at least 80% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 85% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 90% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 95% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 96% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 97% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 98% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 99% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence at least 99.9% identical or similar to an amino acid sequence selected from the group consisting of SEQ ID NOs: 18-22 and 31-33, where the nucleic acid sequence is operably linked to a heterologous promoter. In an aspect, this disclosure provides a modified plant, seed, or plant part comprising a recombinant nucleic acid molecule comprising a nucleic acid sequence encoding an amino acid sequence 100% identical or similar to an amino acid sequence selected from the group consisting of SEQ ID NOs: 18-22 and 31-33, where the nucleic acid sequence is operably linked to a heterologous promoter.

In an aspect, this disclosure provides a modified plant, seed, or plant part comprising a recombinant nucleic acid molecule comprising a nucleic acid sequence encoding an amino acid sequence at least 80%, at least 85%, at least 90%, at least 95%, at least 96%, at least 97%, at least 98%, at least 99%, at least 99.5%, at least 99.9%, or 100% identical or similar to an amino acid sequence selected from the group consisting of SEQ ID NOs: 72-81, where the nucleic acid sequence is operably linked to a heterologous promoter.

In an aspect, this disclosure provides a modified plant, seed, or plant part comprising a recombinant nucleic acid molecule comprising a nucleic acid sequence at least 80% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 85% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 90% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 95% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 96% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 97% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 98% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 99% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence at least 99.9% identical to a nucleic acid sequence selected from the group consisting of SEQ ID NOs: 13-17, 23-30, and 34-36, where the nucleic acid sequence is operably linked to a heterologous promoter. In an aspect, this disclosure provides a modified plant, seed, or plant part comprising a recombinant nucleic acid molecule comprising a nucleic acid sequence 100% identical to a nucleic acid sequence selected from the group consisting of SEQ ID NOs: 13-17, 23-30, and 34-36, where the nucleic acid sequence is operably linked to a heterologous promoter.

In an aspect, this disclosure provides a modified plant, seed, or plant part comprising a recombinant nucleic acid molecule comprising a nucleic acid sequence at least 80%, at least 85%, at least 90%, at least 95%, at least 96%, at least 97%, at least 98%, at least 99%, at least 99.5%, at least 99%, or 100% identical to a nucleic acid sequence selected from the group consisting of SEQ ID NOs: 54-71, where the nucleic acid sequence is operably linked to a heterologous promoter.

In an aspect, at least one leaf of a modified plant comprises a greater average trichome density as compared to a leaf of a control plant grown under comparable conditions. In an aspect, at least one leaf of a modified plant comprises a greater average trichome density on the abaxial side of the leaf as compared to the abaxial side of a leaf of a control plant grown under comparable conditions. In an aspect, at least one leaf of a modified plant comprises a greater average trichome density on the adaxial side of the leaf as compared to the adaxial side of a leaf of a control plant grown under comparable conditions.

In an aspect, at least two leaves of a modified plant comprise a greater average trichome density as compared to two leaves of a control plant grown under comparable conditions. In an aspect, a majority of the leaves of a modified plant comprise a greater average trichome density as compared to the same number of leaves of a control plant grown under comparable conditions. In an aspect, all of the leaves of a modified plant comprise a greater average trichome density as compared to all of the leaves of a control plant grown under comparable conditions.

In an aspect, at least one stem of a modified plant comprises a greater average trichome density as compared to a stem of a control plant grown under comparable conditions. In an aspect, at least one flower of a modified plant comprises a greater average trichome density as compared to a flower of a control plant grown under comparable conditions. In an aspect, at least one root of a modified plant comprises a greater average trichome density as compared to a root of a control plant grown under comparable conditions.

In an aspect, a modified plant comprises a greater average density of glandular trichomes as compared to a control plant. In an aspect, a modified plant comprises a greater average density of non-glandular trichomes as compared to a control plant.

In an aspect, a leaf of a modified tobacco plant comprises at least 70 trichomes per square centimeter. In an aspect, a leaf of a modified tobacco plant comprises at least 75 trichomes per square centimeter. In an aspect, a leaf of a modified tobacco plant comprises at least 80 trichomes per square centimeter. In an aspect, a leaf of a modified tobacco plant comprises at least 85 trichomes per square centimeter. In an aspect, a leaf of a modified tobacco plant comprises at least 90 trichomes per square centimeter. In an aspect, a leaf of a modified tobacco plant comprises at least 95 trichomes per square centimeter. In an aspect, a leaf of a modified tobacco plant comprises at least 100 trichomes per square centimeter. In an aspect, a leaf of a modified tobacco plant comprises at least 105 trichomes per square centimeter. In an aspect, a leaf of a modified tobacco plant comprises at least 110 trichomes per square centimeter. In an aspect, a leaf of a modified tobacco plant comprises at least 115 trichomes per square centimeter. In an aspect, a leaf of a modified tobacco plant comprises at least 120 trichomes per square centimeter. In an aspect, a leaf of a modified tobacco plant comprises at least 125 trichomes per square centimeter. In an aspect, a leaf of a modified tobacco plant comprises at least 130 trichomes per square centimeter. In an aspect, a leaf of a modified tobacco plant comprises at least 140 trichomes per square centimeter. In an aspect, a leaf of a modified tobacco plant comprises at least 150 trichomes per square centimeter.

In an aspect, a leaf of a modified tobacco plant comprises between 60 and 200 trichomes per square centimeter. In an aspect, a leaf of a modified tobacco plant comprises between 60 and 190 trichomes per square centimeter. In an aspect, a leaf of a modified tobacco plant comprises between 60 and 180 trichomes per square centimeter. In an aspect, a leaf of a modified tobacco plant comprises between 60 and 170 trichomes per square centimeter. In an aspect, a leaf of a modified tobacco plant comprises between 60 and 160 trichomes per square centimeter. In an aspect, a leaf of a modified tobacco plant comprises between 60 and 150 trichomes per square centimeter. In an aspect, a leaf of a modified tobacco plant comprises between 60 and 140 trichomes per square centimeter. In an aspect, a leaf of a modified tobacco plant comprises between 60 and 130 trichomes per square centimeter. In an aspect, a leaf of a modified tobacco plant comprises between 60 and 120 trichomes per square centimeter. In an aspect, a leaf of a modified tobacco plant comprises between 60 and 110 trichomes per square centimeter. In an aspect, a leaf of a modified tobacco plant comprises between 60 and 100 trichomes per square centimeter. In an aspect, a leaf of a modified tobacco plant comprises between 60 and 90 trichomes per square centimeter. In an aspect, a leaf of a modified tobacco plant comprises between 60 and 80 trichomes per square centimeter. In an aspect, a leaf of a modified tobacco plant comprises between 60 and 70 trichomes per square centimeter.

In an aspect, a leaf of a modified tobacco plant comprises between 80 and 130 trichomes per square centimeter. In an aspect, a leaf of a modified tobacco plant comprises between 80 and 120 trichomes per square centimeter. In an aspect, a leaf of a modified tobacco plant comprises between 80 and 100 trichomes per square centimeter. In an aspect, a leaf of a modified tobacco plant comprises between 75 and 140 trichomes per square centimeter. In an aspect, a leaf of a modified tobacco plant comprises between 75 and 130 trichomes per square centimeter. In an aspect, a leaf of a modified tobacco plant comprises between 75 and 125 trichomes per square centimeter.

In an aspect, a leaf of a modified tobacco plant comprises at least 1% more trichomes per square centimeter as compared to a control leaf of the same age when grown under comparable conditions. In an aspect, a leaf of a modified tobacco plant comprises at least 5% more trichomes per square centimeter as compared to a control leaf of the same age when grown under comparable conditions. In an aspect, a leaf of a modified tobacco plant comprises at least 10% more trichomes per square centimeter as compared to a control leaf of the same age when grown under comparable conditions. In an aspect, a leaf of a modified tobacco plant comprises at least 15% more trichomes per square centimeter as compared to a control leaf of the same age when grown under comparable conditions. In an aspect, a leaf of a modified tobacco plant comprises at least 20% more trichomes per square centimeter as compared to a control leaf of the same age when grown under comparable conditions. In an aspect, a leaf of a modified tobacco plant comprises at least 25% more trichomes per square centimeter as compared to a control leaf of the same age when grown under comparable conditions. In an aspect, a leaf of a modified tobacco plant comprises at least 30% more trichomes per square centimeter as compared to a control leaf of the same age when grown under comparable conditions. In an aspect, a leaf of a modified tobacco plant comprises at least 40% more trichomes per square centimeter as compared to a control leaf of the same age when grown under comparable conditions. In an aspect, a leaf of a modified tobacco plant comprises at least 50% more trichomes per square centimeter as compared to a control leaf of the same age when grown under comparable conditions. In an aspect, a leaf of a modified tobacco plant comprises at least 60% more trichomes per square centimeter as compared to a control leaf of the same age when grown under comparable conditions. In an aspect, a leaf of a modified tobacco plant comprises at least 70% more trichomes per square centimeter as compared to a control leaf of the same age when grown under comparable conditions. In an aspect, a leaf of a modified tobacco plant comprises at least 80% more trichomes per square centimeter as compared to a control leaf of the same age when grown under comparable conditions. In an aspect, a leaf of a modified tobacco plant comprises at least 90% more trichomes per square centimeter as compared to a control leaf of the same age when grown under comparable conditions. In an aspect, a leaf of a modified tobacco plant comprises at least 100% more trichomes per square centimeter as compared to a control leaf of the same age when grown under comparable conditions. In an aspect, a leaf of a modified tobacco plant comprises at least 110% more trichomes per square centimeter as compared to a control leaf of the same age when grown under comparable conditions. In an aspect, a leaf of a modified tobacco plant comprises at least 125% more trichomes per square centimeter as compared to a control leaf of the same age when grown under comparable conditions. In an aspect, a leaf of a modified tobacco plant comprises at least 150% more trichomes per square centimeter as compared to a control leaf of the same age when grown under comparable conditions. In an aspect, a leaf of a modified tobacco plant comprises at least 200% more trichomes per square centimeter as compared to a control leaf of the same age when grown under comparable conditions.

It will be understood that, unless otherwise specified, a comparison between a modified leaf and a leaf from a control plant grown under comparable conditions must use leaves that are of the same leaf number (e.g., a modified V5 leaf must be compared to a control V5 leaf) on the modified and control plants.

In an aspect, a plant is a tobacco plant. In an aspect, a plant is a *Nicotiana* plant. In an aspect, a tobacco plant is a *Nicotiana tabacum* plant.

In an aspect, a *Nicotiana* plant, seed, or plant part is selected from the group consisting of *Nicotiana tabacum, Nicotiana amplexicaulis* PI 271989; *Nicotiana benthamiana*

PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572.

In an aspect, a seed is a tobacco seed. In an aspect, a seed is a *Nicotiana* seed. In an aspect, a tobacco seed is a *Nicotiana tabacum* or *Nicotiana benthamiana* seed.

In an aspect, a plant part is a tobacco plant part. In an aspect, a plant part is a *Nicotiana* plant part. In an aspect, a tobacco plant part is a *Nicotiana tabacum* plant part or a *Nicotiana benthamiana* plant part.

In an aspect, a plant is a *cannabis* plant. In an aspect, a plant is a *Cannabis* plant. In an aspect, a *cannabis* plant is a *Cannabis sativa* plant. In an aspect, a *cannabis* plant is a *Cannabis indica* plant. In an aspect, a *cannabis* plant is a *Cannabis ruderalis* plant. In an aspect, a *cannabis* plant is selected from the group consisting of *Cannabis sativa, Cannabis indica,* and *Cannabis ruderalis*.

In an aspect, a seed is a *cannabis* seed. In an aspect, a seed is a *Cannabis* seed. In an aspect, a *cannabis* seed is a *Cannabis sativa* seed. In an aspect, a *cannabis* seed is a *Cannabis indica* seed. In an aspect, a *cannabis* seed is a *Cannabis ruderalis* seed. In an aspect, a *cannabis* seed is selected from the group consisting of *Cannabis sativa, Cannabis indica,* and *Cannabis ruderalis*.

In an aspect, a plant part is a *cannabis* plant part. In an aspect, a plant part is a *Cannabis* plant part. In an aspect, a *cannabis* plant part is a *Cannabis sativa* plant part. In an aspect, a *cannabis* plant part is a *Cannabis* indica plant part. In an aspect, a *cannabis* plant part is a *Cannabis ruderalis* plant part. In an aspect, a *cannabis* plant part is selected from the group consisting of *Cannabis sativa, Cannabis indica,* and *Cannabis ruderalis*.

In an aspect, a plant part provided includes, but is not limited to, a leaf, a stem, a root, a trichome, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, a plant part does not include a seed. In an aspect, this disclosure provides plant cells, tissues, and organs that are not reproductive material and do not mediate the natural reproduction of the plant. In another aspect, this disclosure also provides plant cells, tissues, and organs that are reproductive material and mediate the natural reproduction of the plant. In another aspect, this disclosure provides plant cells, tissues, and organs that cannot maintain themselves via photosynthesis. In another aspect, this disclosure provides somatic plant cells. Somatic cells, contrary to germline cells, do not mediate plant reproduction.

Cells, tissues and organs can be from seed, fruit, leaf, cotyledon, hypocotyl, meristem, embryos, endosperm, root, shoot, stem, trichome, pod, flower, inflorescence, stalk, pedicel, style, stigma, receptacle, petal, sepal, pollen, anther, filament, ovary, ovule, pericarp, phloem, vascular tissue. In another aspect, this disclosure provides a plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco and *cannabis* plants naturally reproduce via seeds, not via asexual reproduction or vegetative propagation. In an aspect, this disclosure provides plant endosperm.

This disclosure provides cells from plants provided herein.

As used herein, a "progeny plant" or "progeny seed" can be from any filial generation, e.g., $F_1$, $F_2$, $F_3$, $F_4$, $F_5$, $F_6$, $F_7$, etc.

In an aspect, a tobacco plant, seed, or plant part, is of a tobacco variety selected from the group consisting of a flue-cured variety, a bright variety, a Burley variety, a Virginia variety, a Maryland variety, a dark variety, a Galpão variety, an Oriental variety, and a Turkish variety.

In an aspect, a tobacco cell is of a tobacco variety selected from the group consisting of a flue cured variety, a bright variety, a Burley variety, a Virginia variety, a Maryland variety, a dark variety, a Galpão variety, an Oriental variety, and a Turkish variety.

In an aspect, a tobacco leaf is of a tobacco variety selected from the group consisting of a flue cured variety, a bright variety, a Burley variety, a Virginia variety, a Maryland variety, a dark variety, a Galpão variety, an Oriental variety, and a Turkish variety.

In an aspect, a cured tobacco leaf or plant part is of a tobacco variety selected from the group consisting of a flue cured variety, a bright variety, a Burley variety, a Virginia variety, a Maryland variety, a dark variety, a Galpão variety, an Oriental variety, and a Turkish variety. Skilled artisans further understand that cured tobacco does not constitute a living organism and is not capable of growth or reproduction Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, tobacco plants, seeds, or plant parts provided herein are of a flue-cured tobacco variety selected from the group consisting of the varieties listed in Table 2, and any variety essentially derived from any one of the foregoing varieties. See WO 2004/041006 A1. In a further aspect, tobacco plants, seeds, or plant parts provided herein are in a flue-cured variety selected from the group consisting of K326, K346, and NC196.

TABLE 2

| Flue-cured Tobacco Varieties |
|---|
| 400 (TC 225) |
| 401 (TC 226) |
| 401 Cherry Red (TC 227) |
| 401 Cherry Red Free (TC 228) |
| Cash (TC 250) |
| Cash (TI 278) |
| CC 101 |
| CC 1063 |
| CC 13 |
| CC 143 |
| CC 200 |
| CC 27 |
| CC 301 |
| CC 33 |
| CC 35 |
| CC 37 |
| CC 400 |

TABLE 2-continued

Flue-cured Tobacco Varieties

| | |
|---|---|
| CC 500 | NC 297 |
| CC 600 | NC 299 |
| CC 65 | NC 37 NF (TC 350) |
| CC 67 | NC 471 |
| CC 700 | NC 55 |
| CC 800 | NC 567 (TC 362) |
| CC 900 | NC 60 (TC 352) |
| Coker 139 (TC 259) | NC 606 |
| Coker 139 yb1, yb2 | NC 6140 |
| Coker 140 (TC 260) | NC 71 |
| Coker 176 (TC 262) | NC 72 |
| Coker 187 (TC 263) | NC 729 (TC 557) |
| Coker 187-Hicks (TC 265) | NC 810 (TC 659) |
| Coker 209 (TC 267) | NC 82 (TC 356) |
| Coker 258 (TC 270) | NC 8640 |
| Coker 298 (TC 272) | NC 89 (TC 359) |
| Coker 316 (TC 273) | NC 92 |
| Coker 319 (TC 274) | NC 925 |
| Coker 347 (TC 275) | NC 95 (TC 360) |
| Coker 371-Gold (TC 276) | NC 98 (TC 361) |
| Coker 411 (TC 277) | NC EX 24 |
| Coker 48 (TC 253) | NC PY 10 (TC 367) |
| Coker 51 (TC 254) | NC TG 61 |
| Coker 86 (TC 256) | Oxford 1 (TC 369) |
| CU 263 (TC 619) | Oxford 1-181 (TC 370) |
| CU 561 | Oxford 2 (TC 371) |
| DH95-1562-1 | Oxford 207 (TC 632) |
| Dixie Bright 101 (TC 290) | Oxford 26 (TC 373) |
| Dixie Bright 102 (TC 291) | Oxford 3 (TC 372) |
| Dixie Bright 244 (TC 292) | Oxford 414 NF |
| Dixie Bright 27 (TC 288) | PD 611 (TC 387) |
| Dixie Bright 28 (TC 289) | PVH 03 |
| GF 157 | PVH 09 |
| GF 318 | PVH 1118 |
| GL 26H | PVH 1452 |
| GL 338 | PVH 1600 |
| GL 350 | PVH 2110 |
| GL 368 | PVH 2275 |
| GL 395 | R 83 (Line 256-1) (TI 1400) |
| GL 600 | Reams 134 |
| GL 737 | Reams 158 |
| GL 939 | Reams 713 |
| GL 939 (TC 628) | Reams 744 |
| Hicks (TC 310) | Reams M1 |
| Hicks Broadleaf (TC 311) | RG 11 (TC 600) |
| K 149 (TC 568) | RG 13 (TC 601) |
| K 317 | RG 17 (TC 627) |
| K 326 | RG 22 (TC 584) |
| K 326 (TC 319) | RG 8 (TC 585) |
| K 340 (TC 320) | RG 81 (TC 618) |
| K 346 | RG H51 |
| K 346 (TC 569) | RG4H 217 |
| K 358 | RGH 12 |
| K 394 (TC 321) | RGH 4 |
| K 399 | RGH 51 |
| K 399 (TC 322) | RGH 61 |
| K 730 | SC 58 (TC 400) |
| Lonibow (TI 1573) | SC 72 (TC 403) |
| Lonibow (TI 1613) | Sp. G-168 |
| McNair 10 (TC 330) | SPEIGHT 168 |
| McNair 135 (TC 337) | Speight 168 (TC 633) |
| McNair 30 (TC 334) | Speight 172 (TC 634) |
| McNair 373 (TC 338) | Speight 178 |
| McNair 944 (TC 339) | Speight 179 |
| MK94 (TI 1512) | Speight 190 |
| MS K 326 | Speight 196 |
| MS NC 71 | SPEIGHT 220 |
| MS NC 72 | SPEIGHT 225 |
| NC 100 | SPEIGHT 227 |
| NC 102 | SPEIGHT 236 |
| NC 1071 (TC 364) | Speight G-10 (TC 416) |
| NC 1125-2 | Speight G-102 |
| NC 12 (TC 346) | Speight G-108 |
| NC 1226 | Speight G-111 |
| NC 196 | Speight G-117 |
| NC 2326 (TC 365) | Speight G-126 |
| NC 27 NF (TC 349) | Speight G-15 (TC 418) |
| NC 291 | Speight G-23 |

TABLE 2-continued

Flue-cured Tobacco Varieties

Speight G-28 (TC 420)
Speight G-33
Speight G-41
Speight G-5
Speight G-52
Speight G-58
Speight G-70
Speight G-70 (TC 426)
Speight G-80 (TC 427)
Speight NF3 (TC 629)
STNCB
VA 182
VA 45 (TC 559)
Vesta 30 (TC 439)
Vesta 33 (TC 440)
Vesta 5 (TC 438)
Vesta 62 (TC 441)
Virginia (TI 220)
Virginia (TI 273)
Virginia (TI 877)
Virginia 115 (TC 444)
Virginia 21 (TC 443)
Virginia Bright (TI 964)
Virginia Bright Leaf (TC 446)
Virginia Gold (TC 447)
White Stem Orinoco (TC 451)

Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, tobacco plants, seeds, or plant parts provided herein are of a Burley tobacco variety selected from the group consisting of the tobacco varieties listed in Table 3, and any variety essentially derived from any one of the foregoing varieties. In a further aspect, tobacco plants, seeds, or plant parts provided herein are in a Burley variety selected from the group consisting of TN 90, KT 209, KT 206, KT212, and HB 4488.

TABLE 3

Burley Tobacco Varieties

4407 LC
AA-37-1
Burley 21 (TC 7)
Burley 49 (TC 10)
Burley 64 (TC 11)
Burley Mammoth KY 16 (TC 12)
Clay 402
Clay 403
Clay 502
Clays 403
GR 10 (TC 19)
GR 10 (TC 19)
GR 10A (TC 20)
GR 13 (TC 21)
GR 14 (TC 22)
GR 149 LC
GR 153
GR 17 (TC 23)
GR 17B (TC 24)

TABLE 3-continued

Burley Tobacco Varieties

GR 18 (TC 25)
GR 19 (TC 26)
GR 2 (TC 15)
GR 24 (TC 27)
GR 36 (TC 28)
GR 38 (TC 29)
GR 38A (TC 30)
GR 40 (TC 31)
GR 42 (TC 32)
GR 42C (TC 33)
GR 43 (TC 34)
GR 44 (TC 35)
GR 45 (TC 36)
GR 46 (TC 37)
GR 48 (TC 38)
GR 5 (TC 16)
GR 53 (TC 39)
GR 6 (TC 17)
GR 9 (TC 18)
GR 139 NS
GR 139 S
HB 04P
HB 04P LC
HB 3307P LC
HB 4108P
HB 4151P
HB 4192P
HB 4194P
HB 4196
HB 4488
HB 4488P
HB04P
HB 4488 LC
HIB 21
HPB 21
HY 403
Hybrid 403 LC
Hybrid 404 LC
Hybrid 501 LC
KDH-959 (TC 576)
KDH-960 (TC 577)
KT 200 LC
KT 204 LC
KT 206 LC
KT 209 LC
KT 210 LC
KT 212 LC
KT 215 LC
KY 1 (TC 52)
KY 10 (TC 55)
KY 12 (TC 56)
KY 14 (TC 57)
KY 14 × L8 LC
KY 15 (TC 58)
KY 16 (TC 59)
KY 17 (TC 60)
KY 19 (TC 61)
KY 21 (TC 62)
KY 22 (TC 63)
KY 24 (TC 64)
KY 26 (TC 65)
KY 33 (TC 66)
KY 34 (TC 67)
KY 35 (TC 68)
KY 41A (TC 69)
KY 5 (TC 53)
KY 52 (TC 70)
KY 54 (TC 71)
KY 56 (TC 72)
KY 56 (TC 72)
KY 57 (TC 73)
KY 58 (TC 74)
KY 8654 (TC 77)
KY 8959
KY 9 (TC 54)
KY 907 LC
KY 908 (TC 630)
NBH 98 (Screened)

TABLE 3-continued

Burley Tobacco Varieties

NC 1206
NC 129
NC 2000 LC
NC 2002 LC
NC 3 LC
NC 5 LC
NC 6 LC
NC 7 LC
NC BH 129 LC
NC03-42-2
Newton 98
R 610 LC
R 630 LC
R 7-11
R 7-12 LC
RG 17
TKF 1801 LC
TKF 2002 LC
TKF 4024 LC
TKF 4028 LC
TKF 6400 LC
TKF 7002 LC
TKS 2002 LC
TN 86 (TC 82)
TN 90 LC
TN 97 Hybrid LC
TN 97 LC
VA 116
VA 119
Virgin A Mutante (TI 1406)
Virginia 509 (TC 84)

In another aspect, tobacco plants, seeds, or plant parts provided herein are of a Maryland tobacco variety selected from the group consisting of the tobacco varieties listed in Table 4, and any variety essentially derived from any one of the foregoing varieties.

TABLE 4

Maryland Tobacco Varieties

Maryland 10 (TC 498)
Maryland 14 D2 (TC 499)
Maryland 201 (TC 503)
Maryland 21 (TC 500)
Maryland 341 (TC 504)
Maryland 40
Maryland 402
Maryland 59 (TC 501)
Maryland 601
Maryland 609 (TC 505)
Maryland 64 (TC 502)
Maryland 872 (TC 506)
Maryland Mammoth (TC 507)

Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, tobacco plants, seeds, or plant parts provided herein are of a dark air-cured tobacco variety selected from the group consisting of Sumatra, Jatim, Dominican Cubano, Besuki, One sucker, Green River, Virginia sun-cured, and Paraguan Passado, and any variety essentially derived from any one of the foregoing varieties.

Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, tobacco plants, seeds, or plant parts provided herein are of a dark fire-cured tobacco variety selected from the group consisting of the tobacco varieties listed in Table 5, and any variety essentially derived from any one of the foregoing varieties.

TABLE 5

Dark Fire-Cured Tobacco Varieties

Black Mammoth (TC 461)
Black Mammoth Small Stalk (TC 641)
Certified Madole (TC 463)
D-534-A-1 (TC 464)
DAC ULT 302
DAC ULT 303
DAC ULT 306
DAC ULT 308
DAC ULT 312
DF 300 (TC 465)
DF 485 (TC 466)
DF 516 (TC 467)
DF 911 (TC 468)
DT 508
DT 518 (Screened)
DT 538 LC
DT 592
Improved Madole (TC 471)
Jemigan's Madole (TC 472)
KT 14LC
KT D17LC
KT D4 LC
KT D6 LC
KT D8 LC
KY 153 (TC 216)
KY 157 (TC 217)
KY 160
KY 160 (TC 218)
KY 163 (TC 219)
KY 165 (TC 220)
KY 170 (TC 474)
KY 171 (PhPh)
KY 171 (TC 475)
KY 171 LC
KY 171 NS
KY 180 (TC 573)
KY 190 (TC 574)
Little Crittenden
Little Crittenden (TC 476)
Little Crittenden LC (certified)
Little Crittenden PhPh
Lizard Tail Turtle Foot
Madole (TC 478)
Madole (TC 479)
MS KY 171
MS NL Madole LC
MS TN D950 LC
Nance (TC 616)
Narrow Leaf Madole LC (certified)
Neal Smith Madole (TC 646)
Newtons VH Madole
NL Madole
NL Madole (PhPh)
NL Madole (TC 484)
NL Madole LC
NL Madole LC (PhPh)
NL Madole NS
One Sucker (TC 224)
OS 400
PD 302H
PD 312H
PD 318H
PD 7302 LC
PD 7305
PD 7309 LC
PD 7312 LC
PD 7318 LC
PD 7319 LC
Petico M PG04

TABLE 5-continued

Dark Fire-Cured Tobacco Varieties

PY KY 160 (TC 612)
PY KY 171 (TC 613)
Shirey
TI 1372
TN D94
TN D94 (TC 621)
TN D950
TN D950 (PhPh)
TN D950
TN D950 (TC 622)
TR Madole (TC 486)
VA 309
VA 309 (TC 560)
VA 309 LC (certified)
VA 310 (TC 487)
VA 331 (TC 592)
VA 355 (TC 638)
VA 359
VA 359 (Screened)
VA 359 (TC 639)
VA 359 LC (certified)
VA 403 (TC 580)
VA 405 (TC 581)
VA 409 (TC 562)
VA 510 (TC 572)

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, tobacco plants, seeds, or plant parts provided herein are of an Oriental tobacco variety selected from the group consisting of the tobacco varieties listed in Table 6, and any variety essentially derived from any one of the foregoing varieties.

TABLE 6

Oriental Tobacco Varieties

Bafra (TI 1641)
Bahce (TI 1730)
Bahia (TI 1416)
Bahia (TI 1455)
Baiano (TI 128)
Basma
Basma (TI 1666)
Basma Drama
Basma Hybrid (PhPh)
Basma Zihna I
Bitlis (TI 1667)
Bitlis (TI 1725)
Bubalovac (TI 1282)
Bursa (TI 1650)
Bursa (TI 1668)
Canik (TI 1644)
Djebel 174 (TI 1492)
Djebel 359 (TI 1493)
Djebel 81
Dubec 566 (TI 1409)
Dubec 7 (TI 1410)
Dubek 566 (TI 1567)
Duzce (TI 1670)
Edime (TI 1671)
Ege (TI 1642)
Ege-64 (TI 1672)
Izmir (Akhisar) (TI 1729)
Izmir (Gavurkoy) (TI 1727)
Izmir Ege 64

TABLE 6-continued

Oriental Tobacco Varieties

Izmir-Incekara (TI 1674)
Izmir-Ozbas (TI 1675)
Jaka Dzebel (TI 1326)
Kaba-Kulak
Kagoshima Mamba (TI 158)
Katerini
Katerini S53
Krumovgrad 58
MS Basma
MS Katerini S53
Nevrokop 1146
Ozbas (TI 1645)
Perustitza (TI 980)
Prilep (TI 1291)
Prilep (TI 1325)
Prilep 12-2/1
Prilep 23
Samsun (TC 536)
Samsun 959 (TI 1570)
Samsun Evkaf (TI 1723)
Samsun Holmes NN (TC 540)
Samsun Maden (TI 1647)
Samsun NO 15 (TC 541)
Samsun-BLK SHK Tol (TC 542)
Samsun-Canik (TI 1678)
Samsun-Maden (TI 1679)
Saribaptar 407 - Izmir Region
Smyrna (TC 543)
Smyrna No. 23 (TC 545)
Smyrna No. 9 (TC 544)
Smyrna-Blk Shk Tol (TC 546)
Trabzon (TI 1649)
Trabzon (TI 1682)
Trapezund 161 (TI 1407)
Turkish (TC 548)
Turkish Angshit (TI 90)
Turkish Samsum (TI 92)
Turkish Tropizoid (TI 93)
Turkish Varotic (TI 89)
Xanthi (TI 1662)

In an aspect, tobacco plants, seeds, or plant parts provided herein are of a cigar tobacco variety selected from the group consisting of the tobacco varieties listed in Table 7, and any variety essentially derived from any one of the foregoing varieties.

TABLE 7

Cigar Tobacco Varieties

Bahai (TI 62)
Beinhart 1000
Beinhart 1000 (TI 1562)
Beinhart 1000-1 (TI 1561)
Bergerac C
Bergerac C (TI 1529)
Big Cuban (TI 1565)
Castillo Negro, Blanco, Pina (TI 448)
Castillo Negro, Blanco, Pina (TI 448A)
Castillo Negro, Blanco, Pina (TI 449)
Caujaro (TI 893)
Chocoa (TI 289)
Chocoa (TI 313)
Connecticut 15 (TC 183)
Connecticut Broadleaf
Connecticut Broadleaf (TC 186)
Connecticut Shade (TC 188)
Criollo, Colorado (TI 1093)
Enshu (TI 1586)
Florida 301
Florida 301 (TC 195)
PA Broadleaf (TC 119)
Pennsylvania Broadleaf
Pennsylvania Broadleaf (TC 119)

TABLE 7-continued

Cigar Tobacco Varieties

Petite Havana SR1
Petite Havana SR1 (TC 105)

In an aspect, tobacco plants, seeds, or plant parts provided herein are of a tobacco variety selected from the group consisting of the tobacco varieties listed in Table 8, and any variety essentially derived from any one of the foregoing varieties.

TABLE 8

Other Tobacco Varieties

Chocoa (TI 319)
Hoja Parada (TI 1089)
Hoja Parado (Galpoa) (TI 1068)
Perique (St. James Parrish)
Perique (TC 556)
Perique (TI 1374)
Sylvestris (TI 984)
TI 179

In an aspect, a tobacco plant or plant part is from a variety selected from the group consisting of the tobacco varieties listed in Table 2, Table 3, Table 4, Table 5, Table 6, Table 7, and Table 8. In another aspect, a tobacco plant or plant part is from a variety listed in Table 2. In another aspect, a tobacco plant or plant part is from a variety listed in Table 3. In another aspect, a tobacco plant or plant part is from a variety listed in Table 4. In another aspect, a tobacco plant or plant part is from a variety listed in Table 5. In another aspect, a tobacco plant or plant part is from a variety listed in Table 6. In another aspect, a tobacco plant or plant part is from a variety listed in Table 7. In another aspect, a tobacco plant or plant part is from a variety listed in Table 8.

In an aspect, a tobacco seed is from a variety selected from the group consisting of the tobacco varieties listed in Table 2, Table 3, Table 4, Table 5, Table 6, Table 7, and Table 8. In another aspect, a tobacco seed is from a variety listed in Table 2. In another aspect, a tobacco seed is from a variety listed in Table 3. In another aspect, a tobacco seed is from a variety listed in Table 4. In another aspect, a tobacco seed is from a variety listed in Table 5. In another aspect, a tobacco seed is from a variety listed in Table 6. In another aspect, a tobacco seed is from a variety listed in Table 7. In another aspect, a tobacco seed is from a variety listed in Table 8.

In an aspect, a tobacco cell is from a variety selected from the group consisting of the tobacco varieties listed in Table 2, Table 3, Table 4, Table 5, Table 6, Table 7, and Table 8. In another aspect, a tobacco cell is from a variety listed in Table 2. In another aspect, a tobacco cell is from a variety listed in Table 3. In another aspect, a tobacco cell is from a variety listed in Table 4. In another aspect, a tobacco cell is from a variety listed in Table 5. In another aspect, a tobacco cell is from a variety listed in Table 6. In another aspect, a tobacco cell is from a variety listed in Table 7. In another aspect, a tobacco cell is from a variety listed in Table 8.

All foregoing mentioned specific varieties of flue-cured, dark air-cured, Burley, Maryland, dark fire-cured, cigar, or Oriental type are listed only for exemplary purposes. Any additional flue-cured, dark air-cured, Burley, Maryland, dark fire-cured, cigar, or Oriental varieties are also contemplated in the present application.

In an aspect, a plant or variety provided herein is an inbred plant or variety. As used herein, an "inbred" variety is a variety that has been bred for genetic homogeneity.

As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an Ex F hybrid. The first and second hybrids can be further crossed to create the higher order hybrid (C×D)×(E×F) comprising genetic information from all four parent varieties. In an aspect, a plant or seed provided herein is a hybrid plant or seed.

In an aspect, a tobacco plant provided herein is an inbred tobacco plant. In an aspect, a tobacco seed provided herein is an inbred tobacco seed. In an aspect, a tobacco plant provided herein is a hybrid tobacco plant. In another aspect, a tobacco seed provided herein is a hybrid tobacco seed.

In an aspect, a *cannabis* plant provided herein is an inbred *cannabis* plant. In an aspect, a *cannabis* seed provided herein is an inbred *cannabis* seed. In an aspect, a *cannabis* plant provided herein is a hybrid *cannabis* plant. In an aspect, a *cannabis* seed provided herein is a hybrid *cannabis* seed.

Unless specified otherwise, all comparisons to control plants require similar growth conditions or comparable growth conditions for the two plants being compared. As used herein, "grown under comparable conditions," "similar growth conditions" or "comparable growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

As used herein, a "control plant" refers to a plant of identical, or nearly identical, genetic makeup as the modified plant being compared, except for the recombinant nucleic acid molecule provided herein that was introduced to the modified plant.

In an aspect, a plant or variety provided herein is male sterile. In another aspect, a plant or variety provided herein is cytoplasmic male sterile (CMS). Male sterile plants can be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Co., Inc., New York, N. Y. 761 pp.

In another aspect, a plant or variety provided herein is female sterile. As a non-limiting example, female sterile plants can be made by mutating the STIG1 gene. See, for example, Goldman et al. 1994, EMBO Journal 13:2976-2984.

In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 80% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 85% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 90% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 92.5% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 95% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 96% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 97% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 98% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 99% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is at least 99.9% identical to a sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence is sequence selected from the group consisting of SEQ ID NOs: 13-17, 23-30, and 34-36, or a functional fragment thereof; and (b) selecting at least one progeny seed produced in step (a), or a plant germinated therefrom, where the at least one progeny seed or plant germinated therefrom comprises the recombinant nucleic acid molecule.

In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 80% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 85% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 90% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 95% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 96% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 97% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 98% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 99% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence at least 99.9% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule. In an aspect, this disclosure provides a method for producing a plant, the method comprising: (a) crossing at least one plant of a first variety with at least one plant of a second variety to produce at least one progeny seed, where the at least one plant of the first variety comprises a recombinant nucleic acid molecule comprising a promoter operably linked to a heterologous nucleic acid sequence, where the nucleic acid sequence encodes an amino acid sequence 100% identical or similar to an amino acid sequence selected from the group consisting of SEQ ID NOs: 18-22 and 31-33, or a functional fragment thereof; and (b) selecting at least one progeny seed produced in step (a), or a plant germinated therefrom, where the at least one progeny seed or plant germinated therefrom comprises the recombinant nucleic acid molecule.

In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 80% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 85% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 90% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 95% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 96% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 97% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 98% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 99% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence at least 99.9% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide comprises a nucleic acid sequence 100% identical to a nucleic acid sequence selected from the group consisting of SEQ ID NOs: 13-17, 23-30, and 34-36; (b) regenerating a modified plant from the at least one plant cell in step (a), where the modified plant comprises an increased trichome density on at least one leaf as compared to a leaf from a control plant lacking the recombinant nucleic acid when grown under comparable conditions.

In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 80% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 85% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 90% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 92.5% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 95% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 96% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 97% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 98% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 99% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence at least 99.9% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions. In an aspect, this disclosure provides a method for producing a plant with increased trichome density, the method comprising: (a) providing to at least one plant cell a recombinant nucleic acid comprising a heterologous promoter operably linked to a polynucleotide, where the polynucleotide encodes an amino acid sequence 100% identical or similar to an amino acid sequence selected from the group consisting of SEQ ID NOs: 18-22 and 31-33; (b) regenerating a modified plant from the at least one plant cell in step (a), where the modified plant comprises an increased trichome density on at least one leaf as compared to a leaf from a control plant lacking the recombinant nucleic acid when grown under comparable conditions.

In an aspect, a first plant variety and a second plant variety are the same variety. In an aspect, a first plant variety and a second plant variety are two different varieties. In an aspect, a second plant variety comprises a recombinant nucleic acid molecule.

In an aspect, a first plant variety is heterozygous for a recombinant nucleic acid molecule. In an aspect, a first plant variety is hemizygous for a recombinant nucleic acid molecule. In an aspect, a first plant variety is homozygous for a recombinant nucleic acid molecule. In an aspect, a second plant variety is heterozygous for a recombinant nucleic acid molecule. In an aspect, a second plant variety is hemizygous for a recombinant nucleic acid molecule. In an aspect, a second plant variety is homozygous for a recombinant nucleic acid molecule. In an aspect, a progeny seed, or a plant germinated therefrom, is heterozygous for a recombinant nucleic acid molecule. In an aspect, a progeny seed, or a plant germinated therefrom, is hemizygous for a recombinant nucleic acid molecule. In an aspect, a progeny seed, or a plant germinated therefrom, is homozygous for a recombinant nucleic acid molecule.

In an aspect, a first plant variety is a tobacco plant variety. In an aspect, a second plant variety is a tobacco plant variety. In an aspect, a first plant variety is a *cannabis* plant variety. In an aspect, a second plant variety is a *cannabis* plant variety.

As used herein, the term "crossing" refers to the deliberate mating of two plants. In an aspect, crossing comprises pollination and/or fertilization of a first plant by a second plant. The two plants being crossed can be distantly related, closely related, or identical. In an aspect, the two plants being crossed are both modified plants. In an aspect, the two plants being crossed are of the same variety. In an aspect, the two plants being crossed are of two different varieties. In an aspect, one of the two plants being crossed is male sterile. In an aspect, one of the two plants being crossed is female sterile. In an aspect, at least one of the two plants being crossed is a hybrid tobacco plant. In an aspect, at least one of the two plants being crossed is a modified plant.

In an aspect, a plant of a first variety is the male parent in a crossing step. In an aspect, a plant of a first variety is the female parent in a crossing step. In an aspect, a plant of a second variety is the male parent in a crossing step. In an aspect, a plant of a second variety is the female parent in a crossing step.

Nucleic Acids and Amino Acids

As used herein, "heterologous" refers to a sequence (nucleic acid or amino acid) that originates from a foreign species, or, if from the same species, is substantially modified from its native form in composition and/or genomic locus by deliberate human intervention. The term also is applicable to nucleic acid constructs, also referred to herein as "polynucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest. It will be appreciated that an endogenous promoter can be considered heterologous to an operably linked endogenous gene if the endogenous promoter and endogenous gene are not naturally operably linked (e.g., human intervention is required to put them in operable linkage). As used herein, an "endogenous" nucleic acid sequence refers to a nucleic acid sequence that occurs naturally in the genome of an organism.

In an aspect, a heterologous polynucleotide comprises a gene. In an aspect, a heterologous polynucleotide encodes a small RNA molecule or a precursor thereof. In an aspect, a heterologous polynucleotide encodes a polypeptide.

As used herein, a "gene" refers to a polynucleotide that can produce a functional unit (e.g., without being limiting, for example, a polypeptide, or a small RNA molecule). A gene can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a small RNA molecule or a precursor thereof. In another aspect, a gene encodes a polypeptide.

In an aspect, a gene comprises a nucleic acid sequence at least 80% identical to a nucleic acid sequence selected from the group consisting of SEQ ID NOs: 13-17, 23-30, and 34-36. In an aspect, a gene comprises a nucleic acid sequence at least 85% identical to a nucleic acid sequence selected from the group consisting of SEQ ID NOs: 13-17, 23-30, and 34-36. In an aspect, a gene comprises a nucleic acid sequence at least 90% identical to a nucleic acid sequence selected from the group consisting of SEQ ID NOs: 13-17, 23-30, and 34-36. In an aspect, a gene comprises a nucleic acid sequence at least 92.5% identical to a nucleic acid sequence selected from the group consisting of SEQ ID NOs: 13-17, 23-30, and 34-36. In an aspect, a gene comprises a nucleic acid sequence at least 95% identical to a nucleic acid sequence selected from the group consisting of SEQ ID NOs: 13-17, 23-30, and 34-36. In an aspect, a gene comprises a nucleic acid sequence at least 96% identical to a nucleic acid sequence selected from the group consisting of SEQ ID NOs: 13-17, 23-30, and 34-36. In an aspect, a gene comprises a nucleic acid sequence at least 97% identical to a nucleic acid sequence selected from the group consisting of SEQ ID NOs: 13-17, 23-30, and 34-36. In an aspect, a gene comprises a nucleic acid sequence at least 98% identical to a nucleic acid sequence selected from the group consisting of SEQ ID NOs: 13-17, 23-30, and 34-36. In an aspect, a gene comprises a nucleic acid sequence at least 99% identical to a nucleic acid sequence selected from the group consisting of SEQ ID NOs: 13-17, 23-30, and 34-36. In an aspect, a gene comprises a nucleic acid sequence at least 99.5% identical to a nucleic acid sequence selected from the group consisting of SEQ ID NOs: 13-17, 23-30, and 34-36. In an aspect, a gene comprises a nucleic acid sequence 100% identical to a nucleic acid sequence selected from the group consisting of SEQ ID NOs: 13-17, 23-30, and 34-36.

In an aspect, this disclosure provides a nucleic acid sequence at least 80% identical to a nucleic acid sequence selected from the group consisting of SEQ ID NOs: 13-17, 23-30, and 34-36. In an aspect, this disclosure provides a nucleic acid sequence at least 85% identical to a nucleic acid sequence selected from the group consisting of SEQ ID NOs: 13-17, 23-30, and 34-36. In an aspect, this disclosure provides a nucleic acid sequence at least 90% identical to a nucleic acid sequence selected from the group consisting of SEQ ID NOs: 13-17, 23-30, and 34-36. In an aspect, this disclosure provides a nucleic acid sequence at least 92.5% identical to a nucleic acid sequence selected from the group consisting of SEQ ID NOs: 13-17, 23-30, and 34-36. In an aspect, this disclosure provides a nucleic acid sequence at least 95% identical to a nucleic acid sequence selected from the group consisting of SEQ ID NOs: 13-17, 23-30, and 34-36. In an aspect, this disclosure provides a nucleic acid sequence at least 96% identical to a nucleic acid sequence selected from the group consisting of SEQ ID NOs: 13-17, 23-30, and 34-36. In an aspect, this disclosure provides a nucleic acid sequence at least 97% identical to a nucleic acid sequence selected from the group consisting of SEQ ID NOs: 13-17, 23-30, and 34-36. In an aspect, this disclosure provides a nucleic acid sequence at least 98% identical to a nucleic acid sequence selected from the group consisting of SEQ ID NOs: 13-17, 23-30, and 34-36. In an aspect, this disclosure provides a nucleic acid sequence at least 99% identical to a nucleic acid sequence selected from the group consisting of SEQ ID NOs: 13-17, 23-30, and 34-36. In an aspect, this disclosure provides a nucleic acid sequence at least 99.5% identical to a nucleic acid sequence selected from the group consisting of SEQ ID NOs: 13-17, 23-30, and 34-36. In an aspect, this disclosure provides a nucleic acid sequence 100% identical to a nucleic acid sequence selected from the group consisting of SEQ ID NOs: 13-17, 23-30, and 34-36.

In an aspect, a gene comprises a nucleic acid sequence encoding an amino acid sequence at least 80% identical or similar to an amino acid sequence selected from the group consisting of SEQ ID NOs: 18-22 and 31-33. In an aspect, a gene comprises a nucleic acid sequence encoding an amino acid sequence at least 85% identical or similar to an amino acid sequence selected from the group consisting of SEQ ID NOs: 18-22 and 31-33. In an aspect, a gene comprises a nucleic acid sequence encoding an amino acid sequence at least 90% identical or similar to an amino acid sequence selected from the group consisting of SEQ ID NOs: 18-22 and 31-33. In an aspect, a gene comprises a nucleic acid sequence encoding an amino acid sequence at least 92.5% identical or similar to an amino acid sequence selected from the group consisting of SEQ ID NOs: 18-22 and 31-33. In an aspect, a gene comprises a nucleic acid sequence encoding an amino acid sequence at least 95% identical or similar to an amino acid sequence selected from the group consisting of SEQ ID NOs: 18-22 and 31-33. In an aspect, a gene comprises a nucleic acid sequence encoding an amino acid sequence at least 96% identical or similar to an amino acid sequence selected from the group consisting of SEQ ID NOs: 18-22 and 31-33. In an aspect, a gene comprises a nucleic acid sequence encoding an amino acid sequence at least 97% identical or similar to an amino acid sequence selected from the group consisting of SEQ ID NOs: 18-22 and 31-33. In an aspect, a gene comprises a nucleic acid sequence encoding an amino acid sequence at least 98% identical or similar to an amino acid sequence selected from the group consisting of SEQ ID NOs: 18-22 and 31-33. In an aspect, a gene comprises a nucleic acid sequence encoding an amino acid sequence at least 99% identical or similar to an amino acid sequence selected from the group consisting of SEQ ID NOs: 18-22 and 31-33. In an aspect, a gene comprises a nucleic acid sequence encoding an amino acid sequence at least 99.9% identical or similar to an amino acid sequence selected from the group consisting of SEQ ID NOs: 18-22 and 31-33. In an aspect, a gene comprises a nucleic acid sequence encoding an amino acid sequence 100% identical or similar to an amino acid sequence selected from the group consisting of SEQ ID NOs: 18-22 and 31-33.

In an aspect, this disclosure provides a nucleic acid sequence encoding an amino acid sequence at least 80% identical or similar to an amino acid sequence selected from the group consisting of SEQ ID NOs: 18-22 and 31-33. In an aspect, this disclosure provides a nucleic acid sequence encoding an amino acid sequence at least 85% identical or similar to an amino acid sequence selected from the group consisting of SEQ ID NOs: 18-22 and 31-33. In an aspect, this disclosure provides a nucleic acid sequence encoding an amino acid sequence at least 90% identical or similar to an amino acid sequence selected from the group consisting of SEQ ID NOs: 18-22 and 31-33. In an aspect, this disclosure provides a nucleic acid sequence encoding an amino acid sequence at least 92.5% identical or similar to an amino acid sequence selected from the group consisting of SEQ ID NOs: 18-22 and 31-33. In an aspect, this disclosure provides a nucleic acid sequence encoding an amino acid sequence at least 95% identical or similar to an amino acid sequence selected from the group consisting of SEQ ID NOs: 18-22 and 31-33. In an aspect, this disclosure provides a nucleic acid sequence encoding an amino acid sequence at least 96% identical or similar to an amino acid sequence selected from the group consisting of SEQ ID NOs: 18-22 and 31-33. In an aspect, this disclosure provides a nucleic acid sequence encoding an amino acid sequence at least 97% identical or similar to an amino acid sequence selected from the group consisting of SEQ ID NOs: 18-22 and 31-33. In an aspect, this disclosure provides a nucleic acid sequence encoding an amino acid sequence at least 98% identical or similar to an amino acid sequence selected from the group consisting of SEQ ID NOs: 18-22 and 31-33. In an aspect, this disclosure provides a nucleic acid sequence encoding an amino acid sequence at least 99% identical or similar to an amino acid sequence selected from the group consisting of SEQ ID NOs: 18-22 and 31-33. In an aspect, this disclosure provides a nucleic acid sequence encoding an amino acid sequence at least 99.9% identical or similar to an amino acid sequence selected from the group consisting of SEQ ID NOs: 18-22 and 31-33. In an aspect, this disclosure provides a nucleic acid sequence encoding an amino acid sequence 100% identical or similar to an amino acid sequence selected from the group consisting of SEQ ID NOs: 18-22 and 31-33.

In an aspect, a polypeptide comprises an amino acid sequence at least 80% identical or similar to an amino acid sequence selected from the group consisting of SEQ ID NOs: 18-22 and 31-33. In an aspect, a polypeptide comprises an amino acid sequence at least 85% identical or similar to an amino acid sequence selected from the group consisting of SEQ ID NOs: 18-22 and 31-33. In an aspect, a polypeptide comprises an amino acid sequence at least 90% identical or similar to an amino acid sequence selected from the group consisting of SEQ ID NOs: 18-22 and 31-33. In an aspect, a polypeptide comprises an amino acid sequence at least 92.5% identical or similar to an amino acid sequence selected from the group consisting of SEQ ID NOs: 18-22 and 31-33. In an aspect, a polypeptide comprises an amino acid sequence at least 95% identical or similar to an amino acid sequence selected from the group consisting of SEQ ID NOs: 18-22 and 31-33. In an aspect, a polypeptide comprises an amino acid sequence at least 96% identical or similar to an amino acid sequence selected from the group consisting of SEQ ID NOs: 18-22 and 31-33. In an aspect, a polypeptide comprises an amino acid sequence at least 97% identical or similar to an amino acid sequence selected from the group consisting of SEQ ID NOs: 18-22 and 31-33. In an aspect, a polypeptide comprises an amino acid sequence at least 98% identical or similar to an amino acid sequence selected from the group consisting of SEQ ID NOs: 18-22 and 31-33. In an aspect, a polypeptide comprises an amino acid sequence at least 99% identical or similar to an amino acid sequence selected from the group consisting of SEQ ID NOs: 18-22 and 31-33. In an aspect, a polypeptide comprises an amino acid sequence at least 99.9% identical or similar to an amino acid sequence selected from the group consisting of SEQ ID NOs: 18-22 and 31-33. In an aspect, a polypeptide comprises an amino acid sequence 100% identical or similar to an amino acid sequence selected from the group consisting of SEQ ID NOs: 18-22 and 31-33.

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," Nucleic Acids Research 31:3497-3500 (2003); Thompson et al., "Clustal W: Improving the sensitivity of progressive multiple sequence alignment through sequence weighting, position-specific gap penalties and weight matrix choice," Nucleic Acids Research 22:4673-4680 (1994); Larkin MA et al., "Clustal W and Clustal X version 2.0," Bioinformatics 23:2947-48 (2007); and Altschul et al. "Basic local alignment search tool." J. Mol. Biol. 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. A nucleic acid molecule can encode a polypeptide or a small RNA.

As used herein, a "recombinant nucleic acid molecule" refers to a nucleic acid molecule formed by laboratory methods of genetic recombination, such as, without being limiting, molecular cloning. Similarly, a "recombinant DNA construct" refers to a DNA molecule formed by laboratory methods of genetic recombination.

In an aspect, this disclosure provides a recombinant nucleic acid molecule comprising a promoter operably linked to a heterologous nucleic acid sequence, where the nucleic acid sequence is at least 80% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 85% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 90% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 92.5% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 95% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 96% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 97% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 98% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 99% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous nucleic acid sequence, where the nucleic acid sequence is at least 99.9% identical to a sequence selected from the group consisting of SEQ ID NOs: 13-17, 23-30, and 34-36, or a functional fragment thereof. In an aspect, this disclosure provides a recombinant nucleic acid molecule comprising a promoter operably linked to a heterologous polynucleotide, where nucleic acid sequence 100% identical to a sequence selected from the group consisting of SEQ ID NOs: 13-17, 23-30, and 34-36, or a functional fragment thereof.

In an aspect, this disclosure provides a recombinant nucleic acid molecule comprising a promoter operably linked to a heterologous polynucleotide, where the polynucleotide encodes an amino acid sequence at least 80% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 85% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 90% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 95% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 96% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 97% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 98% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 99% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence at least 99.9% identical or similar to an amino acid sequence selected from the group consisting of SEQ ID NOs: 18-22 and 31-33. In an aspect, this disclosure provides a recombinant nucleic acid molecule comprising a promoter operably linked to a heterologous polynucleotide, where the polynucleotide encodes an amino acid sequence 100% identical or similar to an amino acid sequence selected from the group consisting of SEQ ID NOs: 18-22 and 31-33.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell.

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In an aspect, this disclosure provides a promoter. In an aspect, a promoter is heterologous to an operably linked nucleic acid sequence. As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. In an aspect, a promoter is a tissue-preferred promoter. In an aspect, a tissue-preferred promoter is a leaf tissue-preferred promoter. In an aspect, a tissue-preferred promoter is a flower tissue-preferred promoter such as the promoter of gene that encode anthocyanidin synthase (NtANS1) (Lim et al., Plant Cell Tissue Organ Cult 114 (3): 373-383 (2013)). In an aspect, a tissue-preferred promoter is a root tissue-preferred promoter such as the promoter of extension-like protein (NtREL1) (Zhang et al. Plant Cell Rep 35,757-769 (2016)). In an aspect, a promoter is an epidermal tissue-preferred promoter such as the promoter of gene that encodes lipid transfer protein (Ntltp1) in root epidermis (Canevascini et al., Plant Physiol 112 (2) 513-524 (1996)).

Promoters that drive expression in all or most tissues of the plant are referred to as "constitutive" promoters. In an aspect, a promoter is a constitutive promoter. In an aspect, a constitutive promoter is selected from the group consisting of a Cauliflower Mosaic Virus 35S promoter, a ubiquitin promoter, an actin promoter, an opine promoter, and an alcohol dehydrogenase promoter.

An "inducible" promoter is a promoter that initiates transcription in response to an environmental stimulus such as heat, cold, drought, light, or other stimuli, such as wounding or chemical application. In an aspect, a promoter is an inducible promoter.

In an aspect, a promoter is expressible in a plant cell.

Terpenes

Terpenes are a class of aromatic organic compounds produced by plants and some insects. Terpenes are hydrocarbon molecules that are often used by plants to either directly deter herbivory or to attract predators or parasites of plant herbivores. Non-limiting examples of terpenes include citral, menthol, camphor, salvinorin A, cannabinoids, and curcuminoids.

In an aspect, a terpene is a terpenoid. Terpenoids (also referred to as isoprenoids) are modified terpenes that contain additional functional groups, which can include oxygen. Terpenoids, which can be cyclic or acyclic, vary in size from five-carbon hemiterpenes to long complex molecules containing thousands of isoprene units. Terpenoids are produced through the condensation of five-carbon isoprene units (e.g., dimethylallyl diphosphate (DMAPP) and isopentenyl diphosphate (IPP)), most often by the sequential head-to-tail addition of DMAPP to IPP. The initial cyclization processes are catalyzed by different terpene synthases and enzyme variation leads to variation in monoterpene structure.

Terpenoids are classified according to the number of isoprene units that comprise the parent terpene. A hemiterpenoid comprises one isoprene unit. A monoterpenoid comprises two isoprene units. A sesquiterpenoid comprises three isoprene units. A diterpenoid comprises four isoprene units. A sesterterpenoid comprises five isoprene units. A triterpenoid comprises six isoprene units. A tetraterpenoid comprises eight isoprene units. A polyterpenoid comprises more than eight isoprene units.

In an aspect, a terpene is menthol. In an aspect, a terpene is menthol or a related compound. In an aspect, a terpene is a labdanoid. In an aspect, a terpene is cembratrienediol. In an aspect, a terpene is levopimaric acid. In an aspect, a terpene is L-leucine. In an aspect, a terpene is neophytadiene. In an aspect, a labdanoid is cis-abienol. In an aspect, a terpene is selected from the group consisting of menthol or a related compound, a labdanoid, cembratrienediol, levopimaric acid, and L-leucine. In an aspect, a terpene is selected from the group consisting of menthol or a related compound, a labdanoid, cembratrienediol, levopimaric acid, L-leucine, and neophytadiene. In an aspect, a terpene is selected from the group consisting of menthol, a labdanoid, cembratrienediol, levopimaric acid, and L-leucine. In an aspect, a terpene is selected from the group consisting of menthol, a labdanoid, cembratrienediol, levopimaric acid, L-leucine, and neophytadiene.

As used herein, "menthol" refers to the organic compound having a chemical formula of $C_{10}H_{20}O$ and the International Union of Pure and Applied Chemistry (IUPAC) name 5-Methyl-2-(propan-2-yl) cyclohexan-1-ol. Menthol is also referred to as "(−)-Menthol." Related compounds of menthol include, but are not limited to, (+)-Menthol, (+)-Isomenthol, (+)-Neomenthol, (+)-Neoisomenthol, (−)-Isomenthol, (−)-Neomethol, and (−)-Neoisomenthol. In an aspect, a related compound of menthol is selected from the group consisting of (+)-Menthol, (+)-Isomenthol, (+)-Neomenthol, (+)-Neoisomenthol, (−)-Isomenthol, (−)-Neomethol, and (−)-Neoisomenthol.

As used herein, "neophytadiene" refers to the organic compound having a chemical formula of C20H38 and the IUPAC name of 7, 11,15-trimethyl-3-methylidenehexadec-1-ene.

As used herein, "cembratrienediol" refers to the organic compound having a chemical formula of C20H34O2 and the IUPAC name (1R,3R,4Z,8Z,12S,13Z)-1,5,9-trimethyl-12-propan-2-ylcyclotetradeca-4,8,13-triene-1,3-diol. Cembratrienediol is also referred to as "beta-Cembrenediol."

As used herein, "levopimaric acid" refers to the organic compound having a chemical formula of C20H30O2 and the IUPAC name (1R,4aR,4bS,10aR)-1,4a-dimethyl-7-propan-2-yl-2,3,4,4b,5,9,10,10a-octahydrophenanthrene-1-carboxylic acid. Levopimaric acid is also referred to as "L-Pimaric acid."

As used herein, "L-leucine" refers to the amino acid having the chemical formula C6H12NO2 and the IUPAC name (2S)-2-amino-4-methylpentanoic acid.

As used herein, a "labdanoid" refers to a terpenoid derivative of the fundamental parent labdane, a diterpene. A labdane has the chemical formula C20H38 and the IUPAC name (1S,2S,4aS,8aR)-2,5,5,8a-tetramethyl-1-[(3R)-3-methylpentyl]-1,2,3,4,4a,6,7,8-octahydronaphthalene.

A non-limiting example of a labdanoid is cis-abienol. As used herein, "cis-abienol" refers to the organic compound having a chemical formula of C20H34O and the IUPAC name (1R,2R,4aS,8aS)-2,5,5,8a-tetramethyl-1-[(2Z)-3-methylpenta-2,4,-dienyl]-3,4,4a,6,7,8-hexahydro-1H-naphthalen-2-ol.

In an aspect, a modified plant, seed, or plant part comprising a recombinant nucleic acid provided herein comprises an increased amount of at least one terpene as compared to a control plant, seed, or plant part lacking the recombinant nucleic acid molecule when grown under comparable conditions. In an aspect, a modified tobacco plant, tobacco seed, or tobacco plant part comprising a recombinant nucleic acid provided herein comprises an increased amount of at least one terpene as compared to a control tobacco plant, tobacco seed, or tobacco plant part lacking the recombinant nucleic acid molecule when grown under comparable conditions. In an aspect, a modified *cannabis* plant, *cannabis* seed, or *cannabis* plant part comprising a recombinant nucleic acid provided herein comprises an increased amount of at least one terpene as compared to a control *cannabis* plant, *cannabis* seed, or *cannabis* plant part lacking the recombinant nucleic acid molecule when grown under comparable conditions.

In an aspect, an increased amount of at least one terpene comprises an increase of at least 0.5%. In an aspect, an increased amount of at least one terpene comprises an increase of at least 1%. In an aspect, an increased amount of at least one terpene comprises an increase of at least 2%. In an aspect, an increased amount of at least one terpene comprises an increase of at least 3%. In an aspect, an increased amount of at least one terpene comprises an increase of at least 4%. In an aspect, an increased amount of at least one terpene comprises an increase of at least 5%. In an aspect, an increased amount of at least one terpene comprises an increase of at least 10%. In an aspect, an increased amount of at least one terpene comprises an increase of at least 12.5%. In an aspect, an increased amount of at least one terpene comprises an increase of at least 15%. In an aspect, an increased amount of at least one terpene comprises an increase of at least 17.5%. In an aspect, an increased amount of at least one terpene comprises an increase of at least 20%. In an aspect, an increased amount of at least one terpene comprises an increase of at least 25%. In an aspect, an increased amount of at least one terpene comprises an increase of at least 30%. In an aspect, an increased amount of at least one terpene comprises an increase of at least 40%. In an aspect, an increased amount of at least one terpene comprises an increase of at least 50%. In an aspect, an increased amount of at least one terpene comprises an increase of at least 60%. In an aspect, an increased amount of at least one terpene comprises an increase of at least 70%. In an aspect, an increased amount of at least one terpene comprises an increase of at least 80%. In an aspect, an increased amount of at least one terpene comprises an increase of at least 90%. In an aspect, an increased amount of at least one terpene comprises an increase of at least 100%. In an aspect, an increased amount of at least one terpene comprises an increase of at least 150%. In an aspect, an increased amount of at least one terpene comprises an increase of at least 200%. In an aspect, an increased amount of at least one terpene comprises an increase of at least 250%. In an aspect, an increased amount of at least one terpene comprises an increase of at least 500%.

In an aspect, an increased amount of at least one terpene comprises an increase of between 0.5% and 500%. In an aspect, an increased amount of at least one terpene comprises an increase of between 0.5% and 250%. In an aspect, an increased amount of at least one terpene comprises an increase of between 0.5% and 100%. In an aspect, an increased amount of at least one terpene comprises an increase of between 0.5% and 75%. In an aspect, an increased amount of at least one terpene comprises an increase of between 0.5% and 50%. In an aspect, an increased amount of at least one terpene comprises an increase of between 0.5% and 25%. In an aspect, an increased amount of at least one terpene comprises an increase of between 0.5% and 10%. In an aspect, an increased amount of at least one terpene comprises an increase of between 0.5% and 5%. In an aspect, an increased amount of at least one terpene comprises an increase of between 0.5% and 500%. In an aspect, an increased amount of at least one terpene comprises an increase of between 5% and 250%. In an aspect, an increased amount of at least one terpene comprises an increase of between 5% and 100%. In an aspect, an increased amount of at least one terpene comprises an increase of between 5% and 50%. In an aspect, an increased amount of at least one terpene comprises an increase of between 25% and 500%. In an aspect, an increased amount of at least one terpene comprises an increase of between 25% and 250%. In an aspect, an increased amount of at least one terpene comprises an increase of between 50% and 100%. In an aspect, an increased amount of at least one terpene comprises an increase of between 100% and 500%.

The amount of terpenes in a plant can be measured using any method known in the art, including, without being limiting, gas chromatography mass spectrometry (GC-MS), Nuclear Magnetic Resonance Spectroscopy, and liquid chromatography-linked mass spectrometry. See The Handbook of Plant Metabolomics, edited by Weckwerth and Kahl, (Wiley-Blackwell) (May 28, 2013). In an aspect, an amount of at least one terpene refers to the concentration of the at least one terpene in the tissue sampled.

Products

In an aspect, this disclosure provides cured plant material from any plant or plant part provided herein. In an aspect, this disclosure provides cured tobacco material from any tobacco plant or tobacco plant part provided herein.

In an aspect, cured plant material is made by a curing process selected from the group consisting of flue curing, air curing, fire curing, and sun curing. In an aspect, cured tobacco material is made by a curing process selected from the group consisting of flue curing, air curing, fire curing, and sun curing.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, (e.g., flue-cured, barn-cured, fire-cured, air-cured or sun-cured). See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation.

Information regarding the harvesting of burley and dark tobacco varieties can be found in the 2019-2020 Burley and Dark Tobacco Production Guide (December 2018) published by the University of Kentucky, The University of Tennessee, Virginia Tech, and North Carolina State University, which is incorporated herein by reference in its entirety.

In an aspect, cured tobacco material comprises tobacco material selected from the group selected from cured leaf material, cured stem material, cured bud material, cured flower material, and cured root material. In an aspect, cured tobacco material comprises cured leaf material, cured stem material, or both. In an aspect, cured tobacco material comprises cured leaf material. In an aspect, cured tobacco material comprises cured stem material.

In an aspect, cured tobacco material comprises flue-cured tobacco material. In an aspect, cured tobacco material comprises air-cured tobacco material. In an aspect, cured tobacco material comprises fire-cured tobacco material. In an aspect, cured tobacco material comprises sun-cured tobacco material. In an aspect, cured tobacco material provided herein is selected from the group consisting of air-cured tobacco material, fire-cured tobacco material, sun-cured tobacco material, and flue-cured tobacco material. In an aspect, cured tobacco material is from a tobacco variety selected from the group consisting of a flue-cured variety, a bright variety, a Burley variety, a Virginia variety, a Maryland variety, a dark variety, an Oriental variety, and a Turkish variety.

In an aspect, cured tobacco leaf provided herein is selected from the group consisting of air-cured tobacco leaf, fire-cured tobacco leaf, sun-cured tobacco leaf, and flue-cured tobacco leaf. In an aspect, cured tobacco leaf is from a tobacco variety selected from the group consisting of a flue-cured variety, a bright variety, a Burley variety, a Virginia variety, a Maryland variety, a dark variety, an Oriental variety, and a Turkish variety.

Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In an aspect, this disclosure provides fermented tobacco material from any tobacco plant, or part thereof, provided herein. In another aspect, this disclosure provides fermented tobacco material from any modified tobacco plant, or part thereof, provided herein.

Tobacco material obtained from the tobacco lines, varieties or hybrids of the present disclosure can be used to make tobacco products. As used herein, "tobacco product" is defined as any product made or derived from tobacco that is intended for human use or consumption. In an aspect, this disclosure provides a tobacco product comprising plant material from a tobacco plant provided herein. In another aspect, this disclosure provides a tobacco product comprising plant material from a modified tobacco plant provided herein. In another aspect, this disclosure provides a tobacco product comprising cured tobacco material. In another aspect, this disclosure provides a tobacco product comprising fermented tobacco material. In another aspect, this disclosure provides a tobacco product comprising a tobacco blend.

Tobacco products include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In an aspect, a tobacco product comprises reconstituted tobacco. In another aspect, this disclosure provides reconstituted tobacco comprising cured tobacco material. As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

In an aspect, a tobacco product comprises expanded tobacco. As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a kretek, a bidi cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco.

In an aspect, a tobacco product of the present disclosure is selected from the group consisting of a cigarette, a heated tobacco product, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

In an aspect, a tobacco product of the present disclosure is a smokeless tobacco product. In an aspect, a smokeless tobacco product is selected from the group consisting of loose leaf chewing tobacco, plug chewing tobacco, moist snuff, nasal snuff, dry snuff, and snus.

Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat-treated smokeless tobacco. Dry snuff is finely ground tobacco that is placed in the mouth or used nasally.

In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product.

In another aspect, this disclosure provides a tobacco blend comprising cured tobacco material. A tobacco blend can comprise any combination of cured tobacco, uncured tobacco, fermented tobacco, unfermented tobacco, expanded tobacco, and reconstituted tobacco.

In an aspect, a tobacco blend comprises at least 5% cured tobacco by weight. In an aspect, a tobacco blend comprises at least 10% cured tobacco by weight. In an aspect, a tobacco blend comprises at least 15% cured tobacco by weight. In an aspect, a tobacco blend comprises at least 20% cured tobacco by weight. In an aspect, a tobacco blend comprises at least 25% cured tobacco by weight. In an aspect, a tobacco blend comprises at least 30% cured tobacco by weight. In an aspect, a tobacco blend comprises at least 35% cured tobacco by weight. In an aspect, a tobacco blend comprises at least 40% cured tobacco by weight. In an aspect, a tobacco blend comprises at least 45% cured tobacco by weight. In an aspect, a tobacco blend comprises at least 50% cured tobacco by weight. In an aspect, a tobacco blend comprises at least 55% cured tobacco by weight. In an aspect, a tobacco blend comprises at least 60% cured tobacco by weight. In an aspect, a tobacco blend comprises at least 65% cured tobacco by weight. In an aspect, a tobacco blend comprises at least 70% cured tobacco by weight. In an aspect, a tobacco blend comprises at least 75% cured tobacco by weight. In an aspect, a tobacco blend comprises at least 80% cured tobacco by weight. In an aspect, a tobacco blend comprises at least 85% cured tobacco by weight. In an aspect, a tobacco blend comprises at least 90% cured tobacco by weight. In an aspect, a tobacco blend comprises at least 95% cured tobacco by weight.

In an aspect, a tobacco blend comprises at least 5% cured tobacco by volume. In an aspect, a tobacco blend comprises at least 10% cured tobacco by volume. In an aspect, a tobacco blend comprises at least 15% cured tobacco by volume. In an aspect, a tobacco blend comprises at least 20% cured tobacco by volume. In an aspect, a tobacco blend comprises at least 25% cured tobacco by volume. In an aspect, a tobacco blend comprises at least 30% cured tobacco by volume. In an aspect, a tobacco blend comprises at least 35% cured tobacco by volume. In an aspect, a tobacco blend comprises at least 40% cured tobacco by volume. In an aspect, a tobacco blend comprises at least 45% cured tobacco by volume. In an aspect, a tobacco blend comprises at least 50% cured tobacco by volume. In an aspect, a tobacco blend comprises at least 55% cured tobacco by volume. In an aspect, a tobacco blend comprises at least 60% cured tobacco by volume. In an aspect, a tobacco blend comprises at least 65% cured tobacco by volume. In an aspect, a tobacco blend comprises at least 70% cured tobacco by volume. In an aspect, a tobacco blend comprises at least 75% cured tobacco by volume. In an aspect, a tobacco blend comprises at least 80% cured tobacco by volume. In an aspect, a tobacco blend comprises at least 85% cured tobacco by volume. In an aspect, a tobacco blend comprises at least 90% cured tobacco by volume. In an aspect, a tobacco blend comprises at least 95% cured tobacco by volume.

In an aspect, this disclosure provides a *cannabis* product comprising material from a *cannabis* plant, *cannabis* seed, or *cannabis* plant part provided herein. In an aspect, a *cannabis* product is a smokeless product. In a further aspect, a smokeless *cannabis* product is an edible *cannabis* product. In a further aspect, a smokeless *cannabis* product is a fiber based product. In an aspect, a *cannabis* product is a smokable product. In an aspect, a *cannabis* product is derived from *cannabis* biomass. In an aspect, a *cannabis* product is a distillate derived from *cannabis* biomass.

In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 80% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 85% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 90% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 92.5% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 95% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 96% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 97% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 98% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 99% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence is at least 99.9% identical to a sequence selected from the group consisting of SEQ ID NOs: 13-17, 23-30, and 34-36, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous polynucleotide, where the nucleic acid sequence is selected from the group consisting of SEQ ID NOs: 13-17, 23-30, and 34-36, or a functional fragment thereof.

In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 80% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 85% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 90% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 92.5% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 95% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 96% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 97% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 98% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 99% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence at least 99.9% identical or similar to a sequence selected from the group consisting of SEQ ID NOs: 18-22 and 31-33, or a functional fragment thereof. In an aspect, this disclosure provides a method comprising preparing a tobacco product producing using cured tobacco material from a modified tobacco plant or part therefrom, where the modified tobacco plant or part therefrom comprises a recombinant nucleic acid molecule comprising a promoter operably linked to a heterologous nucleic acid sequence, where the nucleic acid sequence encodes an amino acid sequence selected from the group consisting of SEQ ID NOs: 18-22 and 31-33, or a functional fragment thereof.

In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 80% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 85% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 90% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 92.5% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 95% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 96% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 97% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 98% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 99% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence is at least 99.9% identical to a sequence selected from the group consisting of SEQ ID NOs: 13-17, 23-30, and 34-36, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous polynucleotide, where nucleic acid sequence 100% identical to a sequence selected from the group consisting of SEQ ID NOs: 13-17, 23-30, and 34-36, or a functional fragment thereof.

In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 80% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 85% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 90% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 92.5% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 95% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 96% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 97% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 98% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 99% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence at least 99.9% identical or similar to a sequence selected from the group consisting of SEQ ID NOs: 18-22 and 31-33, or a functional fragment thereof. In an aspect, this disclosure provides a method comprising preparing a *cannabis* product using material from a modified *cannabis* plant or part therefrom, where the modified *cannabis* plant or part therefrom comprises a recombinant nucleic acid molecule comprising a promoter operably linked to a heterologous nucleic acid sequence, where the nucleic acid sequence encodes an amino acid sequence selected from the group consisting of SEQ ID NOs: 18-22 and 31-33, or a functional fragment thereof.

Transformation

In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 80% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 85% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 90% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 92.5% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 95% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 96% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 97% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 98% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 99% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is at least 99.9% identical to a sequence selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence is selected from the group consisting of SEQ ID NOs: 13-17, 23-30, and 34-36, or a functional fragment thereof; (b) selecting at least one plant cell from step (a), where the at least one plant cell comprises the recombinant nucleic acid molecule; and (c) regenerating a modified plant from the at least one plant cell selected in step (b).

In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 80% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 85% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 90% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 92.5% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 95% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 96% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 97% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 98% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 99% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence is at least 99.9% identical to a sequence selected from the group consisting of SEQ ID NOs: 13-17, 23-30, and 34-36, or a functional fragment thereof. In an aspect, a method provided herein comprises transforming a plant cell with a recombinant nucleic acid molecule, where the recombinant nucleic acid molecule comprises a promoter operably linked to a heterologous polynucleotide, where nucleic acid sequence 100% identical to a sequence selected from the group consisting of SEQ ID NOs: 13-17, 23-30, and 34-36, or a functional fragment thereof.

In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 80% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 85% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 90% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 92.5% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 95% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 96% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 97% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 98% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 99% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where the nucleic acid sequence encodes an amino acid sequence at least 99.9% identical or similar to a sequence selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b). In an aspect, this disclosure provides a method of generating a modified plant, the method comprising: (a) introducing a recombinant nucleic acid molecule comprising a promoter operably linked to a heterologous nucleic acid sequence to at least one plant cell, where nucleic acid sequence encodes a protein selected from the group consisting of SEQ ID NOs: 18-22 and 31-33, or a functional fragment thereof; (b) selecting at least one plant cell from step (a), where the at least one plant cell comprises the recombinant nucleic acid molecule; and (c) regenerating a modified plant from the at least one plant cell selected in step (b).

In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 80% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 85% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 90% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 92.5% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 95% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 96% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 97% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 98% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 99% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence at least 99.9% identical or similar to a sequence selected from the group consisting of SEQ ID NOs: 18-22 and 31-33, or a functional fragment thereof. In an aspect, a method provided herein comprises transforming a plant cell with a recombinant nucleic acid molecule, where the recombinant nucleic acid molecule comprises a promoter operably linked to a heterologous nucleic acid sequence, where the nucleic acid sequence encodes an amino acid sequence selected from the group consisting of SEQ ID NOs: 18-22 and 31-33, or a functional fragment thereof.

Numerous methods for "introducing" a recombinant nucleic acid molecule to a plant cell are known in the art, which can be used according to methods of the present application to produce a modified plant cell, plant, seed, or plant part. As used herein, the terms "introducing" and "transforming" can be used interchangeably. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, polyethylene glycol (PEG)-mediated transformation, etc., are also known in the art. Modified plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell (e.g., tobacco cell, *cannabis* cell) with any of the nucleic acid molecules provided herein.

In an aspect, a method of introducing a recombinant nucleic acid molecule to a plant cell comprises *Agrobacterium*-mediated transformation. In another aspect, a method of introducing a recombinant nucleic acid molecule to a plant cell comprises PEG-mediated transformation. In another aspect, a method of introducing a recombinant nucleic acid molecule to a plant cell comprises biolistic transformation. In another aspect, a method of introducing a recombinant nucleic acid molecule to a plant cell comprises liposome-mediated transfection (lipofection). In another aspect, a method of introducing a recombinant nucleic acid molecule to a plant cell comprises lentiviral transfection.

Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of WO 91/17424 and WO 91/16024. Delivery can be to cells (e.g. in vitro or ex vivo administration) or target tissues (e.g. in vivo administration).

Any plant cell from which a fertile plant can be regenerated is contemplated as a useful recipient cell for practice of this disclosure.

In an aspect, a recombinant nucleic acid molecule is introduced to a tobacco cell. In an aspect, a recombinant nucleic acid molecule is introduced to a tobacco protoplast cell. In another aspect, a recombinant nucleic acid molecule is introduced to a tobacco callus cell. In an aspect, a recombinant nucleic acid molecule is introduced to a tobacco cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

In an aspect, a recombinant nucleic acid molecule is introduced to a *cannabis* cell. In an aspect, a recombinant nucleic acid molecule is introduced to a *cannabis* protoplast cell. In another aspect, a recombinant nucleic acid molecule is introduced to a *cannabis* callus cell. In an aspect, a recombinant nucleic acid molecule is introduced to a *cannabis* cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232, 526 and U. S. Patent Application Publication 2004/0216189, all of which are incorporated herein by reference.

Embodiments

The following examples of non-limiting embodiments are envisioned:
1. A modified plant, seed, or plant part, comprising a recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.
2. The modified plant, seed, or plant part, of embodiment 1, wherein said nucleic acid sequence comprises a sequence at least 90% identical or similar to a sequence selected from the group consisting of SEQ ID NOs: 13-17, 23-30, and 34-36.
3. The modified plant, seed, or plant part, of embodiment 1 or 2, wherein said nucleic acid sequence is at least 95% identical to a sequence selected from the group consisting of SEQ ID NOs: 13-17, 23-30, and 34-36.
4. The modified plant, seed, or plant part, of any one of embodiments 1-3, wherein said nucleic acid sequence encodes a protein at least 90% identical or similar to a sequence selected from the group consisting of SEQ ID NOs: 18-22 and 31-33.
5. The modified plant, seed, or plant part, of any one of embodiments 1-4, wherein said nucleic acid sequence is selected from the group consisting of SEQ ID NOs: 13-17, 23-30, and 34-36.
6. The modified plant, seed, or plant part, of any one of embodiments 1-5, wherein said amino acid sequence is selected from the group consisting of SEQ ID NOs: 18-22 and 31-33.
7. The modified plant, seed, or part thereof of any one of embodiments 1-6, wherein said modified plant, seed, or plant part is a tobacco plant, tobacco seed, or tobacco plant part.
8. The modified plant, seed, or part thereof of embodiment 7, wherein the tobacco plant, tobacco seed, or plant part is of a tobacco variety selected from the group consisting of a flue-cured variety, a bright variety, a Burley variety, a Virginia variety, a Maryland variety, a dark variety, a Galpão variety, an Oriental variety, and a Turkish variety.
9. The modified plant, seed, or part thereof of any one of embodiments 1-8, wherein the plant is male sterile or cytoplasmically male sterile.
10. The modified plant, seed, or part thereof of any one of embodiments 1-6, wherein said modified plant, seed, or plant part is a *cannabis* plant, *cannabis* seed, or *cannabis* plant part.
11. The modified plant, seed, or plant part, of any one of embodiments 1-10, wherein said plant or plant part comprises an amount of at least one terpene that is increased by at least 5% as compared to a control plant lacking said recombinant nucleic acid molecule.
12. The modified plant, seed, or plant part, of any one of embodiments 1-11, wherein the heterologous promoter is selected from the group consisting of a constitutive promoter, an inducible promoter, and a tissue-preferred or tissue-specific promoter.
13. The modified plant, seed, or plant part of any one of embodiments 1-12, wherein at least one leaf of the modified plant comprises a greater average trichome density as compared to a leaf of a control plant grown under comparable conditions.
14. The modified plant, seed, or plant part of any one of embodiments 1-12, wherein at least one leaf of the modified plant comprises a greater average trichome density on the abaxial side of the leaf as compared to the abaxial side of a leaf of a control plant grown under comparable conditions.
15. The modified plant, seed, or plant part of any one of embodiments 1-12, wherein at least one leaf of the modified plant comprises a greater average trichome density on the adaxial side of the leaf as compared to the adaxial side of a leaf of a control plant grown under comparable conditions.
16. Cured tobacco material from a modified tobacco plant or tobacco plant part comprising a recombinant nucleic acid molecule comprising a nucleic acid sequence at encoding an amino acid sequence least 80% identical or similar to an amino acid sequence selected from the group consisting of SEQ ID NOs: 18-22 and 31-33, wherein said nucleic acid sequence is operably linked to a heterologous promoter.
17. The cured tobacco material of embodiment 16, wherein the cured tobacco material is selected from the group consisting of flue cured tobacco material, air cured tobacco material, fire cured tobacco material, and sun cured tobacco material.
18. A tobacco product comprising the cured tobacco material of embodiment 16.
19. The tobacco product of embodiment 18 or 23, wherein the tobacco product is selected from the group consisting of a kretek, a bidi cigarette, a cigarillo, a non-ventilated recess filter cigarette, a vented recess filter cigarette, a cigar, pipe tobacco, cigar tobacco, cigarette tobacco, chewing tobacco, moist snuff, nasal snuff, dry snuff, snus, leaf tobacco, hookah tobacco, shredded tobacco, and cut tobacco.
20. The tobacco product of embodiment 19, wherein the tobacco product is a smokeless tobacco product.
21. The tobacco product of embodiment 20, wherein the smokeless tobacco product is selected from the group consisting of loose leaf chewing tobacco, plug chewing tobacco, moist snuff, nasal snuff, dry snuff, and snus.
22. A reconstituted tobacco comprising the cured tobacco material of embodiment 16.
23. A tobacco product comprising material from a modified tobacco plant, tobacco seed, or tobacco plant part comprising a recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.
24. A *cannabis* product comprising material from a modified *cannabis* plant, *cannabis* seed, or *cannabis* plant part comprising a recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.
25. A recombinant nucleic acid molecule comprising a nucleic acid sequence encoding an amino acid sequence at least 80% identical or similar to an amino acid sequence selected from the group consisting of SEQ ID NOs: 18-22 and 31-33, wherein said nucleic acid sequence is operably linked to a heterologous promoter.

26. The recombinant nucleic acid molecule of embodiment 25, wherein said nucleic acid sequence encodes a protein at least 90% identical or similar to a sequence selected from the group consisting of SEQ ID NOs: 18-22 and 31-33.

27. The recombinant nucleic acid molecule of embodiment 25 or 26, wherein said nucleic acid sequence is at least 90% identical to a sequence selected from the group consisting of SEQ ID NOs: 13-17, 23-30, and 34-36.

28. The recombinant nucleic acid molecule of any one of embodiments 25-27, wherein said nucleic acid sequence encodes a protein at least 95% identical or similar to a sequence selected from the group consisting of SEQ ID NOs: 18-22 and 31-33.

29. The recombinant nucleic acid molecule of any one of embodiments 25-28, wherein said nucleic acid sequence is selected from the group consisting of SEQ ID NOs: 13-17, 23-30, and 34-36.

30. The recombinant nucleic acid molecule of any one of embodiments 25-29, wherein said nucleic acid sequence encodes a protein selected from the group consisting of SEQ ID NOs: 18-22 and 31-33.

31. A method for producing a plant, the method comprising:
   (a) obtaining at least one plant comprising a recombinant nucleic acid molecule comprising a nucleic acid sequence at least 80% identical to a sequence selected from the group consisting of SEQ ID NOs: 13-17, 23-30, and 34-36, wherein said nucleic acid sequence is operably linked to a heterologous promoter;
   (b) crossing said at least one plant with at least one plant of a second variety to produce at least one progeny seed; and
   (c) selecting said at least one progeny seed produced in step (b), or a plant germinated therefrom, wherein said at least one progeny seed or plant germinated therefrom comprises said recombinant nucleic acid molecule.

32. The method of embodiment 31, further comprising
   (d) harvesting plant material from a plant germinated from said at least one progeny seed; and
   (e) producing a product comprising of or derived from said harvested plant material.

33. The method of embodiment 31 or 32, wherein a plant grown from said at least one progeny seed further comprises an amount of at least one terpene that is increased by at least 5% as compared to a control plant lacking said recombinant nucleic acid molecule.

34. The method of any one of embodiments 31-33, wherein a plant grown from said at least one progeny seed further comprises an amount of at least one terpene that is increased by at least 10% as compared to a control plant lacking said recombinant nucleic acid molecule.

35. The method of any one of embodiments 31-34, wherein said at least one plant is from a genus selected from the group consisting of *Nicotiana* and *Cannabis*.

36. The method of any one of embodiments 31-35, wherein said at least one plant is from a genus selected from the group consisting of tobacco and *cannabis*.

37. The method of any one of embodiments 31-36, wherein said a recombinant nucleic acid molecule comprises a nucleic acid sequence encoding a protein at least 80% identical or similar to a sequence selected from the group consisting of SEQ ID NOs: 18-22 and 31-33.

38. The method of any one of embodiments 31-37, wherein said a recombinant nucleic acid molecule comprises a nucleic acid sequence at least 90% identical to a sequence selected from the group consisting of SEQ ID NOs: 13-27 and 34-36.

39. The method of any one of embodiments 31-38, wherein said a recombinant nucleic acid molecule comprises a nucleic acid sequence encoding a protein at least 90% identical or similar to a sequence selected from the group consisting of SEQ ID NOs: 18-22 and 31-33.

40. The method of any one of embodiments 31-39, wherein said a recombinant nucleic acid molecule comprises a nucleic acid sequence selected from the group consisting of SEQ ID NOs: 13-27 and 34-36.

41. The method of any one of embodiments 31-40, wherein said a recombinant nucleic acid molecule comprises a nucleic acid sequence encoding a protein selected from the group consisting of SEQ ID NOs: 18-22 and 31-33.

42. A method of generating a modified plant, the method comprising:
   (a) introducing a recombinant nucleic acid molecule comprising a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell;
   (b) selecting at least one plant cell from step (a), wherein the at least one plant cell comprises the recombinant nucleic acid molecule; and
   (c) regenerating a modified plant from the at least one plant cell selected in step (b).

43. A method comprising preparing a tobacco product using cured tobacco material from a modified tobacco plant or part therefrom, wherein the modified tobacco plant or part therefrom comprises a recombinant nucleic acid molecule comprises a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell.

44. A method comprising preparing a *cannabis* product using material from a modified *cannabis* plant or part therefrom, wherein the modified *cannabis* plant or part therefrom comprises a recombinant nucleic acid molecule comprises a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell.

45. A method comprising transforming a plant cell with a recombinant nucleic acid molecule, wherein the recombinant nucleic acid molecule comprises a nucleic acid sequence at least 80% identical to a sequence selected from the group consisting of SEQ ID NOs: 13-17, 23-30, and 34-36, wherein said nucleic acid sequence is operably linked to a heterologous promoter, to at least one plant cell.

46. A method for producing a plant with increased trichome density, the method comprising:
  (a) providing to at least one plant cell a recombinant nucleic acid comprising a heterologous promoter operably linked to a polynucleotide, where the polynucleotide encodes an amino acid sequence at least 80% identical or similar to an amino acid sequence selected from the group consisting of SEQ ID NOs: 18-22 and 31-33; and
  (b) regenerating a modified plant from the at least one plant cell in step (a), where the modified plant comprises an increased trichome density on at least one leaf as compared to a leaf from a control plant lacking the recombinant nucleic acid when grown under comparable conditions.

Having now generally described the disclosure, the same will be more readily understood through reference to the following examples that are provided by way of illustration, and are not intended to be limiting of the present disclosure, unless specified.

EXAMPLES

Figures 3, 3A:
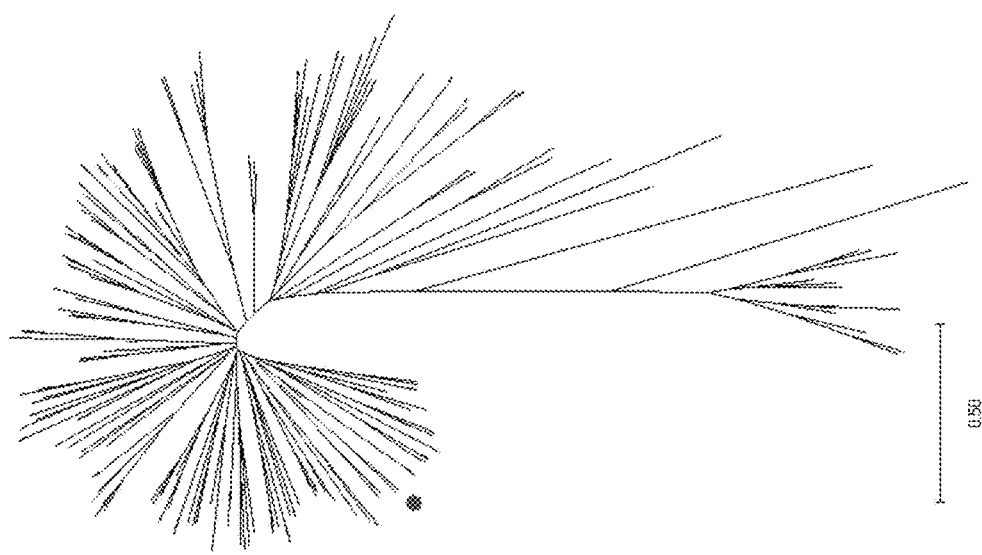
FIG. 3 comprises panels FIG. 3A and FIG. 3B.
FIG. 3A depicts a phylogenetic analysis of the DNA-binding domain of the MYB transcription factor family in tobacco plants (N=319).
Figures 3, 3B:
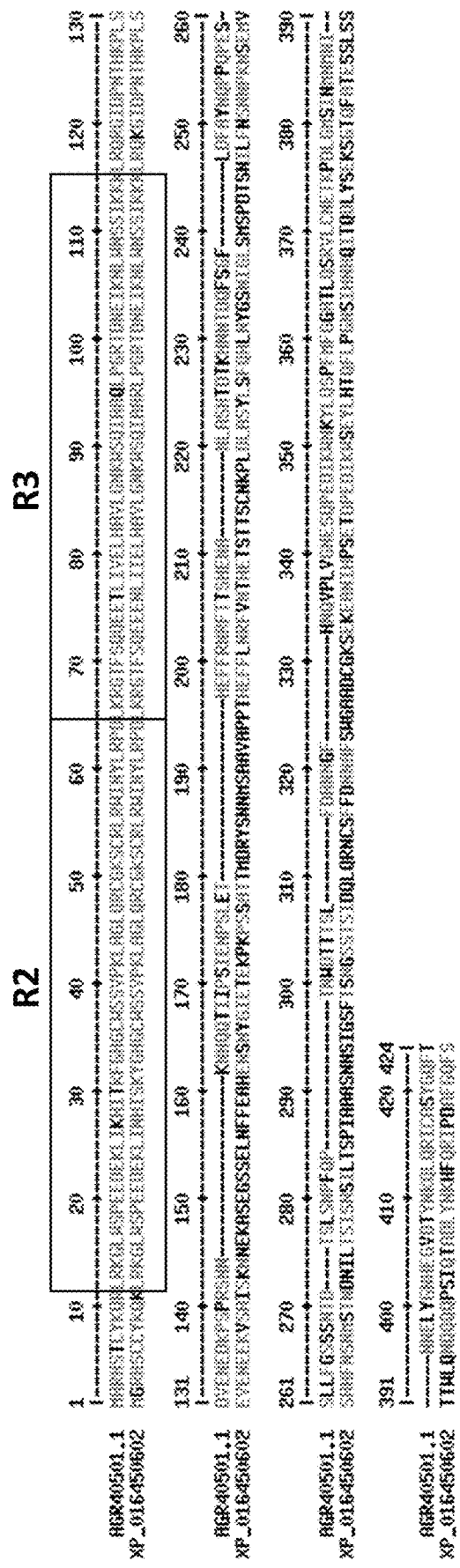
FIG. 3B depicts protein sequence pairwise alignment of the tobacco MYB86 gene (SEQ ID NO: 18, XP_016450602) and sweet wormwood (*Artemisia annua*) MYB (SEQ ID NO: 38, AGR40501.1), highlighting the R2 and R3 DNA-binding domains (enclosed in boxes) specifically. The filled circle indicates MYB86 on the cladogram. The scale bar in FIG. 3A represents evolutionary distance used to infer the phylogenetic tree.
Figure 4:
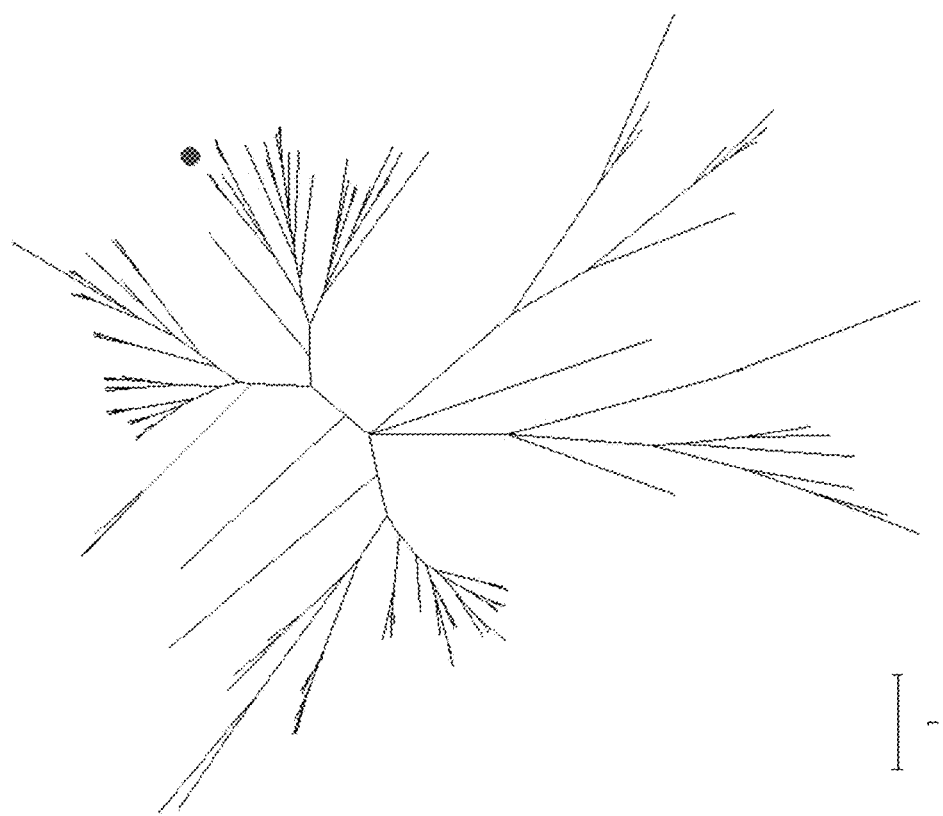
FIG. 4 depicts a phylogenetic analysis of the Glabrous Inflorescence Stems (GIS) family of C2H2 transcription factors in tobacco plants (N=247). The filled circle indicates NtGIS gene (SEQ ID NO: 19) on the cladogram. The scale bar represents evolutionary distance used to infer the phylogenetic tree.
Figures 8, 8A:
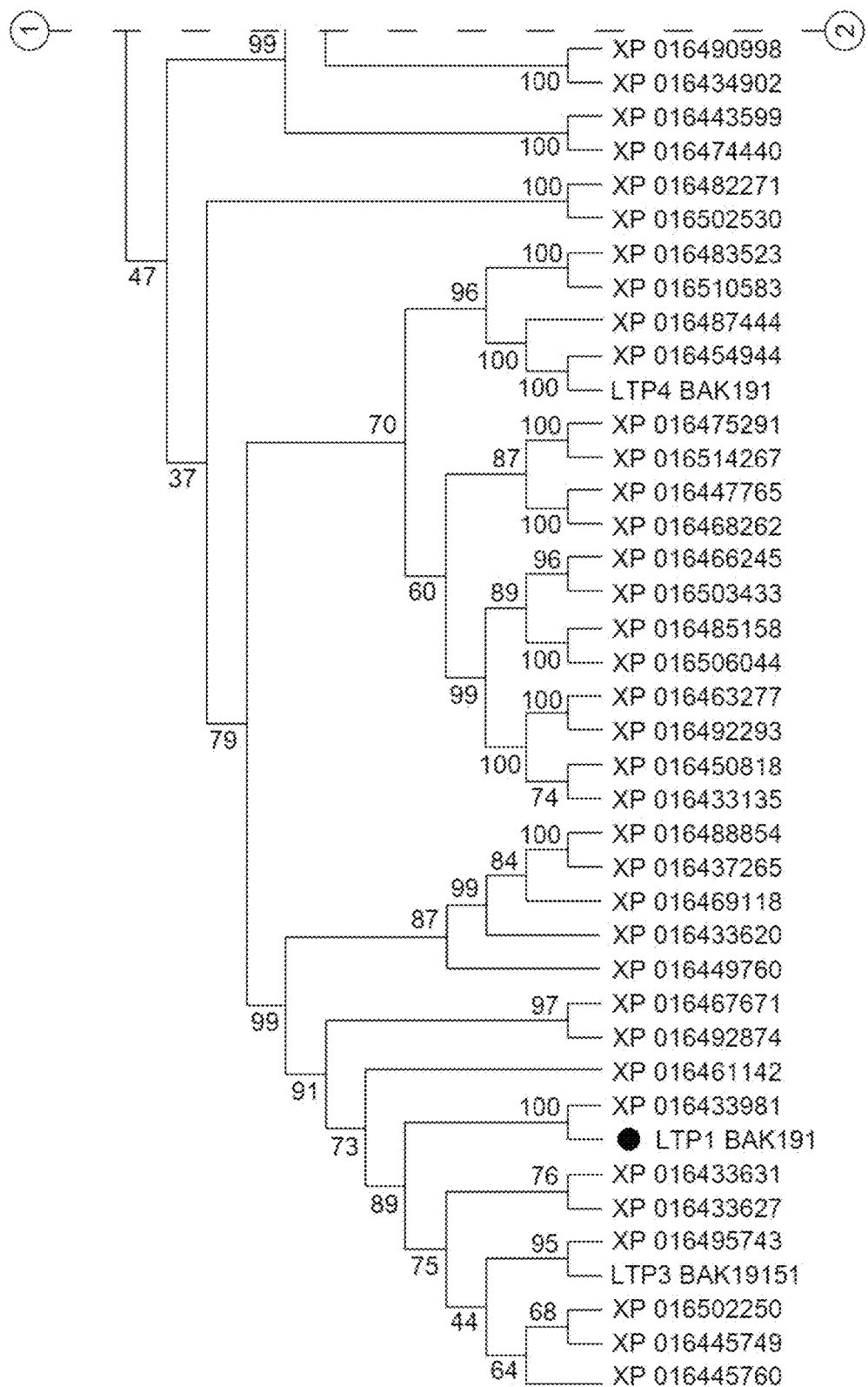
FIG. 8 comprises panels FIG. 8A and FIG. 8B.
FIG. 8A depicts a phylogenetic analysis of the LTP gene family, and the position of the NtLTP1 gene is marked by a filled circle. Publicly available GenBank Accession numbers are provided for each LTP gene family member.
Figures 8, 8A:
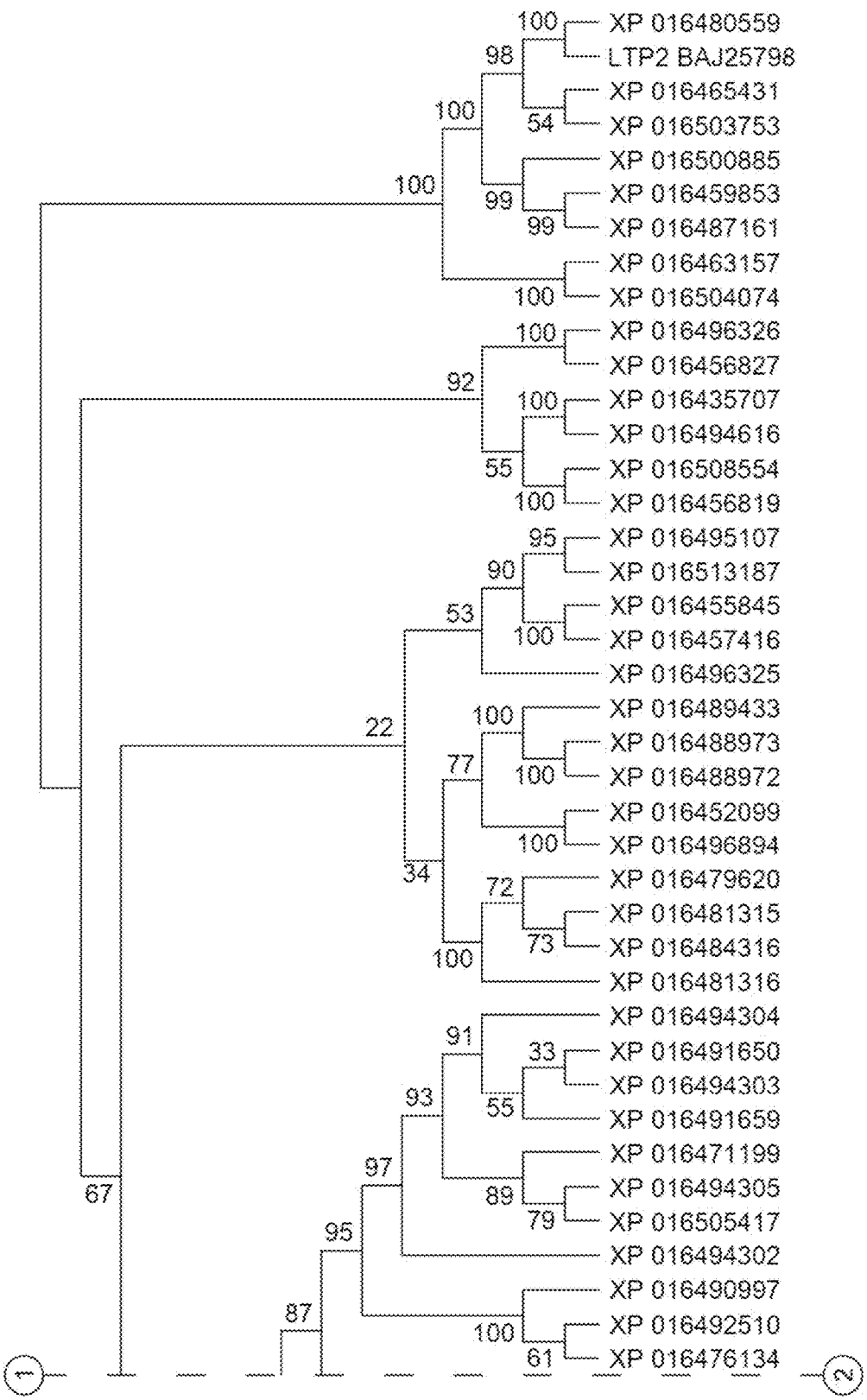
Figures 8, 8B:
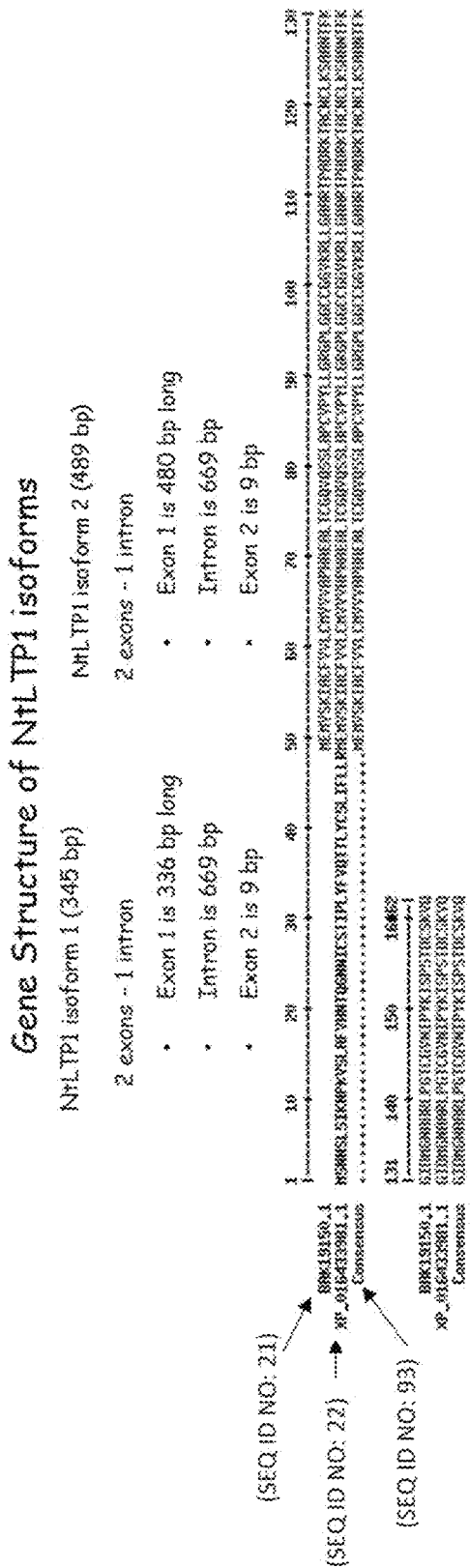
FIG. 8B depicts a sequence alignment and gene structure comparison in tobacco plants of two NtLTP1 isoforms (SEQ ID NOs: 21, 22, and 93, respectively, in order of appearance).
Figure 9:
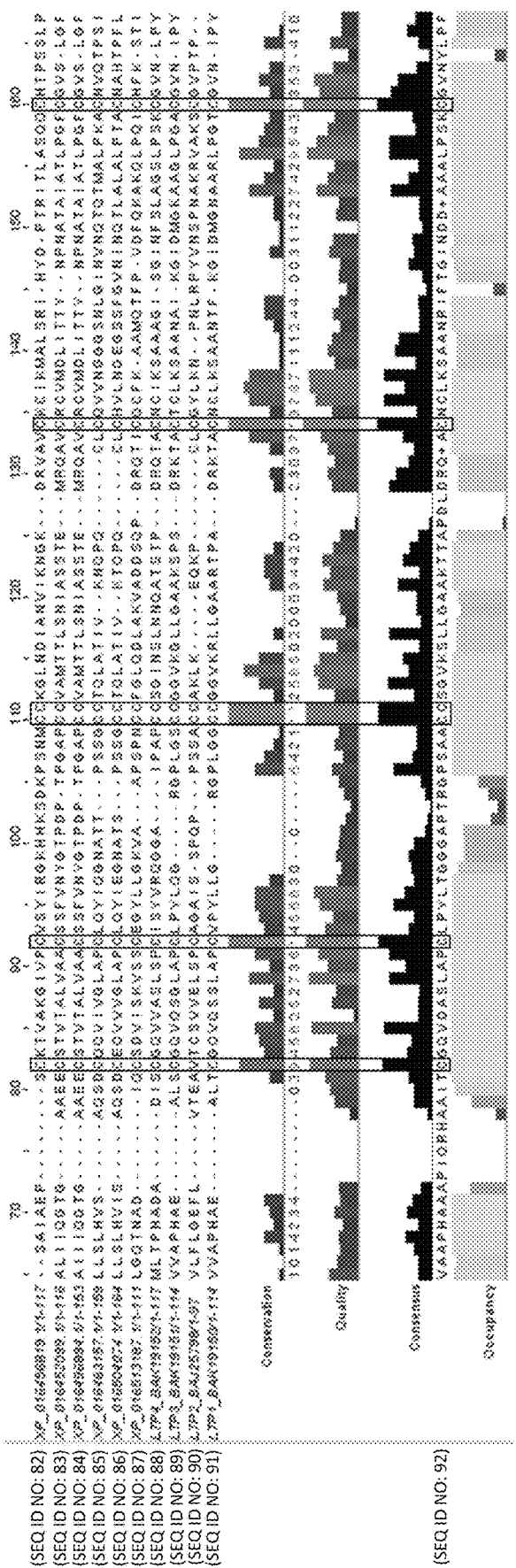
FIG. 9 depicts the conserved motifs of a representative number of NtL TP of the 76 that were identified in the *Nicotiana tabacum* genome following ClustalW multiple sequence alignment algorithm. Six conserved cysteine residues (enclosed in boxes) are notably conserved in >90% of the NtLTPs identified.

Example 1. Identification of Candidate Transcription Factors for Trichome Density Modification Transcription factors involved in regulation of trichome initiation and development were used as query in a search of the National Center for Biotechnology Information (NCBI) database. A similar approach is utilized to identify lipid transfer proteins in tobacco. The resulting sequences were then extracted from a second, internal database. This methodology identified members of the transcription factor families MYB (FIGS. 3A and 3B) and C2H2 (FIG. 4). From these families, three transcription factors candidates are selected for modification of trichome density in plants. This approach also identified 86 members of the lipid transfer protein (LTP) family in tobacco and subsequently led to identification of two variant isoforms of LTP1, isoform two (SEQ ID NO:27) having a 5' extension compared to isoform 1 (SEQ ID NO:26). See FIGS. 8A and 8B. This approach allowed the curation of a list of candidate genes that are trichome-specific and involved in metabolite transport (SEQ ID NOs: 13-27 and 34-36). See Table 1.

Example 2. Construction of Vectors

Figure 2:
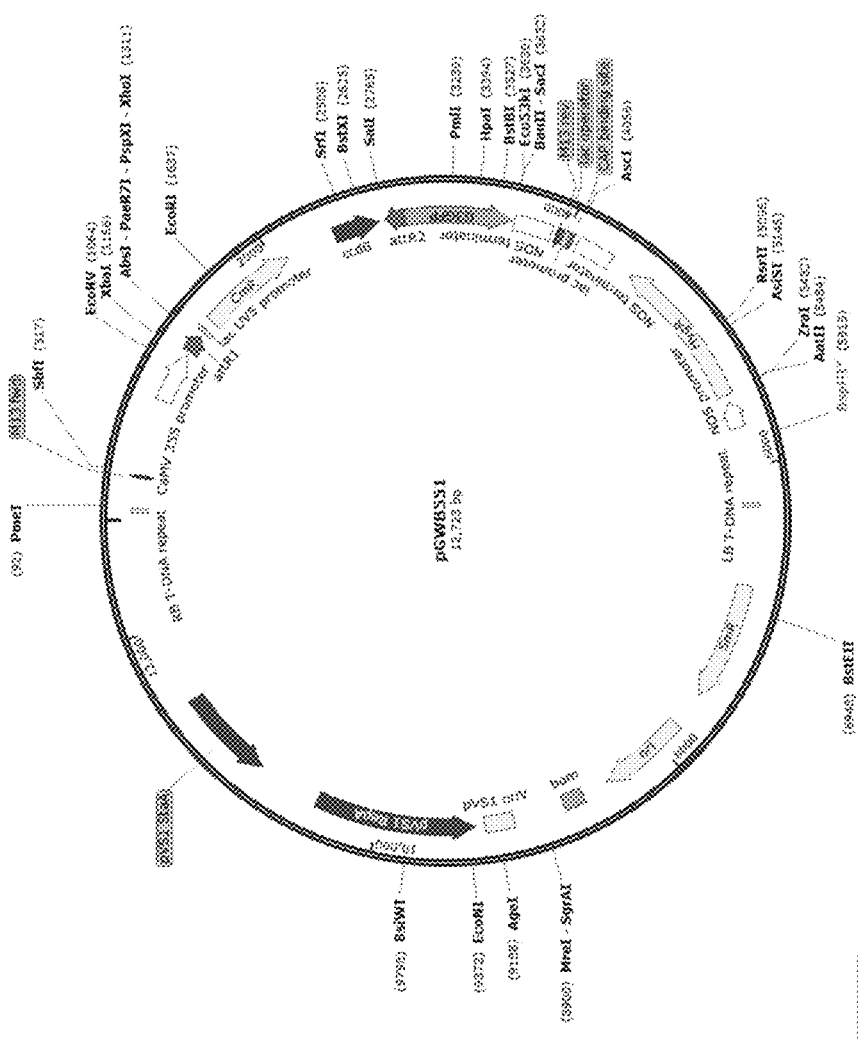
FIG. 2 depicts the expression vector used for tobacco transformation.

The candidate genes identified in Example 1 (e.g., SEQ ID NOs: 13-27 and 34-36) are cloned using the PCR Cloning System with GATEWAY™ Technology (ThermoFisher Scientific, Catalog Number 12535029). The cloned genes are subsequently subcloned into a GATEWAY™ expression vector, where the subcloned gene is fused with GREEN FUORESCENCE PROTEIN (G3GFP) operably linked to a CaMV 35S promoter. See FIG. 2.

Example 3. Transformation and Regeneration of Modified Tobacco Plants

Each of the vector constructs generated in Example 2 is separately transformed into tobacco cells in separate experiments. Briefly, the vectors are introduced into tobacco leaf discs via *Agrobacterium* transformation. See, for example, Mayo et al., Nat. Protoc., 1:1105-1111 (2006); and Horsch et al., Science, 227:1229-1231 (1985).

Transformed tobacco plants (variety 'TN90' and 'Izmir Ego') and *N. benthamiana* are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed, and the *Agrobacterium tumefaciens* cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog (MS) with B5 vitamin liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (1/2 MS medium) and discs are placed upside down in contact with filter paper overlaid on the co-cultivation TOM medium (MS medium with 30 g/L sucrose; 0.1 mg/L 1-napthaleneacetic acid (NAA); and 1 mg/L 6-benzyl aminopurine (BAP)). The Petri plate is sealed with parafilm and incubated in the dark for two days.

After incubation, leaf discs are transferred to regeneration/selection TOM K medium Petri plates (TOM medium plus 200 mg/L cefotaxime and 50 mg/L hygromycin). Calli formed from leaf discs are sub-cultured bi-weekly to fresh TOM-Hyg medium in dim light (between 60 and 80 mE/ms) with photoperiods of 18 hours light, 6 hours dark, at 24° C. until shoots (plantlets) become excisable. Plantlets formed from calli are removed with forceps and subculture into MS rooting medium (MS medium with 3 g/L sucrose, 7 g/L dextrose with 200 mg/L cefotaxime and 50 mg/L hygromycin). Shoots on MS basal medium with 50 mg/L hygromycin are incubated with the same lighting (approximately 60-80 mE/ms) with photoperiods of 18 hours light, 6 hours dark, at 24° C. to induce rooting.

When plantlets comprising both shoots and roots grow large enough (e.g., over half the height of a Magenta™ GA-7 box), they are transferred to Jiffy peat pellets for acclimatization in the growth room. Once established, seedlings are transferred to a greenhouse for further growth, breeding, and analysis.

Example 4. Confirming Expression of Candidate Genes in Modified Tobacco Plants

Figure 11:
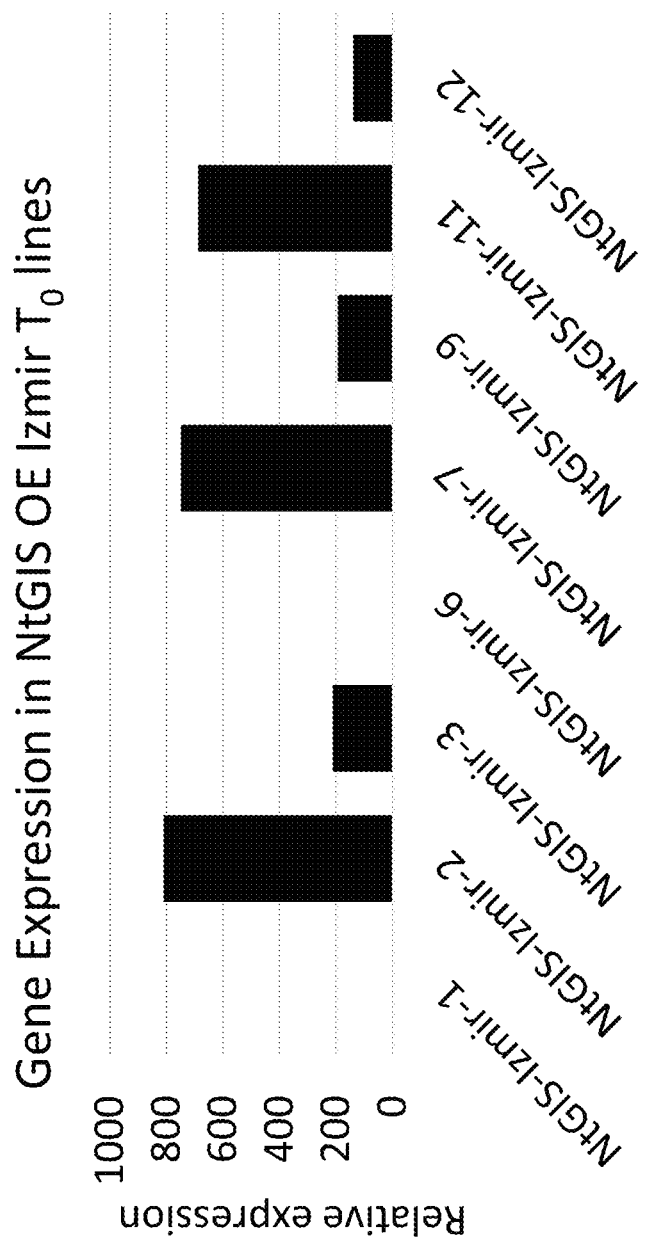
FIG. 11 depicts the relative gene expression of NtGIS (SEQ ID NO: 16) in eight independent Izmir Ego transgenic lines in the To generation. The relative gene expression was quantified following the 2-4ACT method. Expression of NtGIS in a wildtype control Izmir Ego plant is used as a baseline (e.g., wildtype expression is set to 1), and is not shown.
Figure 12:
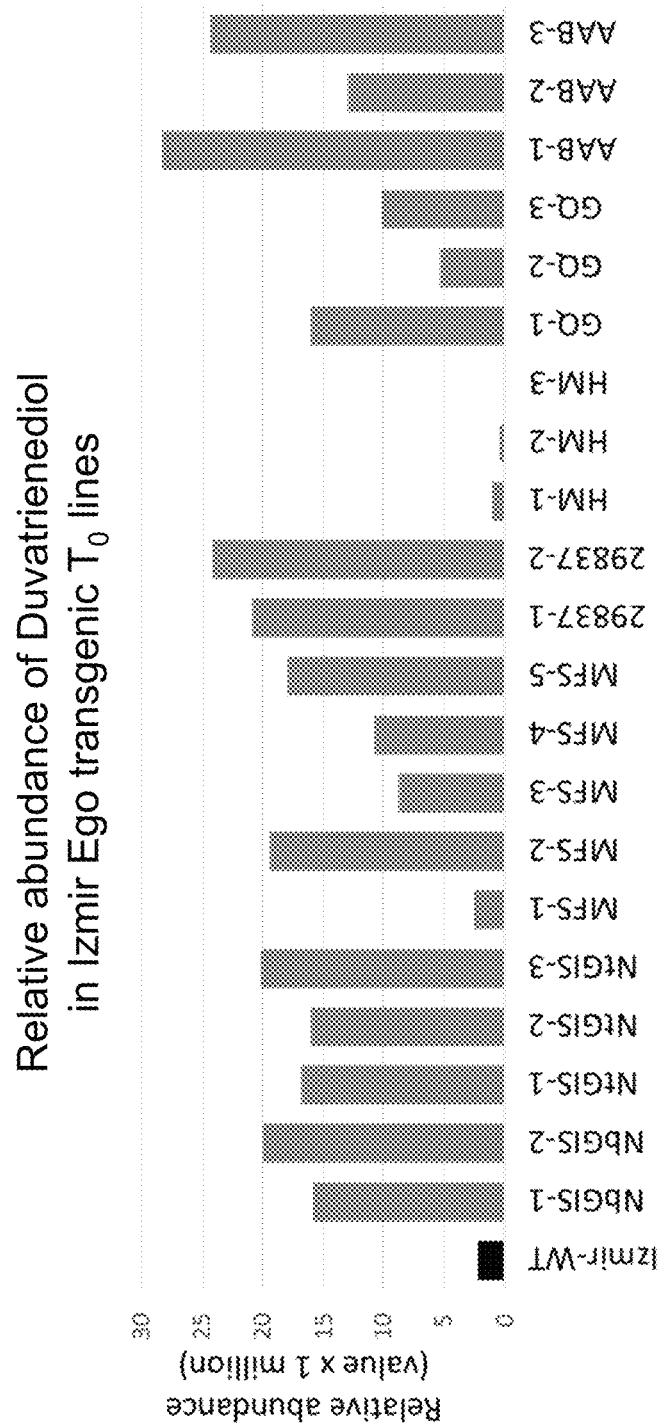
FIG. 12 depicts the relative abundance of duvatrienediol in leaves of To Izmir Ego transgenic lines overexpressing NbGIS (SEQ ID NO: 20), NtGIS (SEQ ID NO: 19), NtMFS (SEQ ID NO: 39), NtNMD (29837; SEQ ID NO: 40), *Nicotiana sylvestris* cembratrienol synthase 2a (HM; SEQ ID NO: 41), geranylgeranyl diphosphate synthase (GQ; SEQ ID NO: 42), and cis-abienol synthase (AAB; SEQ ID NO: 43).
Figure 13:
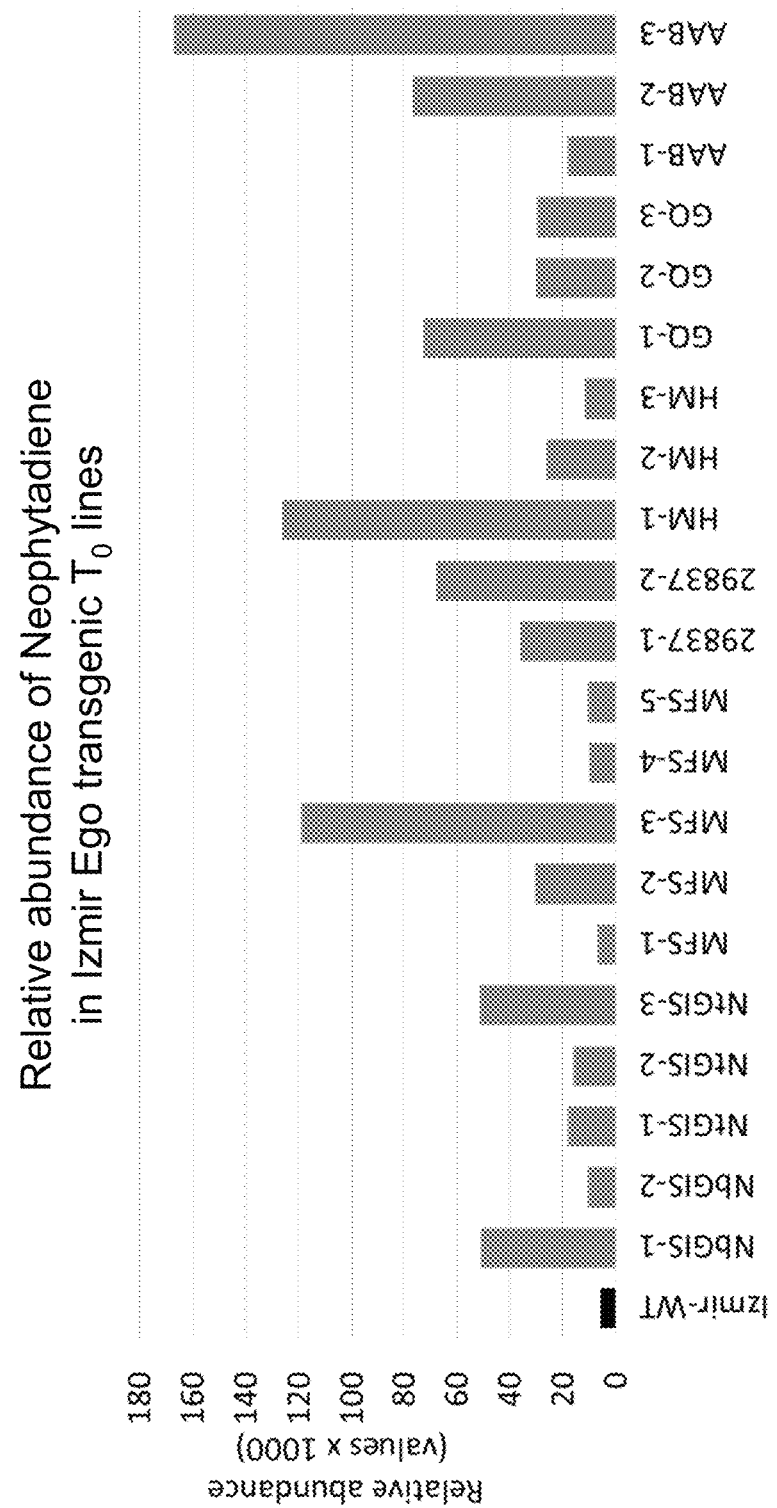
FIG. 13 depicts the relative abundance of neophytadiene in leaves of To Izmir Ego transgenic lines overexpressing NbGIS (SEQ ID NO: 20), NtGIS (SEQ ID NO: 19), NtMFS (SEQ ID NO: 39), NtNMD (29837; SEQ ID NO: 40), *Nicotiana sylvestris* cembratrienol synthase 2a (HM; SEQ ID NO: 41), geranylgeranyl diphosphate synthase (GQ; SEQ ID NO: 42), and cis-abienol synthase (AAB; SEQ ID NO: 43).
Figure 14:
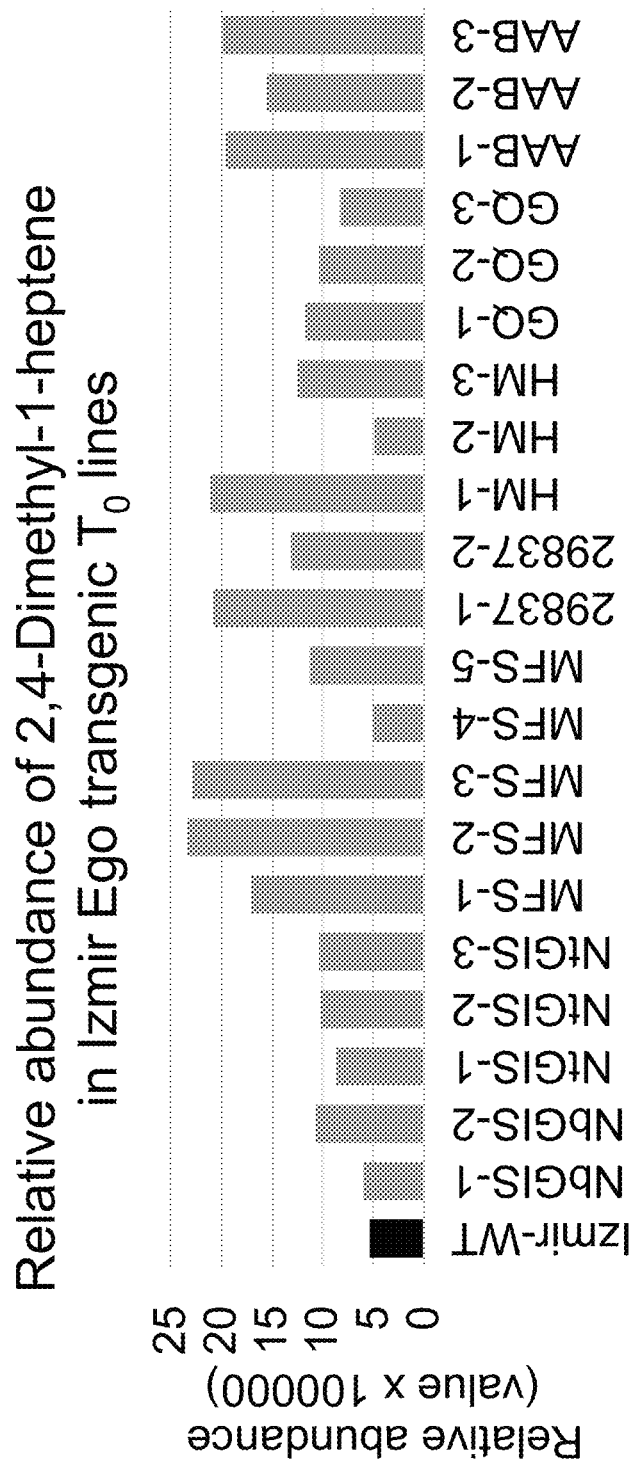
FIG. 14 depicts the relative abundance of 2,4-Dimethyl-1-heptene in leaves of To Izmir Ego transgenic lines overexpressing NbGIS (SEQ ID NO: 20), NtGIS (SEQ ID NO: 19), NtMFS (SEQ ID NO: 39), NtNMD (29837; SEQ ID NO: 40), *Nicotiana sylvestris* cembratrienol synthase 2a (HM; SEQ ID NO: 41), geranylgeranyl diphosphate synthase (GQ; SEQ ID NO: 42), and cis-abienol synthase (AAB; SEQ ID NO: 43).
Figure 15:
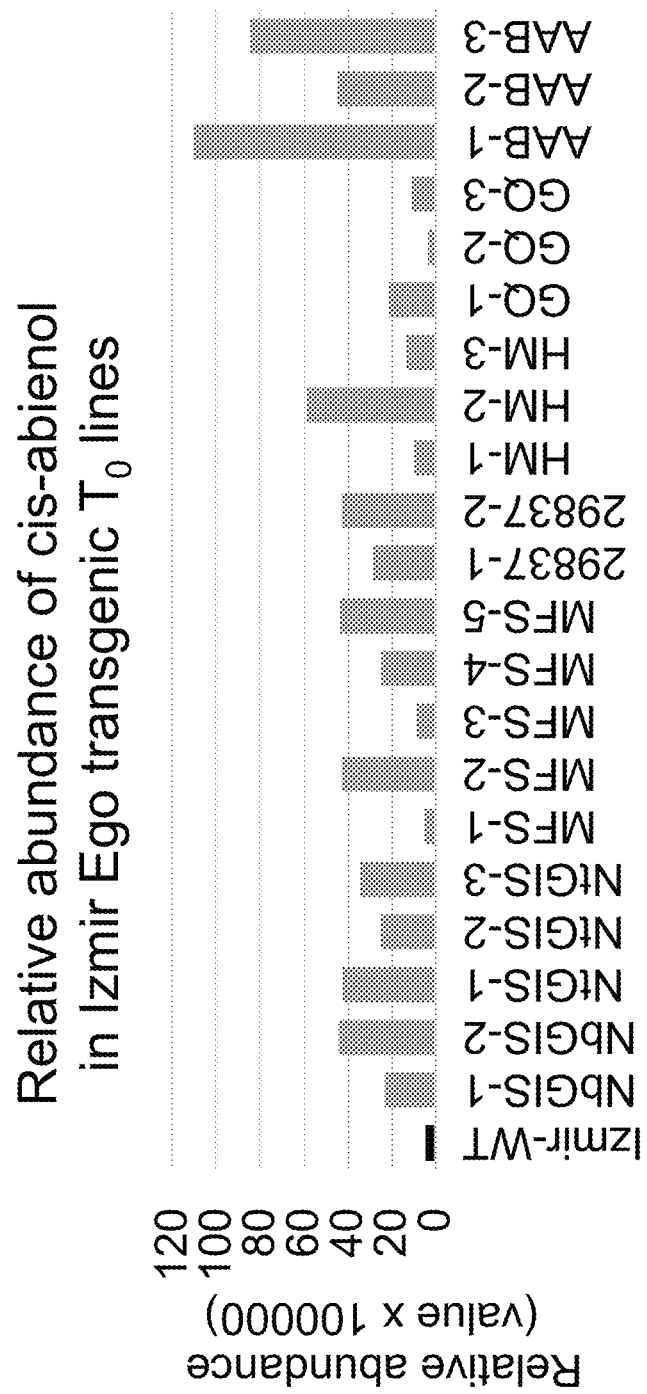
FIG. 15 depicts the relative abundance of cis-abienol in leaves of To Izmir Ego transgenic lines overexpressing NbGIS (SEQ ID NO: 20), NtGIS (SEQ ID NO: 19), NtMFS (SEQ ID NO: 39), NtNMD (29837; SEQ ID NO: 40), *Nicotiana sylvestris* cembratrienol synthase 2a (HM; SEQ ID NO: 41), geranylgeranyl diphosphate synthase (GQ; SEQ ID NO: 42), and cis-abienol synthase (AAB; SEQ ID NO: 43).

During the vegetative stage of growth, RNA is extracted from young leaves of modified tobacco plants produced in Example 3, and from control tobacco plants lacking the recombinant nucleic acid constructs grown under comparable conditions. The extracted RNA is used to generate cDNA. Gene expression of NtMYB and NtGIS is quantified using quantitative real-time PCR (qRT-PCR) in To transgenic plants (see FIGS. 10 and 11). To confirm the constructs are expressing the recombinant nucleic acids, expression of NtMYB and NtGIS in the modified plants is compared to control tobacco plants.

Figure 16:
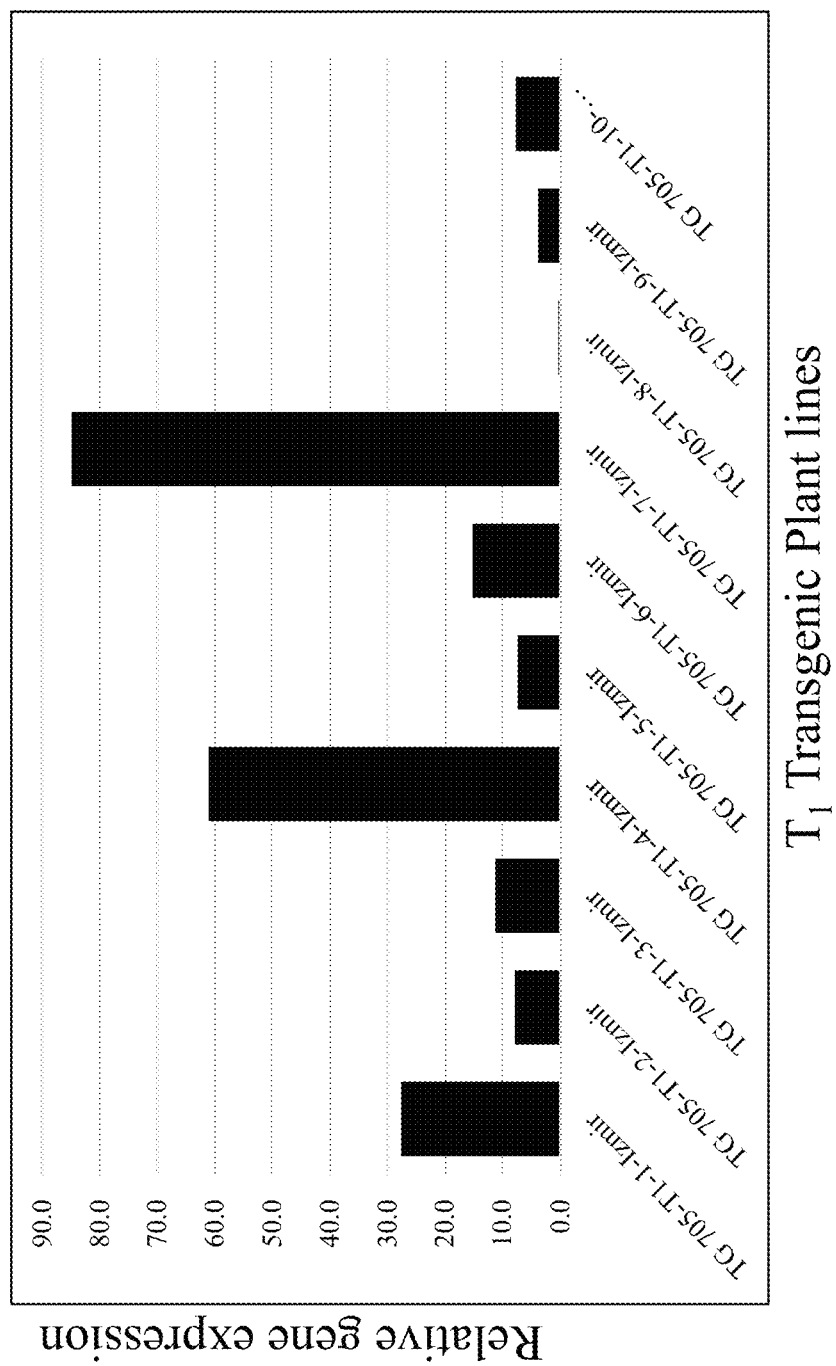
FIG. 16 depicts the relative gene expression levels of NtMYB86 (SEQ ID NO: 13) under control of a CaMV 35S promoter in $T_1$ transgenic tobacco lines in the Izmir Ego variety.
Figure 17:
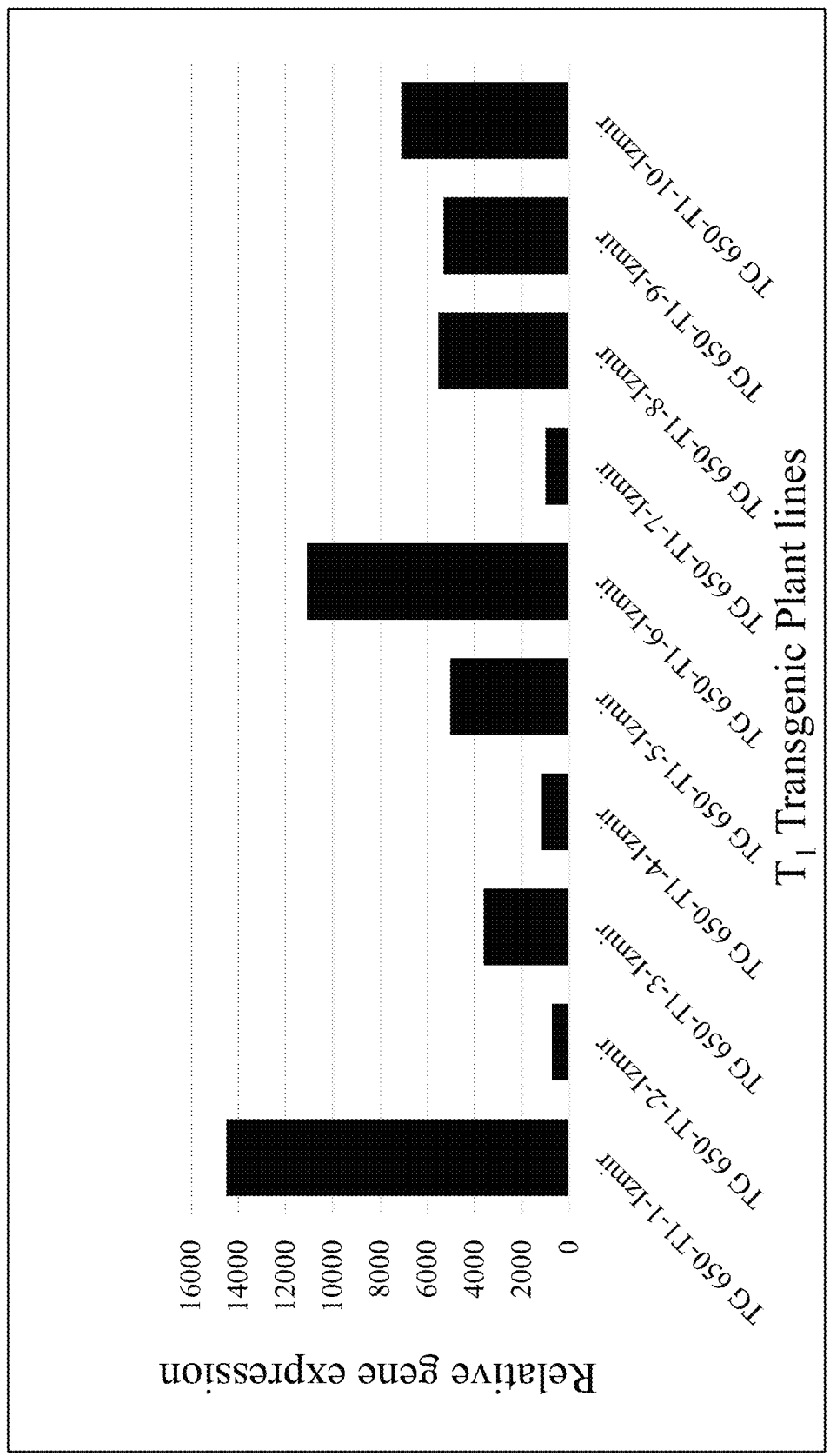
FIG. 17 depicts the relative gene expression levels of NbGIS (SEQ ID NO: 15) under control of a CaMV 35S promoter in $T_1$ transgenic tobacco lines in the Izmir Ego variety.

Gene expression of NtMYB and NbGIS is also quantified in $T_1$ transgenic plants. See FIGS. 16 and 17, respectively.

Figure 5:
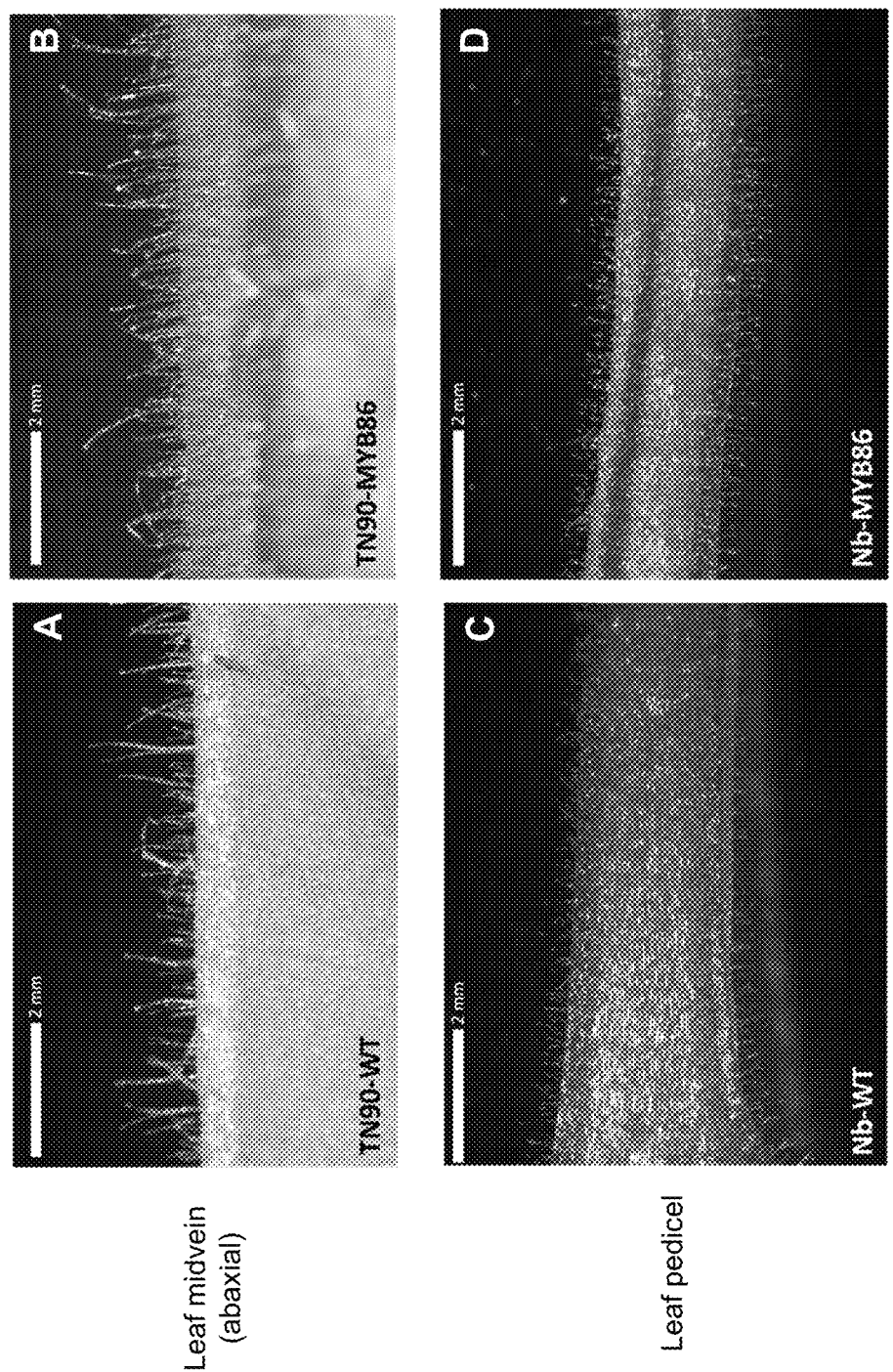
FIG. 5 comprises Panels A, B, C, and D. Panel A depicts glandular trichome density in the abaxial leaf midvein of wild-type (WT) TN90. Panel B depicts glandular trichome density in the abaxial midvein of TN90 overexpressing NtMYB86 (SEQ ID NO: 13) under the control of a CaMV 35S promoter, demonstrating an increase in glandular trichrome density compared to wild-type TN90. An abaxial view of the leaf pedicle of wild-type (WT) *N. benthamiana* is shown in Panel C. Panel D depicts an increase in glandular trichrome density in *N. benthamiana* overexpressing NtMYB86 under the control of a CaMV 35S promoter as compared to wild-type (Panel C). Images are light micrographs shown at 10× magnification.
Figure 6:
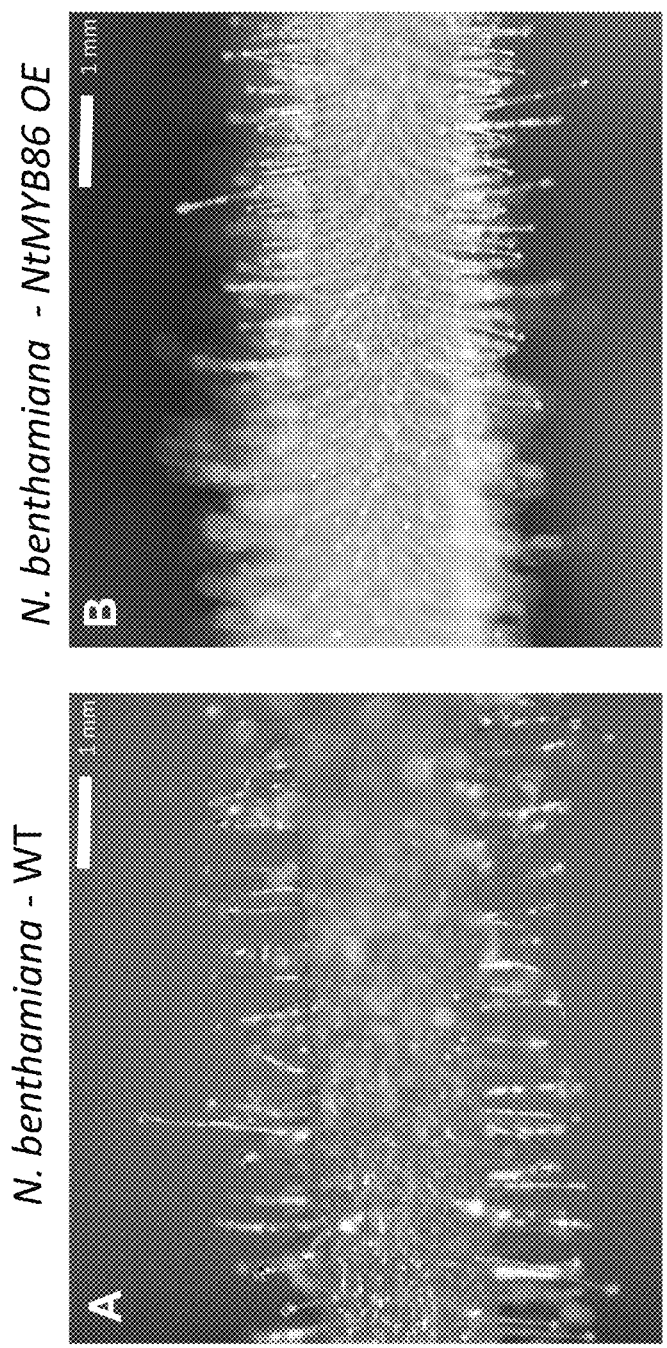
FIG. 6 comprises Panel A and Panel B. Panel A depicts the glandular trichome density in the main vegetative stem of wild-type (WT) *Nicotiana benthamiana*. Panel B depicts the glandular trichome density in the main vegetative stem of *N. benthamiana* overexpressing NtMYB86 (SEQ ID NO: 18). Images are light micrographs shown at 160× magnification.
Figures 7, 7A:
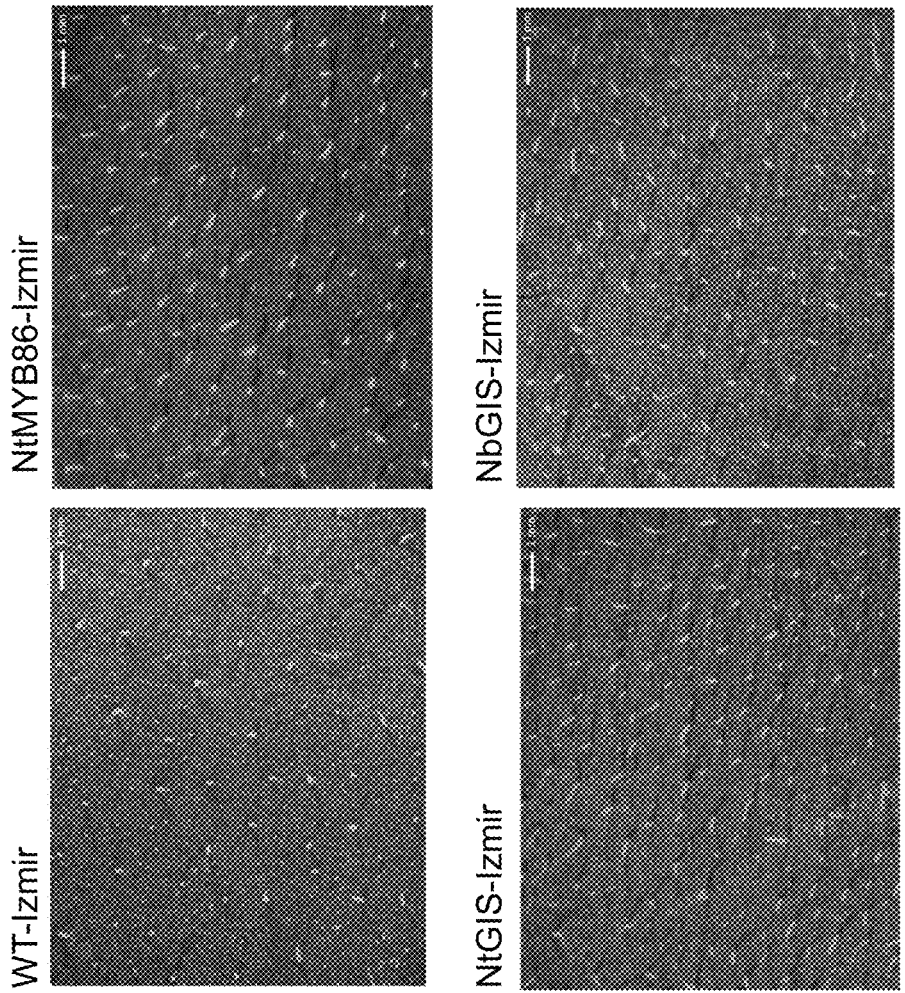
FIG. 7 comprises panels FIG. 7A and FIG. 7B.
FIG. 7A depicts the light micrographs of glandular trichome density of a tobacco leaf overexpressing NtMYB86 (SEQ ID NO: 18) (b), NtGIS (SEQ ID NO: 19) (c), and NbGIS (SEQ ID NO: 20) (c) in Izmir Ego background compared to a wild-type *Nicotiana tabacum* variety Izmir Ego (a). Images are shown at 70× magnification with scale bar representing 1 mm.
Figures 7, 7B:
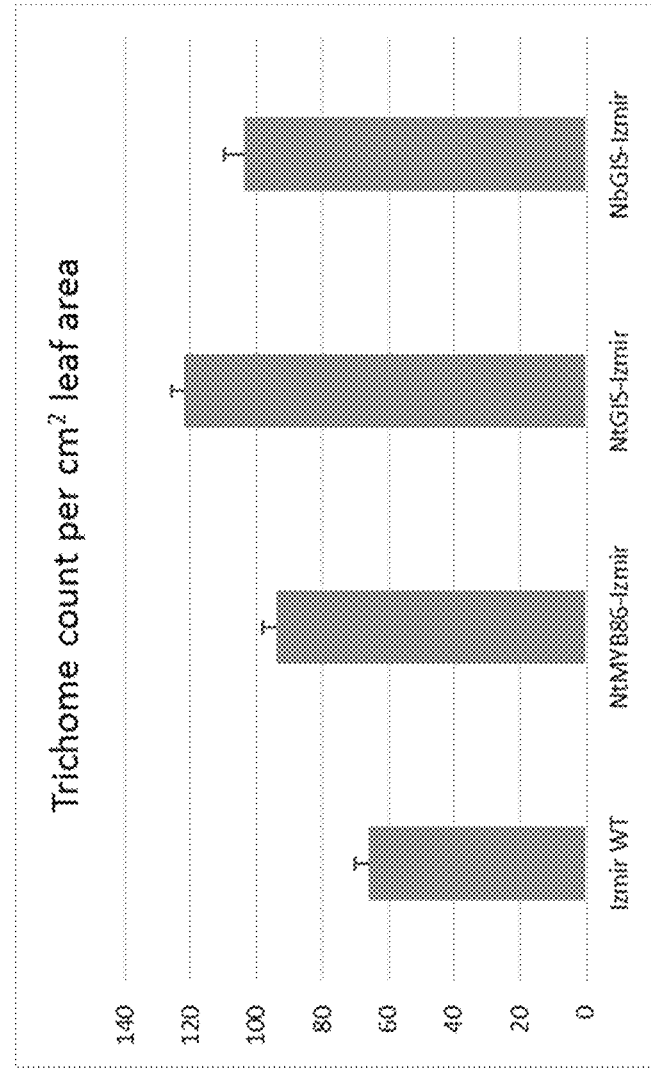
FIG. 7B depicts leaf trichome counts of Izmir Ego WT, Izmir Ego To transgenic lines overexpressing NtMYB86 (SEQ ID NO: 18), NtGIS (SEQ ID NO: 19), and NbGIS (SEQ ID NO: 20).

Example 5. Confirming Modification of Trichome Density in Modified Tobacco Plants During the vegetative stage of growth, samples of transgenic lines of NtMYB86, NtGIS, and NbGIS from various tobacco backgrounds are examined under a stereomicroscope (model/type) to identify changes in trichome density in various plant parts compared with control plants. The results demonstrate that transgenic plants comprising NtMYB86, NtGIS, or NbGIS show an increase in the number of glandular trichomes per unit area (i.e. increased trichrome density) in leaf and stem tissues. (See FIGS. 5-7)

Example 6. Measuring Terpene Levels in Modified Tobacco Plants

During the vegetative stage of growth, young leaves are harvested from the modified tobacco plants from Examples 3, 4, and 5, and from control tobacco plants lacking the recombinant nucleic acid constructs grown under comparable conditions, for use in a qualitative metabolic profile analysis following the protocol outlined by Jiang et al. (Curr Protoc Plant Biol. 2016; 1:345-358). Leaf samples are ground in liquid nitrogen, and then the samples are mixed with 60:40 hexane:ethyl acetate (v/v), supplemented with heptadecanol (an internal standard) and incubated overnight with shaking.

The solvent extracts are concentrated in a refrigerated SpeedVac™ (ThermoFisher Scientific) and placed into a silica column. The column is washed with hexane and allowed to flow through into collection tubes. Samples are aliquoted from the collection tubes and used for gas chromatography-mass spectrometry (GC-MS) analysis of metabolites.

To identify secondary metabolites secreted from leaf trichomes, 1 gram of leaf samples from transgenic lines are cut into small sections and soaked into hexane supplemented with heptadecanol (an internal standard) and incubated overnight with shaking. The extract is filtered and used for analysis of metabolic profile in gas chromatography-mass spectrometry (GC-MS). See FIGS. 12-15.

The invention claimed is:

1. A modified tobacco plant, tobacco seed, or tobacco plant part, comprising a recombinant nucleic acid molecule comprising a nucleic acid sequence encoding an amino acid sequence at least 99% identical to the full length of the amino acid sequence of SEQ ID NO: 18, wherein the nucleic acid sequence is operably linked to a heterologous promoter, and wherein at least one leaf of the modified tobacco plant comprises a greater average trichome density as compared to a leaf of a control tobacco plant grown under comparable conditions.

2. The modified tobacco plant, tobacco seed, or tobacco plant part, of claim 1, wherein the nucleic acid sequence is at least 95% identical to the nucleic acid sequence of SEQ ID NO: 13 or SEQ ID NO: 23.

3. The modified tobacco plant, tobacco seed, or tobacco plant part, of claim 1, wherein the nucleic acid sequence is 100% identical to the nucleic acid sequence SEQ ID NO: 13 or SEQ ID NO: 23.

4. The modified tobacco plant, tobacco seed, or tobacco plant part, of claim 1, wherein the nucleic acid sequence encodes a protein comprising an amino acid sequence 100% identical to the amino acid sequence of SEQ ID NO: 18.

5. The modified tobacco plant, tobacco seed, or tobacco plant part thereof of claim 1, wherein the tobacco plant, tobacco seed, or plant part is of a tobacco variety selected from the group consisting of a flue-cured variety, a bright variety, a Burley variety, a Virginia variety, a Maryland variety, a dark variety, a Galpão variety, an Oriental variety, and a Turkish variety.

6. The modified tobacco plant, tobacco seed, or tobacco plant part thereof of claim 1, wherein the modified tobacco plant is male sterile or cytoplasmically male sterile.

7. The modified tobacco plant, tobacco seed, or tobacco plant part, of claim 1, wherein the heterologous promoter is selected from the group consisting of a constitutive promoter, an inducible promoter, a tissue-preferred promoter, and a tissue-specific promoter.

8. The modified tobacco plant, tobacco seed, or tobacco plant part of claim 1, wherein at least one leaf of the modified tobacco plant comprises a greater average trichome density on the abaxial side of the at least one leaf of the modified tobacco plant as compared to the abaxial side of a leaf of a control tobacco plant grown under comparable conditions.

9. The modified plant, seed, or plant part of claim 1, wherein at least one leaf of the modified tobacco plant comprises a greater average trichome density on the adaxial side of the at least one leaf of the modified tobacco plant as compared to the adaxial side of a leaf of a control tobacco plant grown under comparable conditions.

10. Cured tobacco material from a modified tobacco plant or tobacco plant part comprising a recombinant nucleic acid molecule comprising a nucleic acid sequence encoding an amino acid sequence least 99% identical to the full-length of the amino acid sequence of SEQ ID NO: 18, wherein the nucleic acid sequence is operably linked to a heterologous promoter, and wherein at least one leaf of the modified tobacco plant comprises a greater average trichome density as compared to a leaf of a control tobacco plant grown under comparable conditions.

11. The cured tobacco material of claim 10, wherein the cured tobacco material is selected from the group consisting of flue cured tobacco material, air cured tobacco material, fire cured tobacco material, and sun cured tobacco material.

12. A tobacco product comprising the cured tobacco material of claim 10.

13. The tobacco product of claim 12, wherein the tobacco product is selected from the group consisting of a kretek, a bidi cigarette, a cigarillo, a non-ventilated recess filter cigarette, a vented recess filter cigarette, a cigar, pipe tobacco, cigar tobacco, cigarette tobacco, chewing tobacco, moist snuff, nasal snuff, dry snuff, snus, leaf tobacco, hookah tobacco, shredded tobacco, and cut tobacco.

14. The tobacco product of claim 13, wherein the tobacco product is a smokeless tobacco product.

15. The tobacco product of claim 14, wherein the smokeless tobacco product is selected from the group consisting of loose leaf chewing tobacco, plug chewing tobacco, moist snuff, nasal snuff, dry snuff, and snus.

16. The modified tobacco plant, tobacco seed, or tobacco plant part of claim 1, wherein the greater average trichome density comprises a greater average density of glandular trichomes.

17. The modified tobacco plant, tobacco seed, or tobacco plant part of claim 1, wherein the at least one leaf of the modified tobacco plant comprises at least 80 trichomes per square centimeter.

\* \* \* \* \*

```
SEQUENCE LISTING

<160> NUMBER OF SEQ ID NOS: 93

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggggacaagt ttgtacaaaa aagcaggcta tggggaggca ttcttgttgt ta            52

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggggaccact ttgtacaaga aagctgggta agaaaattgt ccaaatgcat ctgg          54

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggacaagt ttgtacaaaa aagcaggcta tggataggag agatattg                 48

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggggaccact ttgtacaaga aagctgggta caagtgtaga tctaaactc                49

<210> SEQ ID NO 5
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttgcaacaga aagttcattg agt                                            23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcagtttgta tagaaggttg ttgct                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
actccaaaat ttcatattgg tggca                                          25

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggccaaggc acttccattt a                                              21

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggggacaagt ttgtacaaaa aagcaggctt catggaaatg gtaagcaaga               50

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggggaccact ttgtacaaga aagctgggtt ctggaccttg gagcagtcag t             51

<210> SEQ ID NO 11
<211> LENGTH: 49
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggacaagt ttgtacaaaa aagcaggctt catgtccaat aattctctc                  49

<210> SEQ ID NO 12
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggggaccact ttgtacaaga aagctgggtt ctggaccttg gagcagtcag t               51

<210> SEQ ID NO 13
<211> LENGTH: 1275
<212> TYPE: DNA
<213> ORGANISM: Nicotiana tabacum

<400> SEQUENCE: 13
atggggaggc attcttgttg ttacaagcag aagctgagga aaggcctctg gtcccctgag     60
gaagatgaga aacttataaa tcatattagt aaatatggtc atggctgttg gagttcagtc    120
cctaaactag ctgggcttca gaggtgtggc aagagctgca ggctaagatg gattaactac    180
ctgagacctg atttgaaaag aggaacattc tcacaagagg aagagaattt gataattgaa    240
cttcatgcag ttctagggaa caagtggtca caaattgctg ctagattacc tggaagaaca    300
gacaatgaaa tcaagaattt atggaactct tccattaaaa aaaaactaag gcaaaaaggg    360
attgatccaa acactcacaa gcccactttct gaggttgaga atgaagagaa ggtgtcagca    420
atcagtaaaa acaatgagaa agcttctgaa ggctccagtg aactcaattt ctttgaagct    480
catgagaatt ctaactatgg aattgaaaca gagaaaccaa aaccatcttc agcgacgact    540
atggaccgct attccaataa tatgagtgct gctgtagccc caccaacaca tgaattcttc    600
cttaataggt ttgttaacac acatgaaacc tccaccacta gttgcaataa gcctcttgac    660
ttggcaagtt acctctcttt tcagcacttg aattatggct caaacattgg tttgtccatg    720
agtccagaca ccagtaatat tctttttcaac tccataatc ccaagaattc agaaatggtt    780
tctcatcact tcaattccaa catgtcaaca atgataata ttctcacttc catttcaaac    840
tcaattctca catctccaat agcagcagca gtaataatt caataggtc ttttaccagc    900 aatgggagca gtactagtat tgatcaattg caaagaaact gttctttctt tgataacaat    960
gcattctcat ggggagctgc agactgtggg aaatcagaaa aagaagccaa tattcatcca   1020
tcagaaactg atcctgaaga catcaaatgg tctgaatatt tgcatacaca atttttacca   1080
ggcaattcaa tccataatca tcaaataact caagacttgt acagtgaaaa atcaggcaca   1140
caatttgcaa cagaaagttc attgagtagt actacatggc tgcagaacca acagcaacaa   1200
ccttctatac aaactgcaga cttatataat aagcattttc agagaattcc agatgcattt   1260
ggacaatttt cttag                                                    1275

<210> SEQ ID NO 14
<211> LENGTH: 654
<212> TYPE: DNA
```

<213> ORGANISM: Nicotiana tabacum

<400> SEQUENCE: 14

```
atggatagga gagatattga aactcacgat ttcatgaacg tggaatcttt ctcccaactg    60
cccttttatta ggccagcacc aacaaaagaa aaggcagcca ttaagctttt tgggaaagaa   120
ttaggtggtc gtgaggaatc taaatctgtc gattccaatg accatagtga tcaagaatca   180
aaagacagta ctgtcaatgt ctccgacaac cgaaaatttg tatgtaacta ttgttgtagg   240
aatttcccaa cttcacaagc actaggaggc catcaaaatg cacataaaag agaacgtcag   300
aatgccaaaa gagctcaacg tcagccacca aattttcata ttggaaatgt taatggcact   360
tattttcata gttccaggag cagtactact agctttatg gaagtcgtca tgtttataat    420
ggtagccatt attctcaagc tcatactata atggaagtc ccttggcctt ttggagaagc     480
cattcttctc ctcttctaa ttatgctcgt gaccgttcca agatgataga tccattgcca    540
atgtatgtta atggaaattt gaagaccaat agcagctcga tttctttaag ccgatttggg   600
tatgaactga aggaaggagt tcaagatcat gtgagtttag atctacactt gtaa         654
```

<210> SEQ ID NO 15
<211> LENGTH: 648
<212> TYPE: DNA
<213> ORGANISM: Nicotiana sp.

<400> SEQUENCE: 15

```
atggatagga gagatattga aactcacgat ttcatgaacg tggaatcttt ctcccaactg    60
cctttttatta gaccagcacc actaaaagaa aagacagcca ttaggatttt ttgcaaagaa   120
ttaggtggtc gtgacgcatc taaatctgtc gatgccaata atcatagtga tgatcaagaa   180
tcaaaagaca gtactgtcaa tgtctccgac aaccgaaaat tgtatgtaa ttattgttgt     240
aggaatttcc caactccaca agcactagga ggccatcaaa atgcacataa agagaacgt    300
cagaatgcca aaagagctca acgtcagact ccaaaatttc atattggtgg cacttatttta  360
cgtagttcct ggagcagtac tactcgcttt tatggaagtc gtcatgttta taatggtagc   420
cattattctc aagctcatac tataaatgga agtgccttgg cctttttggag aagtcattct  480
tctcctcttt ctaattatgc tcgtgaccct tccaagatga tagatccatt gccagtgtat   540
gttaatggaa atttgaacat caataacagc tcgatttctg taagccgatt tgggtatgaa   600
cagaagcaag aagttcaaga tcatgtgagt ttagatctac acttgtaa               648
```

<210> SEQ ID NO 16
<211> LENGTH: 345
<212> TYPE: DNA
<213> ORGANISM: Nicotiana tabacum

<400> SEQUENCE: 16

```
atggaaatgg taagcaagat tgcatgtttc gtggttttgt gcatggtggt ggttgcaccc    60
catgcagagg cactgacctg cggccaggtt cagtctagcc tggctccttg cgtcccttat   120
ttgctgggcc gcggcccttt gggggttgt tgtggcggcg ttaaacgtct gttgggtgct    180
gctcgcaccc cagcggaccg aaagactgca tgcaattgcc tgaaatcagc cgctaatact   240
tttaagggca ttgatatggg caacgccgct cgtctccctg gtacttgtgg cgttaacatt   300
ccctacaaga tcagtccctc cactgactgc tccaaggtcc agtga                   345
```

<210> SEQ ID NO 17
<211> LENGTH: 489

<212> TYPE: DNA
<213> ORGANISM: Nicotiana tabacum

<400> SEQUENCE: 17

```
atgtccaata attctctctc tataaaaaac cctaaggtct cactagcttt tgtacacaac      60
actcaaggca ataacatttg tagtactatc cccctctact tgtccaaac tactctctat     120
tgttctctaa ttttctttt aagaatggaa atggtaagca agattgcatg tttcgtggtt      180
ttgtgcatgg tggtggttgc accccatgca gaggcactga cctgcggcca ggttcagtct    240
agcctggctc cttgcgtccc ttatttgctg ggccgcggcc ctttggggg ttgttgtggc     300
ggcgttaaac gtctgttggg tgctgctcgc accccagcgg accgaaagac tgcatgcaat    360
tgcctgaaat cagccgctaa tacttttaag ggcattgata tgggcaacgc cgctcgtctc    420
cctggtactt gtggcgttaa cattccctac aagatcagtc cctccactga ctgctccaag    480
gtccagtga                                                            489
```

<210> SEQ ID NO 18
<211> LENGTH: 424
<212> TYPE: PRT
<213> ORGANISM: Nicotiana tabacum

<400> SEQUENCE: 18

```
Met Gly Arg His Ser Cys Cys Tyr Lys Gln Lys Leu Arg Lys Gly Leu
1               5                   10                  15

Trp Ser Pro Glu Glu Asp Glu Lys Leu Ile Asn His Ile Ser Lys Tyr
            20                  25                  30

Gly His Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Thr Phe Ser Gln Glu Glu Asn Leu Ile Ile Glu
65                  70                  75                  80

Leu His Ala Val Leu Gly Asn Lys Trp Ser Gln Ile Ala Ala Arg Leu
                85                  90                  95

Pro Gly Arg Thr Asp Asn Glu Ile Lys Asn Leu Trp Asn Ser Ser Ile
            100                 105                 110

Lys Lys Lys Leu Arg Gln Lys Gly Ile Asp Pro Asn Thr His Lys Pro
        115                 120                 125

Leu Ser Glu Val Glu Asn Glu Glu Lys Val Ser Ala Ile Ser Lys Asn
    130                 135                 140

Asn Glu Lys Ala Ser Glu Gly Ser Ser Glu Leu Asn Phe Phe Glu Ala
145                 150                 155                 160

His Glu Asn Ser Asn Tyr Gly Ile Glu Thr Glu Lys Pro Lys Pro Ser
                165                 170                 175

Ser Ala Thr Thr Met Asp Arg Tyr Ser Asn Asn Met Ser Ala Ala Val
            180                 185                 190

Ala Pro Pro Thr His Glu Phe Phe Leu Asn Arg Phe Val Asn Thr His
        195                 200                 205

Glu Thr Ser Thr Thr Ser Cys Asn Lys Pro Leu Asp Leu Ala Ser Tyr
    210                 215                 220

Leu Ser Phe Gln His Leu Asn Tyr Gly Ser Asn Ile Gly Leu Ser Met
225                 230                 235                 240

Ser Pro Asp Thr Ser Asn Ile Leu Phe Asn Ser Asn Pro Lys Asn
                245                 250                 255
```

-continued

```
Ser Glu Met Val Ser His His Phe Asn Ser Asn Met Ser Thr Asn Asp
            260                 265                 270

Asn Ile Leu Thr Ser Ile Ser Asn Ser Ile Leu Thr Ser Pro Ile Ala
        275                 280                 285

Ala Ala Ser Asn Asn Ser Ile Gly Ser Phe Thr Ser Asn Gly Ser Ser
    290                 295                 300

Thr Ser Ile Asp Gln Leu Gln Arg Asn Cys Ser Phe Phe Asp Asn Asn
305                 310                 315                 320

Ala Phe Ser Trp Gly Ala Ala Asp Cys Gly Lys Ser Glu Lys Glu Ala
                325                 330                 335

Asn Ile His Pro Ser Glu Thr Asp Pro Glu Asp Ile Lys Trp Ser Glu
            340                 345                 350

Tyr Leu His Thr Gln Phe Leu Pro Gly Asn Ser Ile His Asn His Gln
        355                 360                 365

Ile Thr Gln Asp Leu Tyr Ser Glu Lys Ser Gly Thr Gln Phe Ala Thr
370                 375                 380

Glu Ser Ser Leu Ser Ser Thr Thr Trp Leu Gln Asn Gln Gln Gln Gln
385                 390                 395                 400

Pro Ser Ile Gln Thr Ala Asp Leu Tyr Asn Lys His Phe Gln Arg Ile
                405                 410                 415

Pro Asp Ala Phe Gly Gln Phe Ser
            420

<210> SEQ ID NO 19
<211> LENGTH: 217
<212> TYPE: PRT
<213> ORGANISM: Nicotiana tabacum

<400> SEQUENCE: 19

Met Asp Arg Arg Asp Ile Glu Thr His Asp Phe Met Asn Val Glu Ser
1               5                   10                  15

Phe Ser Gln Leu Pro Phe Ile Arg Pro Ala Pro Thr Lys Glu Lys Ala
            20                  25                  30

Ala Ile Lys Leu Phe Gly Lys Glu Leu Gly Gly Arg Glu Glu Ser Lys
        35                  40                  45

Ser Val Asp Ser Asn Asp His Ser Asp Gln Glu Ser Lys Asp Ser Thr
    50                  55                  60

Val Asn Val Ser Asp Asn Arg Lys Phe Val Cys Asn Tyr Cys Cys Arg
65                  70                  75                  80

Asn Phe Pro Thr Ser Gln Ala Leu Gly Gly His Gln Asn Ala His Lys
                85                  90                  95

Arg Glu Arg Gln Asn Ala Lys Arg Ala Gln Arg Gln Pro Pro Asn Phe
            100                 105                 110

His Ile Gly Asn Val Asn Gly Thr Tyr Phe His Ser Ser Arg Ser Ser
        115                 120                 125

Thr Thr Ser Phe Tyr Gly Ser Arg His Val Tyr Asn Gly Ser His Tyr
    130                 135                 140

Ser Gln Ala His Thr Ile Asn Gly Ser Pro Leu Ala Phe Trp Arg Ser
145                 150                 155                 160

His Ser Ser Pro Leu Ser Asn Tyr Ala Arg Asp Arg Ser Lys Met Ile
                165                 170                 175

Asp Pro Leu Pro Met Tyr Val Asn Gly Asn Leu Lys Thr Asn Ser Ser
            180                 185                 190

Ser Ile Ser Leu Ser Arg Phe Gly Tyr Glu Leu Lys Glu Gly Val Gln
        195                 200                 205
```

```
Asp His Val Ser Leu Asp Leu His Leu
    210                 215
```

<210> SEQ ID NO 20
<211> LENGTH: 215
<212> TYPE: PRT
<213> ORGANISM: Nicotiana sp.

<400> SEQUENCE: 20

```
Met Asp Arg Arg Asp Ile Glu Thr His Asp Phe Met Asn Val Glu Ser
1               5                   10                  15

Phe Ser Gln Leu Pro Phe Ile Arg Pro Ala Pro Leu Lys Glu Lys Thr
            20                  25                  30

Ala Ile Arg Ile Phe Cys Lys Glu Leu Gly Gly Arg Asp Ala Ser Lys
        35                  40                  45

Ser Val Asp Ala Asn Asn His Ser Asp Asp Gln Glu Ser Lys Asp Ser
    50                  55                  60

Thr Val Asn Val Ser Asp Asn Arg Lys Phe Val Cys Asn Tyr Cys Cys
65                  70                  75                  80

Arg Asn Phe Pro Thr Pro Gln Ala Leu Gly Gly His Gln Asn Ala His
                85                  90                  95

Lys Arg Glu Arg Gln Asn Ala Lys Arg Ala Gln Arg Gln Thr Pro Lys
            100                 105                 110

Phe His Ile Gly Gly Thr Tyr Leu Arg Ser Ser Trp Ser Ser Thr Thr
        115                 120                 125

Arg Phe Tyr Gly Ser Arg His Val Tyr Asn Gly Ser His Tyr Ser Gln
    130                 135                 140

Ala His Thr Ile Asn Gly Ser Ala Leu Ala Phe Trp Arg Ser His Ser
145                 150                 155                 160

Ser Pro Leu Ser Asn Tyr Ala Arg Asp Pro Ser Lys Met Ile Asp Pro
                165                 170                 175

Leu Pro Val Tyr Val Asn Gly Asn Leu Asn Ile Asn Asn Ser Ser Ile
            180                 185                 190

Ser Val Ser Arg Phe Gly Tyr Glu Gln Lys Gln Glu Val Gln Asp His
        195                 200                 205

Val Ser Leu Asp Leu His Leu
    210                 215
```

<210> SEQ ID NO 21
<211> LENGTH: 114
<212> TYPE: PRT
<213> ORGANISM: Nicotiana tabacum

<400> SEQUENCE: 21

```
Met Glu Met Val Ser Lys Ile Ala Cys Phe Val Leu Cys Met Val
1               5                   10                  15

Val Val Ala Pro His Ala Glu Ala Leu Thr Cys Gly Gln Val Gln Ser
            20                  25                  30

Ser Leu Ala Pro Cys Val Pro Tyr Leu Leu Gly Arg Gly Pro Leu Gly
        35                  40                  45

Gly Cys Cys Gly Gly Val Lys Arg Leu Leu Gly Ala Ala Arg Thr Pro
    50                  55                  60

Ala Asp Arg Lys Thr Ala Cys Asn Cys Leu Lys Ser Ala Ala Asn Thr
65                  70                  75                  80

Phe Lys Gly Ile Asp Met Gly Asn Ala Ala Arg Leu Pro Gly Thr Cys
                85                  90                  95
```

Gly Val Asn Ile Pro Tyr Lys Ile Ser Pro Ser Thr Asp Cys Ser Lys
            100                 105                 110

Val Gln

<210> SEQ ID NO 22
<211> LENGTH: 162
<212> TYPE: PRT
<213> ORGANISM: Nicotiana tabacum

<400> SEQUENCE: 22

Met Ser Asn Asn Ser Leu Ser Ile Lys Asn Pro Lys Val Ser Leu Ala
1               5                   10                  15

Phe Val His Asn Thr Gln Gly Asn Asn Ile Cys Ser Thr Ile Pro Leu
            20                  25                  30

Tyr Phe Val Gln Thr Thr Leu Tyr Cys Ser Leu Ile Phe Leu Leu Arg
        35                  40                  45

Met Glu Met Val Ser Lys Ile Ala Cys Phe Val Leu Cys Met Val
    50                  55                  60

Val Val Ala Pro His Ala Glu Ala Leu Thr Cys Gly Gln Val Gln Ser
65                  70                  75                  80

Ser Leu Ala Pro Cys Val Pro Tyr Leu Leu Gly Arg Gly Pro Leu Gly
                85                  90                  95

Gly Cys Cys Gly Gly Val Lys Arg Leu Leu Gly Ala Ala Arg Thr Pro
            100                 105                 110

Ala Asp Arg Lys Thr Ala Cys Asn Cys Leu Lys Ser Ala Ala Asn Thr
            115                 120                 125

Phe Lys Gly Ile Asp Met Gly Asn Ala Ala Arg Leu Pro Gly Thr Cys
        130                 135                 140

Gly Val Asn Ile Pro Tyr Lys Ile Ser Pro Ser Thr Asp Cys Ser Lys
145                 150                 155                 160

Val Gln

<210> SEQ ID NO 23
<211> LENGTH: 1448
<212> TYPE: DNA
<213> ORGANISM: Nicotiana tabacum

<400> SEQUENCE: 23
atggggaggc attcttgttg ttacaagcag aagctgagga aaggcctctg gtcccctgag       60
gaagatgaga aacttataaa tcatattagt aaatatggtc atggctgttg gagttcagtc      120
cctaaactag ctggtacaat acacactata ttacctcaat tactttttact gagtttaatt     180 tcttgaaaat gcatgaggaa aaataacact agtttgtttt tgatgcaggg cttcagaggt     240
gtggcaagag ctgcaggcta agatggatta actacctgag acctgatttg aaaagaggaa     300
cattctcaca agaggaagag aatttgataa ttgaacttca tgcagttcta gggaacaagt     360
aaatacatat tttcttgatt cttatagtac ttttcatgat gtaacaaaac tgacaccttg     420
acttcttttt ccataggtgg tcacaaattg ctgctagatt acctggaaga acagacaatg     480
aaatcaagaa tttatggaac tcttccatta aaaaaaaact aaggcaaaaa gggattgatc     540
caaacactca caagccactt tctgaggttg agaatgaaga aaggtgtca gcaatcagta      600 aaaacaatga aaagcttct gaaggctcca gtgaactcaa tttctttgaa gctcatgaga     660
attctaacta tggaattgaa acagagaaac caaaaccatc ttcagcgacg actatggacc     720
gctattccaa taatatgagt gctgctgtag ccccaccaac acatgaattc ttccttaata     780

```
ggtttgttaa cacacatgaa acctccacca ctagttgcaa taagcctctt gacttggcaa        840
gttacctctc ttttcagcac ttgaattatg gctcaaacat tggtttgtcc atgagtccag        900
acaccagtaa tattcttttc aactccaata atcccaagaa ttcagaaatg gtttctcatc        960
acttcaattc caacatgtca acaaatgata atattctcac ttccatttca aactcaattc       1020
tcacatctcc aatagcagca gcaagtaata attcaatagg gtcttttacc agcaatggga       1080
gcagtactag tattgatcaa ttgcaaagaa actgttcttt ctttgataac aatgcattct       1140
catggggagc tgcagactgt gggaaatcag aaaagaagc caatattcat ccatcagaaa        1200
ctgatcctga agacatcaaa tggtctgaat atttgcatac acaatttta ccaggcaatt        1260 caatccataa tcatcaaata actcaagact tgtacagtga aaaatcaggc acacaatttg       1320
caacagaaag ttcattgagt agtactacat ggctgcagaa ccaacagcaa caaccttcta       1380
tacaaactgc agacttatat aataagcatt ttcagagaat tccagatgca tttggacaat       1440
tttcttag                                                                1448

<210> SEQ ID NO 24
<211> LENGTH: 654
<212> TYPE: DNA
<213> ORGANISM: Nicotiana tabacum

<400> SEQUENCE: 24
atggatagga gagatattga aactcacgat ttcatgaacg tggaatcttt ctcccaactg         60 cccttttatta ggccagcacc aacaaaagaa aaggcagcca ttaagctttt tgggaaagaa       120
ttaggtggtc gtgaggaatc taaatctgtc gattccaatg accatagtga tcaagaatca       180
aaagacagta ctgtcaatgt ctccgacaac cgaaaatttg tatgtaacta ttgttgtagg       240
aatttcccaa cttcacaagc actaggaggc catcaaaatg cacataaaag agaacgtcag       300
aatgccaaaa gagctcaacg tcagccacca aattttcata ttggaaatgt taatggcact       360
tattttcata gttccaggag cagtactact agcttttatg gaagtcgtca tgtttataat       420
ggtagccatt attctcaagc tcatactata atggaagtc ccttggcctt ttggagaagc        480
cattcttctc ctctttctaa ttatgctcgt gaccgttcca agatgataga tccattgcca       540
atgtatgtta atggaaattt gaagaccaat agcagctcga tttctttaag ccgatttggg       600
tatgaactga aggaaggagt tcaagatcat gtgagtttag atctacactt gtaa            654

<210> SEQ ID NO 25
<211> LENGTH: 648
<212> TYPE: DNA
<213> ORGANISM: Nicotiana sp.

<400> SEQUENCE: 25
atggatagga gagatattga aactcacgat ttcatgaacg tggaatcttt ctcccaactg         60
ccttttatta gaccagcacc actaaaagaa aagacagcca ttaggatttt ttgcaaagaa       120
ttaggtggtc gtgacgcatc taaatctgtc gatgccaata atcatagtga tgatcaagaa       180
tcaaaagaca gtactgtcaa tgtctccgac aaccgaaaat tgtatgtaa ttattgttgt        240 aggaatttcc caactccaca agcactagga ggccatcaaa atgcacataa agagaacgt        300 cagaatgcca aaagagctca acgtcagact ccaaaatttc atattggtgg cacttattta       360
cgtagttcct ggagcagtac tactcgcttt tatggaagtc gtcatgttta atggtagc         420 cattattctc aagctcatac tataaatgga agtgccttgg ccttttggag aagtcattct       480
```

| | |
|---|---|
| tctcctctttt ctaattatgc tcgtgaccct tccaagatga tagatccatt gccagtgtat | 540 |
| gttaatggaa atttgaacat caataacagc tcgatttctg taagccgatt tgggtatgaa | 600 |
| cagaagcaag aagttcaaga tcatgtgagt ttagatctac acttgtaa | 648 |

<210> SEQ ID NO 26
<211> LENGTH: 1014
<212> TYPE: DNA
<213> ORGANISM: Nicotiana tabacum

<400> SEQUENCE: 26

| | |
|---|---|
| atggaaatgg taagcaagat tgcatgtttc gtggttttgt gcatggtggt ggttgcaccc | 60 |
| catgcagagg cactgacctg cggccaggtt cagtctagcc tggctccttg cgtcccttat | 120 |
| ttgctgggcc gcggcccttt gggggttgt tgtggcggcg ttaaacgtct gttgggtgct | 180 |
| gctcgcaccc cagcggaccg aaagactgca tgcaattgcc tgaaatcagc cgctaatact | 240 |
| tttaagggca ttgatatggg caacgccgct cgtctccctg gtacttgtgg cgttaacatt | 300 |
| ccctacaaga tcagtccctc cactgactgc tccaagtatg tttttcactt tcttttcttt | 360 |
| ttattatgag tttacgatct cttcatttac attgtaaaga attttgtaa gatcaggtta | 420 |
| aatttgaact acaacaagaa gtaacttttt atggtaacat aaaaaaataa agtaatgcta | 480 |
| tcaaattata actgatatga taatgtaaaa aaacttaatc tccttttgct atccttacac | 540 |
| tacccatatt ttcattctta cttcaatttt acttttccgg ctccacttta attgattttt | 600 |
| ttgcccctttt ttatagtata gtacattatt tgattataac tgatatgatt ttttttgatat | 660 |
| caagaaagaa ctaaaaaaat tttccaaagt tgtccctgga gtaaagagtt ggactatctg | 720 |
| ttatttttaa tgaacaaatt aaagagataa taaaagttaa tatgattaat tttattatta | 780 |
| attaatatta aaaagcgaac cccttaatat gagtgaaaac aaccaaataa tcaattaaag | 840 |
| tggatcggaa gaagcaatca cttgaaagtg gtgtaacatg atacataatc acatatttat | 900 |
| acgacactga attggctggt aagtgagaag attattattc ataaccagtg cgttttttt | 960 |
| ggtgtgcgta tggggttaat gttggttttc atgtgacaat gcagggtcca gtga | 1014 |

<210> SEQ ID NO 27
<211> LENGTH: 1158
<212> TYPE: DNA
<213> ORGANISM: Nicotiana tabacum

<400> SEQUENCE: 27

| | |
|---|---|
| atgtccaata attctctctc tataaaaaac cctaaggtct cactagcttt tgtacacaac | 60 |
| actcaaggca ataacatttg tagtactatc cccctctact ttgtccaaac tactctctat | 120 |
| tgttctctaa ttttcttttt aagaatggaa atggtaagca agattgcatg tttcgtggtt | 180 |
| ttgtgcatgg tggtggttgc accccatgca gaggcactga cctgcggcca ggttcagtct | 240 |
| agcctggctc cttgcgtccc ttatttgctg ggccgcggcc ctttgggggg ttgttgtggc | 300 |
| ggcgttaaac gtctgttggg tgctgctcgc accccagcgg accgaaagac tgcatgcaat | 360 |
| tgcctgaaat cagccgctaa tacttttaag gcattgata tgggcaacgc cgctcgtctc | 420 |
| cctggtactt gtggcgttaa cattccctac aagatcagtc cctccactga ctgctccaag | 480 |
| tatgttttc actttctttt cttttattta tgagtttacg atctcttcat ttacattgta | 540 |
| aagaattttt gtaagatcag gttaaatttg aactacaaca agaagtaact ttttatggta | 600 |
| acataaaaaa ataagtaat gctatcaaat tataactgat atgataatgt aaaaaaactt | 660 |
| aatctccttt tgctatcctt acactaccca tattttcatt cttacttcaa ttttactttt | 720 |

```
ccggctccac tttaattgat ttttttgccc tttttatag tatagtacat tatttgatta      780
taactgatat gattttttg atatcaagaa agaactaaaa aaattttcca aagttgtccc      840
tggagtaaag agttggacta tctgttattt ttaatgaaca aattaaagag ataataaaag    900
ttaatatgat taattttatt attaattaat attaaaaagc gaacccctta atatgagtga    960
aaacaaccaa ataatcaatt aaagtggatc ggaagaagca atcacttgaa agtggtgtaa   1020
catgatacat aatcacatat ttatacgaca ctgaattggc tggtaagtga gaagattatt   1080
attcataacc agtgcgtttt ttttggtgtg cgtatggggt taatgttggt tttcatgtga   1140
caatgcaggg tccagtga                                                 1158
```

<210> SEQ ID NO 28
<211> LENGTH: 1566
<212> TYPE: DNA
<213> ORGANISM: Cannabis sativa

<400> SEQUENCE: 28

```
atggggaggc actcttgttg ttacaagcag aaactgagaa aagggttgtg gtcaccagaa     60
gaagatgaga aacttcttaa ttatataacc aagcatggac atggctgctg gagctctgtc   120
cctaagctag ctggtcttca gagatgtgga aaaagttgca ggctaaggtg gataaattat    180
ttgaggcctg atttgaaaag aggcccattt tcacaacaag aggagaattt gataattgaa    240
cttcatgcag ttcttggcaa cagatggtca cagattgcag ctcagttacc aggaagaaca    300
gataatgaga ttaaaaactt atggaattct tgcattaaga agaaactgag gcaaaagggg    360
attgacccaa atactcataa gccattatct gaggtagaaa atgacattgg taataaattg    420
gagaacaagg gtaacaaagc tgcaaccaat aacaacaaca atgagaatat taataattct    480
actgttagag cttcttcatt aggaaactta tccaatgatc atcatcatca tcatcatcat    540
catctgaatc tagctgacca gtcacaacca tcaatggcgg ccatcaatcg ttacccacta    600
ttggaagtct catcctcaac tccgccgaca caagaattct tcatagaaaa atcaacagat    660
accagatcat caccatcaat atcatcatca tcaccttgtg attttctac ctacttctct     720 ttccactcaa acaattacaa tacgacgtcg tccgctgctg cagctgctgc tgtttctcat    780
catcaagatc aaaacaacaa caacaacatg ccagtttct gcttcaacat taatcaaaat     840
tcaactagac ctccacaaca ccatcatcat aatcagatga ttagtaatct catccagcca    900
ctacaacaac aagtatcacc ttcatcaaca acaacagcat catcatcatc accaccctcc    960
aatattccac gtgtaaagcc ctccataagt ctcccccttat tatctgatca ccaaaacaac   1020
agtaatagca ctactactac tactacaaca actactggag ccgtacaaaa ttgggaaact   1080
agtactttca gcaacaacgg aagtagtagt agtagctgca atatcgaatt acaaggtaat   1140
aataataaca acaacaacaa cttctttgat cacaacacta attccaccgc cgcggccgcc    1200
gccgccgccg ctcctaataa cttctcgtgg ggattagtca atgaaagtac tgttggtagc    1260
ataaaatctg atgacccaga agacataaaa tggtctgaat atctccatag ccccttttctt   1320 cttggtggag gaattagtaa tactaataat caaaattctt cttcttcttc acatcttcaa    1380 cccatttgt acagtaacat tgtgaaacca gaatcacact ttagtaatac tactactgct   1440
acaggatcaa accccacgtg gcatcatcag aacgatcatc atcagctaca agcggcttca    1500
tcagaaataa tgtacactaa taagatctca cagagacttg ctgtagcttt tggacagacc    1560
cttag                                                              1566
```

<210> SEQ ID NO 29
<211> LENGTH: 705
<212> TYPE: DNA
<213> ORGANISM: Cannabis sativa

<400> SEQUENCE: 29

```
atggcggagc tagaatacca aattaccaaa aacccaactc caaccaccac gcgcttaaaa      60
ctattcggct tcaacgtaca agacgactac gaagaagccg tagctgactc agcaaaaacg     120
acgccgtctg gttcaccgga atccggcaac ggatttcaga actccggtga ccggaaatac     180
gagtgtcagt actgttgtag agaattcgct aattcccaag ccctaggtgg ccatcaaaac     240
gctcataaaa aagaaagaca acagcttaaa cgagctcagc ttcaagcgag ccgaaacgcc     300
gccgttcctt acgctagaaa cccgataatc tcggcttttg cgccgccgcc gcatcttctt     360
tcgccagctg gacaggtaat ggtaccggcg gcttctcctt cgtgggttta tgttccgcgt     420
tcggctcctc cttccacgt gtcgcatggc tgtgtgtttc ctcctgtgat gaacggtggg      480
agaggtgcga gttcagttgg gttatcgtat ggtagcgatg taggggataa ttctacattg     540
acgatgggtt ctcaggttca acaacaacaa caacactcac gggcccataa tttaagggtt     600
gatgggcctt cgttgagtag attttcgaaa ggagatggtg ggcccaattt tgatgatgca     660
ttgggcctgg acttgcatct tagtcttgct cccgctgctc catga                     705
```

<210> SEQ ID NO 30
<211> LENGTH: 357
<212> TYPE: DNA
<213> ORGANISM: Cannabis sativa

<400> SEQUENCE: 30

```
atggcctcaa actcttcaag catgaagcta ctctgcatgg tggtcatggt catggtggta      60
gttgcaccaa cgacacatgc cctaacatgt ggccaagtgt ctagcagtct tagcccatgc     120
atcaactacc tcaagagcgg cggtgctgtc ccttcaccat gttgtaatgg atcaggtcg      180
ctgaacagtg cggccaagac cccagcggac cgcaagactg catgcaagtg cttgcagtct     240
gcggccggca gcatcaaagg actcaactta aacctcgccg cgggacttcc tggaaagtgt     300
ggtgtcaatg ttccatacaa gatcagtccc tccaccaatt gcaacagtgt gcagtga       357
```

<210> SEQ ID NO 31
<211> LENGTH: 521
<212> TYPE: PRT
<213> ORGANISM: Cannabis sativa

<400> SEQUENCE: 31

Met Gly Arg His Ser Cys Cys Tyr Lys Gln Lys Leu Arg Lys Gly Leu
1               5                   10                  15

Trp Ser Pro Glu Glu Asp Glu Lys Leu Leu Asn Tyr Ile Thr Lys His
            20                  25                  30

Gly His Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Pro Phe Ser Gln Gln Glu Asn Leu Ile Ile Glu
65                  70                  75                  80

Leu His Ala Val Leu Gly Asn Arg Trp Ser Gln Ile Ala Ala Gln Leu
                85                  90                  95

Pro Gly Arg Thr Asp Asn Glu Ile Lys Asn Leu Trp Asn Ser Cys Ile

```
            100                 105                 110
Lys Lys Lys Leu Arg Gln Lys Gly Ile Asp Pro Asn Thr His Lys Pro
            115                 120                 125

Leu Ser Glu Val Glu Asn Asp Ile Gly Asn Lys Leu Glu Asn Lys Gly
            130                 135                 140

Asn Lys Ala Ala Thr Asn Asn Asn Asn Glu Asn Ile Asn Asn Ser
145             150                 155                 160

Thr Val Arg Ala Ser Ser Leu Gly Asn Leu Ser Asn Asp His His His
                    165                 170                 175

His His His His His Leu Asn Leu Ala Asp Gln Ser Gln Pro Ser Met
            180                 185                 190

Ala Ala Ile Asn Arg Tyr Pro Leu Leu Glu Val Ser Ser Thr Pro
            195                 200                 205

Pro Thr Gln Glu Phe Phe Ile Glu Lys Ser Thr Asp Thr Arg Ser Ser
            210                 215                 220

Pro Ser Ile Ser Ser Ser Pro Cys Asp Phe Ser Thr Tyr Phe Ser
225             230                 235                 240

Phe His Ser Asn Asn Tyr Asn Thr Thr Ser Ser Ala Ala Ala Ala
                    245                 250                 255

Ala Val Ser His His Gln Asp Gln Asn Asn Asn Asn Met Ala Ser
                260                 265                 270

Phe Cys Phe Asn Ile Asn Gln Asn Ser Thr Arg Pro Pro Gln His His
            275                 280                 285

His His Asn Gln Met Ile Ser Asn Leu Ile Gln Pro Leu Gln Gln Gln
            290                 295                 300

Val Ser Pro Ser Ser Thr Thr Thr Ala Ser Ser Ser Ser Pro Pro Ser
305             310                 315                 320

Asn Ile Pro Arg Val Lys Pro Ser Ile Ser Leu Pro Leu Leu Ser Asp
                    325                 330                 335

His Gln Asn Asn Ser Asn Ser Thr Thr Thr Thr Thr Thr Thr Thr Thr
                340                 345                 350

Gly Ala Val Gln Asn Trp Glu Thr Ser Thr Phe Ser Asn Asn Gly Ser
            355                 360                 365

Ser Ser Ser Ser Cys Asn Ile Glu Leu Gln Gly Asn Asn Asn Asn
370                 375                 380

Asn Asn Asn Phe Phe Asp His Asn Thr Asn Ser Thr Ala Ala Ala
385                 390                 395                 400

Ala Ala Ala Ala Pro Asn Asn Phe Ser Trp Gly Leu Val Asn Glu Ser
                    405                 410                 415

Thr Val Gly Ser Ile Lys Ser Asp Asp Pro Glu Asp Ile Lys Trp Ser
            420                 425                 430

Glu Tyr Leu His Ser Pro Phe Leu Gly Gly Ile Ser Asn Thr
            435                 440                 445

Asn Asn Gln Asn Ser Ser Ser Ser His Leu Gln Pro Ile Leu Tyr
            450                 455                 460

Ser Asn Ile Val Lys Pro Glu Ser His Phe Ser Asn Thr Thr Ala
465                 470                 475                 480

Thr Gly Ser Asn Pro Thr Trp His His Gln Asn Asp His His Gln Leu
                    485                 490                 495

Gln Ala Ala Ser Ser Glu Ile Met Tyr Thr Asn Lys Asp Leu Gln Arg
            500                 505                 510

Leu Ala Val Ala Phe Gly Gln Thr Leu
            515                 520
```

<210> SEQ ID NO 32
<211> LENGTH: 234
<212> TYPE: PRT
<213> ORGANISM: Cannabis sativa

<400> SEQUENCE: 32

Met Ala Glu Leu Glu Tyr Gln Ile Thr Lys Asn Pro Thr Pro Thr Thr
1               5                   10                  15

Thr Arg Leu Lys Leu Phe Gly Phe Asn Val Gln Asp Asp Tyr Glu Glu
            20                  25                  30

Ala Val Ala Asp Ser Ala Lys Thr Thr Pro Ser Gly Ser Pro Glu Ser
        35                  40                  45

Gly Asn Gly Phe Gln Asn Ser Gly Asp Arg Lys Tyr Glu Cys Gln Tyr
    50                  55                  60

Cys Cys Arg Glu Phe Ala Asn Ser Gln Ala Leu Gly Gly His Gln Asn
65                  70                  75                  80

Ala His Lys Lys Glu Arg Gln Gln Leu Lys Arg Ala Gln Leu Gln Ala
                85                  90                  95

Ser Arg Asn Ala Ala Val Ser Tyr Ala Arg Asn Pro Ile Ile Ser Ala
            100                 105                 110

Phe Ala Pro Pro His Leu Leu Ser Pro Ala Gly Gln Val Met Val
        115                 120                 125

Pro Ala Ala Ser Pro Ser Trp Val Tyr Val Pro Arg Ser Ala Pro Pro
    130                 135                 140

Phe His Val Ser His Gly Cys Val Phe Pro Val Met Asn Gly Gly
145                 150                 155                 160

Arg Gly Ala Ser Ser Val Gly Leu Ser Tyr Gly Ser Asp Val Gly Asp
                165                 170                 175

Asn Ser Thr Leu Thr Met Gly Ser Gln Val Gln Gln Gln Gln His
            180                 185                 190

Ser Arg Ala His Asn Leu Arg Val Asp Gly Pro Ser Leu Ser Arg Phe
        195                 200                 205

Ser Lys Gly Asp Gly Gly Pro Asn Phe Asp Asp Ala Leu Gly Leu Asp
    210                 215                 220

Leu His Leu Ser Leu Ala Pro Ala Pro
225                 230

<210> SEQ ID NO 33
<211> LENGTH: 118
<212> TYPE: PRT
<213> ORGANISM: Cannabis sativa

<400> SEQUENCE: 33

Met Ala Ser Asn Ser Ser Ser Met Lys Leu Leu Cys Met Val Val Met
1               5                   10                  15

Val Met Val Val Val Ala Pro Thr Thr His Ala Leu Thr Cys Gly Gln
            20                  25                  30

Val Ser Ser Ser Leu Ser Pro Cys Ile Asn Tyr Leu Lys Ser Gly Gly
        35                  40                  45

Ala Val Pro Ser Pro Cys Cys Asn Gly Ile Arg Ser Leu Asn Ser Ala
    50                  55                  60

Ala Lys Thr Pro Ala Asp Arg Lys Thr Ala Cys Lys Cys Leu Gln Ser
65                  70                  75                  80

Ala Ala Gly Ser Ile Lys Gly Leu Asn Leu Asn Leu Ala Ala Gly Leu
                85                  90                  95

Pro Gly Lys Cys Gly Val Asn Val Pro Tyr Lys Ile Ser Pro Ser Thr
        100                 105                 110

Asn Cys Asn Ser Val Gln
        115

<210> SEQ ID NO 34
<211> LENGTH: 1768
<212> TYPE: DNA
<213> ORGANISM: Cannabis sativa

<400> SEQUENCE: 34

| | | | | | |
|---|---|---|---|---|---|
| atggggaggc | actcttgttg | ttacaagcag | aaactgagaa | aagggttgtg | gtcaccagaa | 60 |
| gaagatgaga | aacttcttaa | ttatataacc | aagcatggac | atggctgctg | gagctctgtc | 120 |
| cctaagctag | ctggtattaa | ttctactatt | actactatca | atgctaataa | tttctgtatg | 180 |
| tttgcatcaa | aattagttac | atatttattc | atcattaatt | ttttatgaca | ggtcttcaga | 240 |
| gatgtggaaa | aagttgcagg | ctaaggtgga | taaattattt | gaggcctgat | ttgaaaagag | 300 |
| gcccattttc | acaacaagag | gagaatttga | taattgaact | tcatgcagtt | cttggcaaca | 360 |
| ggtaattaat | tacttgtttc | ttgagaaaaa | agaagaatga | cattaatttt | gagttgaaat | 420 |
| tcatttctgg | gtacttatgt | aaataatttt | gtgcaaattt | ttcagatggt | cacagattgc | 480 |
| agctcagtta | ccaggaagaa | cagataatga | gattaaaaac | ttatggaatt | cttgcattaa | 540 |
| gaagaaactg | aggcaaaaag | ggattgaccc | aaatactcat | aagccattat | ctgaggtaga | 600 |
| aaatgacatt | ggtaataaat | tggagaacaa | gggtaacaaa | gctgcaacca | ataacaacaa | 660 |
| caatgagaat | attaataatt | ctactgttag | agcttcttca | ttaggaaact | tatccaatga | 720 |
| tcatcatcat | catcatcatc | atcatctgaa | tctagctgac | cagtcacaac | catcaatggc | 780 |
| ggccatcaat | cgttacccac | tattggaagt | ctcatcctca | actccgccga | cacaagaatt | 840 |
| cttcatagaa | aaatcaacag | ataccagatc | atcaccatca | atatcatcat | catcaccttg | 900 |
| tgattttcct | acctacttct | ctttccactc | aaacaattac | aatacgacgt | cgtccgctgc | 960 |
| tgcagctgct | gctgtttctc | atcatcaaga | tcaaaacaac | aacaacaaca | tggccagttt | 1020 |
| ctgcttcaac | attaatcaaa | attcaactag | acctccacaa | caccatcatc | ataatcagat | 1080 |
| gattagtaat | ctcatccagc | cactacaaca | acaagtatca | ccttcatcaa | caacaacagc | 1140 |
| atcatcatca | tcaccaccct | ccaatattcc | acgtgtaaag | ccctccataa | gtctcccctt | 1200 |
| attatctgat | caccaaaaca | acagtaatag | cactactact | actactacaa | caactactgg | 1260 |
| agccgtacaa | aattgggaaa | ctagtacttt | cagcaacaac | ggaagtagta | gtagtagctg | 1320 |
| caatatcgaa | ttacaaggta | ataataataa | caacaacaac | aacttctttg | atcacaacac | 1380 |
| taattccacc | gccgcggccg | ccgccgccgc | cgctcctaat | aacttctcgt | ggggattagt | 1440 |
| caatgaaagt | actgttggta | gcataaaatc | tgatgaccca | gaagacataa | aatggtctga | 1500 |
| atatctccat | agccctttc | ttcttggtgg | aggaattagt | aatactaata | atcaaaattc | 1560 |
| ttcttcttct | tcacatcttc | aacccatttt | gtacagtaac | attgtgaaac | cagaatcaca | 1620 |
| ctttagtaat | actactactg | ctacaggatc | aaaccccacg | tggcatcatc | agaacgatca | 1680 |
| tcatcagcta | caagcggctt | catcagaaat | aatgtacact | aataaagatc | tacagagact | 1740 |
| tgctgtagct | tttggacaga | ccctttag | | | | 1768 |

<210> SEQ ID NO 35
<211> LENGTH: 705
<212> TYPE: DNA

<213> ORGANISM: Cannabis sativa

<400> SEQUENCE: 35

| | | | | | |
|---|---|---|---|---|---|
| atggcggagc | tagaatacca | aattaccaaa | acccaactc | caaccaccac | gcgcttaaaa | 60 |
| ctattcggct | tcaacgtaca | agacgactac | gaagaagccg | tagctgactc | agcaaaaacg | 120 |
| acgccgtctg | gttcaccgga | atccggcaac | ggatttcaga | actccggtga | ccggaaatac | 180 |
| gagtgtcagt | actgttgtag | agaattcgct | aattcccaag | ccctaggtgg | ccatcaaaac | 240 |
| gctcataaaa | aagaaagaca | acagcttaaa | cgagctcagc | ttcaagcgag | ccgaaacgcc | 300 |
| gccgtttctt | acgctagaaa | cccgataatc | tcggcttttg | cgccgccgcc | gcatcttctt | 360 |
| tcgccagctg | gacaggtaat | ggtaccggcg | gcttctcctt | cgtgggttta | tgttccgcgt | 420 |
| tcggctcctc | ctttccacgt | gtcgcatggc | tgtgtgtttc | ctcctgtgat | gaacggtggg | 480 |
| agaggtgcga | gttcagttgg | gttatcgtat | ggtagcgatg | taggggataa | ttctacattg | 540 |
| acgatgggtt | ctcaggttca | acaacaacaa | caacactcac | gggcccataa | tttaagggtt | 600 |
| gatgggcctt | cgttgagtag | attttcgaaa | ggagatggtg | ggcccaattt | tgatgatgca | 660 |
| ttgggcctgg | acttgcatct | tagtcttgct | cccgctgctc | catga | | 705 |

<210> SEQ ID NO 36
<211> LENGTH: 474
<212> TYPE: DNA
<213> ORGANISM: Cannabis sativa

<400> SEQUENCE: 36

| | | | | | |
|---|---|---|---|---|---|
| atggcctcaa | actcttcaag | catgaagcta | ctctgcatgg | tggtcatggt | catggtggta | 60 |
| gttgcaccaa | cgacacatgc | cctaacatgt | ggccaagtgt | ctagcagtct | tagcccatgc | 120 |
| atcaactacc | tcaagagcgg | cggtgctgtc | ccttcaccat | gttgtaatgg | gatcaggtcg | 180 |
| ctgaacagtg | cggccaagac | cccagcggac | cgcaagactg | catgcaagtg | cttgcagtct | 240 |
| gcggccggca | gcatcaaagg | actcaactta | aacctcgccg | cgggacttcc | tggaaagtgt | 300 |
| ggtgtcaatg | ttccatacaa | gatcagtccc | tccaccaatt | gcaacaggta | taaataatta | 360 |
| tgtataaatt | tttaatgatt | aacaattgtt | ttatcaatct | aataacataa | acaaatttat | 420 |
| gttgttactt | atgataatta | ttttattttt | cttaattaat | acagtgtgca | gtga | 474 |

<210> SEQ ID NO 37
<211> LENGTH: 993
<212> TYPE: DNA
<213> ORGANISM: Artemisia annua

<400> SEQUENCE: 37

| | | | | | |
|---|---|---|---|---|---|
| atggccaggc | attccacttg | ttacaaacaa | aggctaagaa | aaggcctttg | gtcaccagaa | 60 |
| gaagatgaaa | aactcatcaa | acacatcacc | aaatttggtc | acggctgttg | gagttctgtc | 120 |
| cctaagctcg | cgggtcttca | agatgcggaa | aagagttgta | ggttacgatg | gattaattac | 180 |
| cttaggcctg | atttgaaacg | aggcacattt | tctcaacaag | aagagacctt | aatcgtagag | 240 |
| ttgcatgcag | tactcggcaa | caaatggtct | cagattgcgg | ctcagttgcc | agggagaaca | 300 |
| gataacgaga | ttaagaactt | atggaactca | tccattaaga | agaagttaag | acaacgaggg | 360 |
| attgatccaa | atactcacaa | accattatcg | gacgtcgaaa | atgaggacaa | accatcacct | 420 |
| agaagtaaca | acaaaaacca | ccaacaaact | attattccaa | gtatagagaa | tccatcacta | 480 |
| gagacacacg | aattcttcag | aaaccgattt | accacaagtc | acgaaaatgc | caacctcgcc | 540 |
| tcccacaccg | acactaaaca | taacaatact | gaccagtttt | caggtttcct | agacttcgct | 600 |

```
tacaaccaac caccacaacc tgaatcaagt ctcttgtttg gctctagctc taacactgac   660
accagtcttt ccaatcccttc ccaacctacc aattgggata caacgacatc tttatttgac   720
gcgaataacg ggtttcataa ccaagttcct ttagttggaa atgaaagcca accagaagac   780
atcaaatgga ataagtatct ccaatcacca tttatgtttg gaggtgctac actccagagt   840
cgggttttgt gtaatgagac aaaacccgac ttgggaatga gtataaatat gaatatgaac   900
ataaataatg agttatatgg gaatcatgaa ggtgtggata catacaacaa gcaattacaa   960
aggatttgtg caagctatgg gcaatttaca tag                                 993
```

<210> SEQ ID NO 38
<211> LENGTH: 330
<212> TYPE: PRT
<213> ORGANISM: Artemisia annua

<400> SEQUENCE: 38

```
Met Ala Arg His Ser Thr Cys Tyr Lys Gln Arg Leu Arg Lys Gly Leu
1               5                   10                  15

Trp Ser Pro Glu Glu Asp Glu Lys Leu Ile Lys His Ile Thr Lys Phe
            20                  25                  30

Gly His Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Thr Phe Ser Gln Gln Glu Thr Leu Ile Val Glu
65                  70                  75                  80

Leu His Ala Val Leu Gly Asn Lys Trp Ser Gln Ile Ala Ala Gln Leu
                85                  90                  95

Pro Gly Arg Thr Asp Asn Glu Ile Lys Asn Leu Trp Asn Ser Ser Ile
            100                 105                 110

Lys Lys Lys Leu Arg Gln Arg Gly Ile Asp Pro Asn Thr His Lys Pro
        115                 120                 125

Leu Ser Asp Val Glu Asn Glu Asp Lys Pro Ser Pro Arg Ser Asn Asn
    130                 135                 140

Lys Asn His Gln Gln Thr Ile Ile Pro Ser Ile Glu Asn Pro Ser Leu
145                 150                 155                 160

Glu Thr His Glu Phe Phe Arg Asn Arg Phe Thr Thr Ser His Glu Asn
                165                 170                 175

Ala Asn Leu Ala Ser His Thr Asp Thr Lys His Asn Asn Thr Asp Gln
            180                 185                 190

Phe Ser Gly Phe Leu Asp Phe Ala Tyr Asn Gln Pro Pro Gln Pro Glu
        195                 200                 205

Ser Ser Leu Leu Phe Gly Ser Ser Asn Thr Asp Thr Ser Leu Ser
    210                 215                 220

Asn Pro Phe Gln Pro Thr Asn Trp Asp Thr Thr Thr Ser Leu Phe Asp
225                 230                 235                 240

Ala Asn Asn Gly Phe His Asn Gln Val Pro Leu Val Gly Asn Glu Ser
                245                 250                 255

Gln Pro Glu Asp Ile Lys Trp Asn Lys Tyr Leu Gln Ser Pro Phe Met
            260                 265                 270

Phe Gly Gly Ala Thr Leu Gln Ser Arg Val Leu Cys Asn Glu Thr Lys
        275                 280                 285

Pro Asp Leu Gly Met Ser Ile Asn Met Asn Met Asn Ile Asn Asn Glu
    290                 295                 300
```

Leu Tyr Gly Asn His Glu Gly Val Asp Thr Tyr Asn Lys Gln Leu Gln
305                 310                 315                 320

Arg Ile Cys Ala Ser Tyr Gly Gln Phe Thr
                325                 330

<210> SEQ ID NO 39
<211> LENGTH: 1485
<212> TYPE: DNA
<213> ORGANISM: Nicotiana tabacum

<400> SEQUENCE: 39

| | | | | | |
|---|---|---|---|---|---|
| atgtcggtct | tgcggttat | ttcattcttt | ctacttctgt | ttttctttt | caaatcatat | 60 |
| ttgccctcat | cgaaaacaaa | gaaaaattct | ccaccatctc | cttcaaagct | tccgttaatc | 120 |
| ggtcacttcc | acaaactagg | cttacaacct | caccgttctc | tacaaaaact | atcaaatgaa | 180 |
| catggtccca | tgatgatgct | tcaattcggt | agcgtacctg | tgcttatcgc | ttcatcagct | 240 |
| gaagctgctt | ccgaaatcat | gaaacccaa | gatttgtctt | ttgcaaacaa | acccatttca | 300 |
| accattccta | gcaagctttt | cttcggccca | aaggacgttg | ccttcacccc | atatggggat | 360 |
| tactggagga | atgccagaag | catttgcatg | cttcagcttt | tgaacaacaa | aagagtccag | 420 |
| tcttttcgaa | agataaggga | agaagagact | tctcttcttc | tccagaggat | tagggaatcg | 480 |
| ccaaattcag | aagtcgattt | aacggagctg | ttcgtttcca | tgactaacga | catagtttgc | 540 |
| agggtggcct | taggaaggaa | gtattgtgat | ggggaagaag | ggaggaaatt | caagtctttg | 600 |
| ctgttagagt | ttgtggaatt | gttgggagtt | tttaacattg | gagattacat | gccgtggctt | 660 |
| gcatggatga | atcgtttcaa | tggtttgaat | gccaaagtgg | ataaagtggc | gaaagagttt | 720 |
| gatgcatttt | tggaggatgt | gattgaggaa | cacggaggaa | ataagaaatc | agacactgaa | 780 |
| gctgaagggg | cagacttcgt | ggatatatta | ttgcaggttc | acaagaaaaa | caaggctggt | 840 |
| tttcaagtcg | aaatggatgc | aatcaaagct | attatcatgg | atatgtttgc | tgcgggaaca | 900 |
| gatacaactt | ccacgcttct | agagtggaca | atgaacgagc | tcttaagaaa | tccaaaaaca | 960 |
| ttgaataagt | tgagagatga | ggtgagacaa | gtgactcaag | ggaagacaga | ggtaacagag | 1020 |
| gatgacttag | agaaaatgcc | gtatttaaga | gcagcagtta | aggagagttc | caggctacac | 1080 |
| tctccagtgc | cacttctacc | tcgagaagca | attaaggatg | caaaggtttt | gggctacgat | 1140 |
| atagctgcag | ggactcaagt | cctcgtttgt | ccatgggcaa | tctcaagaga | tccaaacctt | 1200 |
| tgggaaaatc | cagaggagtt | tcaacctgaa | agattcttgg | atacttccat | agattacaaa | 1260 |
| ggcttacatt | tcgagttaat | tccattcggt | gcaggtcgga | ggggttgccc | tggcatcaca | 1320 |
| tttgctaagt | ttgtgaatga | gctagcattg | gcaagattaa | tgttccattt | tgatttctcg | 1380 |
| ctaccaaaag | gagttaagca | tgaggatttg | gacgtggagg | aagctgctgg | aattactgtt | 1440 |
| agaaggaagt | tcccccttttt | agccgtcgcc | actccatgct | cgtga | | 1485 |

<210> SEQ ID NO 40
<211> LENGTH: 966
<212> TYPE: DNA
<213> ORGANISM: Nicotiana tabacum

<400> SEQUENCE: 40

| | | | | | |
|---|---|---|---|---|---|
| atggcagaaa | aaatcaccag | ccacgagaac | acaaggtatg | cagtggtgac | agggggaaat | 60 |
| aaaggaatag | gatatgaaac | atgcaggcaa | ctagcaaagg | aaggaatagt | ggtagtgttg | 120 |
| acagcaaggg | atgaaaggag | aggaattgaa | gctctcgaaa | agctcaagga | agagtactca | 180 |

```
agcaataaaa ctgatgatga tcagatttta tttcatcaac ttgatgttat ggatccagct    240
agtatttctt ctcttgtgga cttcatcaaa actaaatttg gaaagctcga tattctggtt    300
aacaacgcag ggattggtgg attaatggta gaaggagatg ttgttataat aaaagattta    360
atagaaggag acttcgtaac catttctgct gaaaatgggg aagaggatgg tattaagaaa    420
tcaattgaag gtattgagcg tattgttaca gattatgagt tgacaaaaca atgcctggag    480
acaaacttct atggtgcaaa agaatgatt gaagcattta ttcccctcct tcagctctct     540
aactccccaa gaattgttaa tgtcgcttct ttcttgggga agttaaagct attgtgcaac    600
caatgggcta taggaatgct aagtgatgct aaaagcctga gagaagaaag ggtggatgaa    660
gtgttgaatg aatttataaa agattttaaa gagaaatcaa tagaagccaa aggatggcca    720
acttatttct cagcttacaa agtctcgaaa gcatccctga ttgcttacac aagggtttta    780
gctacgaaat atccaaattt tcggataaat tctgtgtgtc ctggattttg caaaacagac    840
gtgaactgca atactgggag cttaactgct gaagaaggtg ctgaaagctt ggtgaagctt    900
gctttggtgc caaatgatgg accctctggt ctcttctttt atagaaagga ggtcacctct    960
ttttga                                                               966
```

<210> SEQ ID NO 41
<211> LENGTH: 1797
<212> TYPE: DNA
<213> ORGANISM: Nicotiana sylvestris

<400> SEQUENCE: 41

```
atgagtcaat caatttctcc attaatctgt tctcactttg cgaaatttca gtcgaatatt     60
tggagatgca atacttctca actcagagtt atacactcat catatgcctc ttttggaggg    120
agaagaaaag agagagtaag aagaatgaat cgagcaatgg atctttcttc aagctctcgt    180
catttggcag attttcccctc aacaatttgg ggtgaccatt ttctctccta caattctgaa    240
ataacagaaa ttactaccca agagaaaaat gaacatgaaa tgctaaaaga atagttcgg     300 aaaatgttgg tagaaactcc agataatagt acacaaaaac tagtcttgat tgacacaatt    360
caaagattgg gattagcata tcatttcaat gatgagattg aaaactccat tcaaaacatc    420
tttaatttgt ctcaaaatag tgaagatgac gatgaacaca cctttatgt tgctgctctt     480 cgttttcgac ttgcgaggca acaaggatat tacatgtctt cagatgtgtt caagcaattc    540
actaaccatg acggaaaatt caaggaaaat catactaatg atgttcaagg attattgagt    600
ttgtatgaag cagcacatat gagagtgcac gacgaggaaa ttctagaaga agctcttatc    660
tttaccacga ctcatctcga gtccgtgatc ccgaatttga gcaactcgct taaggtacaa    720
gttactgaag ccttaagcca tcctattcgc aaagctatac caagggtggg agcaaggaaa    780
tacatacaca tatgaaaa cattggaaca cataatgatt actttttgaa atttgcaaag     840
ttggacttca acatgttaca aaagcttcat cgaaaagagc ttaacgagct aacaagctgg    900
tggaaagatt tggatcgtgc aaacaaattt ccatatgcaa aggacagatt agtagaagct    960 tactttttgga cggtgggaat atattttgaa cctcaatata gtcgttcaag aagtttggta   1020
acaaaagtag tcaaaatgaa ctccattatt gatgacactt atgatgctta tgcaactttt   1080
gatgagcttg tgcttttcac ggatgcgatc caaagatggg acgaaggtgc catggattta   1140
ttaccgacat atctgagacc tatttatcaa ggccttctcg acgttttcaa tgaaatggaa   1200
gaagtattgg ccaagaagg taagcagat cacatctact atgcgaaaaa agagatgaaa    1260
aaggtggcgg aagtctattt taaggaagct gaatggttga atgctaacta cattccaaaa   1320
```

```
tgcgaggagt atatgaaaaa tggacttgta agctctaccg gtccgatgta tggaataatt    1380
tctttggttg ttatggagga aattataaca aaagaggctt ttgaatggtt gacaaatgaa    1440
cctttgattc ttcgagctgc atcaacaatt tgtagattaa tggatgatat ggctgatcat    1500
gaagttgaac aacaaagagg acatgttgct tcatttgttg agtgctacat gaagaatat    1560 ggagtttcaa agcaagaagc atatgttgag atgcggaaaa aaatcacaaa tgcgtggaaa    1620
gatataaata aggaactctt gcgccctact gcagtaccaa tgtttatcct cgaacgatct    1680 ttaaatttt caagattggc cgatacattt ttgaaagatg atgatggata cacaaatccc    1740
aaatccaaag ttaaagactt gattgcttcg ttgtttgtcg aatctgtcga catatga      1797
```

<210> SEQ ID NO 42
<211> LENGTH: 1098
<212> TYPE: DNA
<213> ORGANISM: Nicotiana tabacum

<400> SEQUENCE: 42

```
atggcatttt tggctaccat ttctggccat gaaaatatgc ttcttccaa taccctaaac     60 aataacttta ttttcagtgg aaaacctcca cagagacatt cttatagttt cctccccaag   120
aaaatccagg ccagaagtgt tgcaaactca tccaaaacat ttcaagtcaa agaagaagaa   180
ttctcatcta agacagagaa attcatcttg cctaagtttg actttgaaga atatatgaaa   240
atgaaggcaa ttaaggtaaa caaagcacta gatgatgcaa taccaatgca agagcctata   300
aaaattcatg aagccatgag atactcactt ctagctgggg aaaacgcgt ccggccgatc    360 ctatgcatgg cttcttgtga agtagtagga ggggatgaat ccttagctat tcctgcagct   420
tgctcggttg agatgatcca caccatgtca ctcatccacg acgatcttcc ttgcatggac   480
aacgatgatc tacgtcgtgg caagcccacg agccacaagg ctttcgggga agacactgca   540
gttctaacag gggatgcact tttgtctttg gcctttgaac atgtagcttc caagactaaa   600
gatgtgacac cccaaagagt ggttcaagcc gttggcgaat gggttcagc cgttggctcg    660 aaagggcttg tggcggggca gattgtggac atagctagtg agggaaaaca agtgagccta   720
actgaattag agtacattca caaccataag acagggaaac tattggaggc tgctgtggtt   780 tgtgggggcaa taattggggg agggaatgag attgaggtgg agagaatgag gaactatgct   840
agatgccttg gactgttgtt tcaagtggta gatgatattc ttgatgttac taagtcatca    900
gaagagttgg gaaagacagc tggtaaagac ctagtgactg ataaggctac atatcctaag    960
ttgatggggc tagaaaaagc tcgggagctc gccggagagc tggtggctaa ggccatggat   1020
gagctgagct actttgatgc tgccaaggcg gcacctcttt atcattttgc taattatatt   1080
gcacatcgcc agaattga                                                  1098
```

<210> SEQ ID NO 43
<211> LENGTH: 2379
<212> TYPE: DNA
<213> ORGANISM: Nicotiana sp.

<400> SEQUENCE: 43

```
atggtacttg gactgagaag caaaatcata ccacttcctg atcataagtt gggaaatatc     60
aaattaggtt cagtaaccaa tgcaatttgc cacagaccat gtagagtaag atgcagccac   120
agtactgctt catcaatgga agaggcaaag gagagaataa gggaaacatt tggaaaaata   180
gagctatctc cttcttccta tgacacagca tgggtagcta tggtcccttc aagatattct   240
```

```
atgaaccaac catgttttcc tcagtgctta gattggattc ttgaaaatca aagagaagat   300
ggatcttggg gcctaaatcc tagccatcca ttgcttgtaa aagactccct ttcttccact   360
ctagcatctt tgcttgccct tcgcaaatgg agaattggag ataaccaagt ccaaagaggc   420
cttggcttta ttgaaacgca tggttgggca gtcgataaca aggatcagat ttcaccttta   480
ggatttgaaa ttatatttcc ctgcatgatc aactatgcag agaaacttaa tttggatcta   540
cctttggatc ctaaccttgt aaatatgatg ctctgcgaac gtgaattaac aattgaaaga   600
gccttaaaga atgaattcga ggggaatatg gcaaatgtag aatattttgc tgaagggctc   660
ggtgaattat gtcattggaa agagatgatg cttcgtcaga gacacaacgg gtcgctcttt   720
gattcaccag ccactactgc agctgccttg atttaccatc agtacgatga gaaatgcttt   780
gggtacttga actcaatctt gaaactgcac gataattggg tccccactat ttgccctaca   840
aagatacatt caaatctctt cttagttgat gcccttcaaa atcttggagt agatcggtat   900
tttaaaacag aagtcaaaag agtactagat gaaatataca ggctttggct agaaaagaat   960
gaagaaattt tttcagacgt tgctcattgt gccatggcgt ttcgactttt acggatgaat  1020
aactatgaag tttcctcaga gaacttgaa ggatttgtcg accaagaaca tttctttaca   1080
acatcaagtg ggaaacttat gaatcacgtt gcaattctcg aacttcaccg agcttcacag  1140
gtggctattc atgaaaggaa agatcacatt ttagataaaa taagtacttg acaaggaat  1200 tttatggagc aaaaactctt ggacaagcac atccctgata ggtcaaagaa ggagatggaa  1260
tttgctatga ggaaattta tggcacattt gatcgagtgg aaactagacg ttacatcgag  1320
tcatacaaaa tggacagttt taagatctta aaagcggctt acaggtcttc cggtattaac  1380
aacatagact tgctaaagtt ctcagaacac gatttaaact tgtgccaaac ccgacacaaa  1440
gaagaacttc aacagatgaa aaggtggttc acagattgca aactcgaaca agtaggatta  1500
tcacaacagt acttatacac tagttacttc ataattgctg ccatactctt tgaacctgaa  1560
tatgctgatg ctcgtctagc atatgcaaag tacgccataa aataacagc ggtggatgat   1620 ttcttcgatt gttttatttg caaagaagaa ctgcaaaaca tcatcgaatt agtagagaga  1680
tgggagggat actcaaccgt cggattccgt tcagagaggg ttagaatttt cttttttggca  1740 ctttacaaaa tggtagagga aattgcggca aaggcggaaa ctaagcaagg tcgatgtgtc  1800
aaagatcacc ttattaactt gtggattgat atgttgaagt gtatgctggt ggaattggac  1860
ctttggaaaa ttaaatcaac taccccaagc atagaggagt acttgtctgt tgcatgtgta  1920
actattggtg ttccatgttt tgttctcaca tcactatatc ttcttggacc aaaactgtcc  1980
aaggatgtca tagaaagttc tgaggtcagt gccttatgca attgtacagc tgctgtggcc  2040
cgattgatta tgatatataca cagttacaag agagaacaag cagaaagttc aacaaatatg  2100
gtatcaatat taataacaca aagtcaggga actatctctg aagaagaggc tataagacag  2160
ataaaggaaa tgatggaaag taagagaaga gagttgctag ggatggttct acaaaataaa  2220
gaaagccaat tgccacaagt gtgcaaggat cttttttgga cgacaatcaa cgcagcttat  2280
tctatacata cacatggcga tgggtatcgc ttcccagagg aattcaagaa ccatatcaac  2340
gatgtaattt acaaaccact caatcaatat tccccataa                         2379
```

<210> SEQ ID NO 44
<211> LENGTH: 1792
<212> TYPE: DNA
<213> ORGANISM: Nicotiana sp.

<400> SEQUENCE: 44

```
atgtcggtct tgcggttat ttcattcttt ctacttctgt tttttctttt caaatcatat      60
ttgccctcat cgaaacaaa gaaaaattct ccaccatctc cttcaaagct tccgttaatc     120
ggtcacttcc acaaactagg cttacaacct caccgttctc tacaaaaact atcaaatgaa    180
catggtccca tgatgatgct tcaattcggt agcgtacctg tgcttatcgc ttcatcagct    240
gaagctgctt ccgaaatcat gaaaacccaa gatttgtctt ttgcaaacaa acccatttca    300
accattccta gcaagctttt cttcggccca aaggacgttg ccttcacccc atatggggat    360
tactggagga atgccagaag catttgcatg cttcagcttt tgaacaacaa aagagtccag    420
tcttttcgaa agataaggga agaagagact tctcttcttc tccagaggat tagggaatcg    480
ccaaattcag aagtcgattt aacggagctg ttcgtttcca tgactaacga catagtttgc    540
agggtggcct taggaaggaa gtattgtgat ggggaagaag ggaggaaatt caagtctttg    600
ctgttagagt ttgtggaatt gttgggagtt tttaacattg gagattacat gccgtggctt    660
gcatggatga atcgtttcaa tggtttgaat gccaaagtgg ataaagtggc gaaagagttt    720
gatgcatttt tggaggatgt gattgaggaa cacggaggaa ataagaaatc agacactgaa    780
gctgaagggg cagacttcgt ggatatatta ttgcaggttc acaaagaaaa caaggctggt    840
tttcaagtcg aaatggatgc aatcaaagct attatcatgg tatgtgtata tatatatcac    900
tggcattcaa ctttaaactt tcattttact cattttactc ttgatgagaa gcatttataa    960
tcacataaat gtcatgtccc cacaaaacat ttacccctta aacttctaag aacacaactt   1020
tcaaaaaata aaatttttca taaatttcgt gtcgagtcaa actaagtcat gatctaattt   1080
gaaatggaag gagcatataa ttaccctcta acgaacaaa ttaaactgaa agagaaaact    1140
atatattgta tttgatttac atgtgctaat taattgtttg atgcaggata tgtttgctgc   1200
gggaacagat acaacttcca cgcttctaga gtggacaatg aacgagctct taagaaatcc   1260
aaaaacattg aataagttga gagatgaggt gagacaagtg actcaaggga agacagaggt   1320
aacagaggat gacttagaga aaatgccgta tttaagagca gcagttaagg agagttccag   1380
gctacactct ccagtgccac ttctacctcg agaagcaatt aaggatgcaa aggttttggg   1440
ctacgatata gctgcaggga ctcaagtcct cgtttgtcca tgggcaatct caagagatcc   1500
aaacctttgg gaaatccag aggagtttca acctgaaaga ttcttggata cttccataga    1560
ttacaaaggc ttcatttcg agttaattcc attcggtgca ggtcgaggg gttgccctgg    1620 catcacattt gctaagtttg tgaatgagct agcattggca agattaatgt tccattttga   1680
tttctcgcta ccaaaaggag ttaagcatga ggatttggac gtggaggaag ctgctggaat   1740
tactgttaga aggaagttcc ccttttagc cgtcgccact ccatgctcgt ga            1792
```

<210> SEQ ID NO 45
<211> LENGTH: 3575
<212> TYPE: DNA
<213> ORGANISM: Nicotiana sp.

<400> SEQUENCE: 45

```
atggcagaaa aaatcaccag ccacgagaac acaaggtatt tacaaacctt gttatgtcta      60 ttaagttta tgtactgata gtaaaaatt atttacggaa tcagtacggt tattaggtaa     120
ttataggtaa atctctacta taagcatagt agtaatattt aagttgtatg atcgatcagg    180
tatgcagtgg tgacagggg aaataaagga ataggatatg aaacatgcag gcaactagca    240
aaggaaggaa tagtggtagt gttgacagca agggatgaaa ggagaggaat tgaagctctc    300
```

```
gaaaagctca aggaagagta ctcaagcaat aaaactgatg atgatcagat tttatttcat        360
caacttgatg ttatggatcc agctagtatt tcttctcttg tggacttcat caaaactaaa        420
tttggaaagc tcgatattct ggtactattc actactatta tatttatcac cccatcactt        480
aaatctaggg ctaagttggt tgggttagtg atttcccacg tgagagacct tagatccatt        540 ttttcccag cagccttctc ctcgcgctgg gatgtctagt gcaatttata ttttctatgt         600
gatttgcgaa ctattgcaca gtaaataggg gcacacatcc gaagggtagc ggctgctgaa        660
cctgagaatt ttccccaaa atatcgttta gaaaaaaca agaagtcatc tattattact          720
tttttccaga tccattcttc ctgtttcaat ggatgaagta ttaactaatt aaatgagcca        780
tttaaggaaa gataaagggt gattaaataa ttactagtat taaatgactc tcttaagggg       840
tgtgtaaaac cccataaaaac aataacatgt gctggaggga acagtaattt tattgtcagt       900
atggtaaagc ttcgtatatt tttctattta cttgtactga attcttgatg ttttcatgtt       960
agagatatat gaagtttaac cctgcaaaat gttatgcatg tggtaaatat tattacagaa       1020
ctaggatatt ttggctgact ggcttatccc tcgttagaaa tgaatactgc aaagctccat       1080
atctatgtag ttaatcaagt cgcaatgcat ctataccgta gagtgcaatt tatcttactc       1140
ctatatactc tactcgcttc ttcgtgtacg taataagtaa ttttttagct ttttagcata       1200
tctcactctt agaaaaaagt attttgatta aattaccttta attaaacttg catattgtta      1260
acttgacatc ttgaaataag aaaataagga attttttatt taaaaataac attaatactt       1320
gttgataata tgaaaaccaa aataaaaaga tttgtagctc tattcagtga tcagtagcca       1380
aagaaagaaa ggtcgaggag gtgaaaaagg tataggggtcc ttgagatcta caaaagttgg      1440
tgaacagtga catgcaatct aatttatttta ggattaacat ttcttttcca agtgaggaag      1500
cccatcagtt gttagatggc cccttgagat ctacaaaata gattcttttt gtgcaaaaga      1560
taatattcat taattaaatg tatgcgtacc gagagagtgg tgcgtagctt gcaccatatt       1620
acaaagtact aaactattac ttgtatcttc tacagaatag gtaacttatg gttatcatag       1680
gaattacttg tactttttttt atgatagtgt aaatatttct ttattatcga tgtataatta     1740
taaactcgct cacaaattag tgaaataaga tataacttat gggtacagag tcgtacttaa      1800
cattgaaatt gtaagatata cgattaatat tttattaaat ttcctacatc tttttttcagt    1860 gctataggtt gtcttagcaa ggtagtcatg agggacaaaa tattttagtg ctaattagtt      1920
ttggttttaa tctcttgggg tcgtttggta gagaacaagt tatcccgaga ttataatgat       1980
gaaaattata atacagaaat taaataatga tgagattatt tagtgaatat atttttattg     2040
gactaaaaat ggggtacatg ggtacatatt tcatatatgc tttacttaga aataagaaat       2100
tatgaatgct tcaatttaat ttgcaggtta acaacgcagg gattggtgga ttaatggtag       2160
aaggagatgt tgttataata aaagatttaa tagaaggaga cttcgtaacc atttctgctg      2220 aaaatgggt aagatatata gccaatgcta atatgttatc ctaaattaat tagaaacagt        2280
caatggtgat ctctttgata attttcagtt atttatgtc acaaatacat tcaaagaaat      2340
agtaacaaat tgaagtaatt attatgcagg aagaggatgg tattaagaaa tcaattgaag      2400
gtattgagcg tattgttaca gattatgagt tgacaaaaca atgcctggag acaaacttct      2460
atggtgcaaa aagaatgatt gaagcattta ttccctcct tcagctctct aactccccaa      2520
gaattgttaa tgtcgcttct ttcttgggga agttaaaggt aatgaaatca taactgaata       2580
ctatttcata atatatggac cctctgaatt atgttgagtt taatttctac atacttataa       2640
tagtggtagc aaatggcctg tttgggctga tcaagataga ttgactcatt gcccaattct      2700
```

```
gcctaaatgg ttaagatagg ctaaacacaa cccatccaaa ttgacccaaa tctttgcaat    2760
attttcaact tttaaacaag cattataaaa tattcttaca tatataataa tattttcgt     2820 aaatatcatt ttggaatggt ttacgatgat gattttttt ttcttttttt cctgttactt     2880
gtcttatgtt ttgaaaaaat gttaatttat gcctaatgat ttatttcctc aatttcgatt    2940
taaaacttta tttgatagtt ccttatcgta taatactaac aaaaatcaga ataataaaaa    3000
agtagtaaat catgggttga tctgggctac tgaaaataaa tgggcttagt tgggttgtgc    3060
ccaaatttag cccatcacta aagtagctta tgtccaaccc actaaaacct aacggattgg    3120
gcgggtcaaa tgggtttgtg caacttttgc caccctaagt gatagtgtac tcctaaccgt    3180
tttccgctat tctacagcta ttgtgcaacc aatgggctat aggaatgcta agtgatgcta    3240
aaagcctgag agaagaaagg gtggatgaag tgttgaatga atttataaaa gattttaaag    3300
agaaatcaat agaagccaaa ggatggccaa cttatttctc agcttacaaa gtctcgaaag    3360
catccctgat tgcttacaca agggttttag ctacgaaata tccaaatttt cggataaatt    3420
ctgtgtgtcc tggattttgc aaaacagacg tgaactgcaa tactgggagc ttaactgctg    3480
aagaaggtgc tgaaagcttg gtgaagcttg ctttggtgcc aaatgatgga ccctctggtc    3540
tcttctttta tagaaaggag gtcacctctt tttga                              3575
```

<210> SEQ ID NO 46
<211> LENGTH: 4497
<212> TYPE: DNA
<213> ORGANISM: Nicotiana sp.

<400> SEQUENCE: 46

```
atgagtcaat caatttctcc attaatctgt tctcactttg cgaaatttca gtcgaatatt      60
tggagatgca atacttctca actcagagtt atacactcat catatgcctc ttttggaggg     120
agaagaaaag agagagtaag aagaatgaat cgagcaatgg atctttcttc aagctctcgt     180
catttggcag attttccctc aacaatttgg ggtgaccatt ttctctccta caattctgaa     240
ataacagtaa gtcacaatcc catgcttata ttctaccgtc aaacttctct ataacaactc     300
catttgttgc gatcgttttt tattgttata gtgaagtgtt gttatagaga ttatatatta     360
taatataaca tagtaatcgg ttccgagaaa acttgattct ttagtgaatg actgttatat     420
ggggatgtta tagagaggtc tgactgtgtt acctaaatga ataatgaaga tgttataatt     480
ttattagaga tggatgaagc atttaaacat gaaagattca agcttaagaa ttggtcttta     540
tcgtactttt gaaattatga gtttggaatt taatacttcc tccgtctcaa aaagaatga     600 atcttttact atatggggtc aaataagatt ttctttggcc atattttttg caaatgcatt     660
tcaaatattt tgaatttta attgttgtga cttacaatac cttttatgca gtttctaaat     720
gtgtaaaata tatttcaaaa catttaaaga atatatgttc atcacattaa aaaatattga    780
acttgactct catgctccga caaggtttaa ataaattgaa acgaatggaa tattactatt     840
ttgtaaaaac ttaggtaggt tttcactata tatctaataa tgtattcaaa actcataaat     900
aatgatcaaa aggagccttg tgaccgggag gtcacgggtt cgagccgtgg aaacaacctc     960
ttgcaaaaat gtaaggtaag actgcataca atagactctt gtggtccgcc ccttctccgg    1020
accccgcaca tagcggaagc ttattgcact aggctgccct ttttagtgat taacatatgt    1080
ggatctagga tttaaatttt ttgggttcaa ccttttaagga tctgttacaa ttttagtaga    1140
atgttacaca taaatttgtg ctccgtgaat gtattgagtc agatgaacct ggtattatac    1200
```

-continued

```
atgcggatac gctcctgatg ctcaatttct gcctgcagga aattactacc aagagaaaa    1260
atgaacatga aatgctaaaa gaaatagttc ggaaaatgtt ggtagaaact ccagataata    1320
gtacacaaaa actagtcttg attgacacaa ttcaaagatt gggattagca tatcatttca    1380
atgatgagat tgaaaactcc attcaaaaca tctttaattt gtctcaaaat agtgaagatg    1440
acgatgaaca caacctttat gttgctgctc ttcgttttcg acttgcgagg caacaaggat    1500
attacatgtc ttcaggtacc ttacatttct gcccttttcc cgcacagctt atttttttc     1560
gttgttaaaa gacagttcgg cgcataaaat atctcatgta tacgcagggt caggacgaac    1620
cgcccccaag gggtgtaaag tatgcaactt accctaatac taaatatctc gtgtatacac    1680
agggtcagga caagtcgcac ccaaggggtg taatgtagac aacttatcct aatgctatta    1740
gtaactgatt ttatggctcg aacacataaa ttataggtca cacagtaaca actttaccgt    1800
tgctcaaaga ctcgccttcc tcttttttta gttatcgcac cttatttgtg cagagaatag    1860
caagtttcga gatctgcttc tatatagaag acttctgtat tatacttttt tattttgtcc    1920
ttctgcttaa aaatagtaaa aaactatagt gtggaaattg taaatttctt aactagctgt    1980
gaaatcaaat agttattata ggaatattat ttaagactcc acttatggaa aaccactggg    2040
ttgttgttgt tattgtcaat aataacttgg ggtacgattt acttctttt ccatggcttg      2100
tccacgacta tatttctatt aacaatgttg tgactatgct ttctttgagt cgagggtcta    2160
ttgataacag gctctcgatc tttacaaggt aaaagtaatg tctgcgtaca cactctactc    2220
cgcagactcc acttgtagga tttcactgaa tatttttgt tgttgttgtt gttgtaataa      2280
cttagggttt aatttcttga tgctaatgaa attcatttct ttcaaaatat aaacatggtg    2340
ttcaaccaga tgtgttcaag caattcacta accatgacgg aaaattcaag gaaaatcata    2400
ctaatgatgt tcaaggatta ttgagtttgt atgaagcagc acatatgaga gtgcacgacg    2460
aggaaattct agaagaagct cttatcttta ccacgactca tctcgagtcc gtgatcccga    2520
atttgagcaa ctcgcttaag gtacaagtta ctgaagcctt aagccatcct attcgcaaag    2580
ctataccaag ggtgggagca aggaaataca tacacatata tgaaaacatt ggaacacata    2640
atgatttact tttgaaattt gcaaagttgg acttcaacat gttacaaaag cttcatcgaa    2700
aagagcttaa cgagctaaca aggtacatct actattcttg tcatcttcat aattatggta    2760
caatcagacc tctctataaa atacatcctt tataacaaca gttcactata acggtcaagt    2820
tttcttaaaa atcaatgttt tatgttacca aattattttg aaagaaatgt gactattata    2880
gagaggtttg actgtaactc gcgctaatta ataacaccta agtttaagt atgttaatgc       2940
tgttatgata tctatagctg gtggaaagat ttggatcgtg caaacaaatt tccatatgca    3000
aaggacagat tagtagaagc ttacttttgg acggtgggaa tatattttga acctcaatat    3060
agtcgttcaa gaagtttggt aacaaaagta gtcaaaatga actccattat tgatgacact    3120
tatgatgctt atgcaacttt tgatgagctt gtgcttttca cggatgcgat ccaaaggtaa    3180
aattatatat aataaaatct ttctataaca acgtcattta ttctgatatt tttttaagat     3240
gctatagtga agtattgtta tatagaaata tattatgaca acttagactt tgcagatggg    3300
acgaaggtgc catggattta ttaccgacat atctgagacc tatttatcaa ggccttctcg    3360
acgttttcaa tgaaatggaa gaagtattgg ccaaagaagg taaagcagat cacatctact    3420
atgcgaaaaa agaggtaatc cttgattaag ttacattaat tactacttaa tagttaatta    3480
agtaaaccaa gttgtaggga agaatcgcaa ttttgaacta ttagtacatt ttctgttact    3540
tttttagatg aaaaaggtgg cggaagtcta ttttaaggaa gctgaatggt tgaatgctaa    3600
```

-continued

```
ctacattcca aaatgcgagg agtatatgaa aaatggactt gtaagctcta ccggtccgat    3660
gtatggaata atttctttgg ttgttatgga ggaaattata acaaagagg cttttgaatg     3720 gttgacaaat gaacctttga ttcttcgagc tgcatcaaca atttgtagat taatggatga    3780
tatggctgat catgaagtaa gtataacaat ataattttca ttttatataa caatagccat    3840
cgtaattcgc gaattttgtc cctaaataca atacaaaaac aactacaata acaaaaacaa    3900
catatccaat atattcctac agtacgggtc taggaagaga gatgtgtacg cagatcttac    3960
cctaccttat agaggtagaa atgttgttcc cgatagaccc tcgactcaaa aaaagcattt    4020
ctcagtctga tttcgagtct aggtggcact tttgcatgat aaaataaata gacatgcttg    4080
ataaattaca acttcaatga tcacatttac ttaaactgaa ttatggaact ttagaaacgg    4140
ctgattaaaa tggtaaaata ttgtataata ttaatgaaga aattgaaata tattatgttg    4200
taggttgaac aacaaagagg acatgttgct tcatttgttg agtgctacat gaaagaatat    4260
ggagtttcaa agcaagaagc atatgttgag atgcggaaaa aaatcacaaa tgcgtggaaa    4320
gatataaata aggaactctt gcgccctact gcagtaccaa tgtttatcct cgaacgatct    4380 ttaaatttt caagattggc cgatacattt ttgaaagatg atgatggata cacaaatccc     4440
aaatccaaag ttaaagactt gattgcttcg ttgtttgtcg aatctgtcga catatga       4497
```

<210> SEQ ID NO 47
<211> LENGTH: 1098
<212> TYPE: DNA
<213> ORGANISM: Nicotiana tabacum

<400> SEQUENCE: 47

```
atggcatttt tggctaccat ttctggccat gaaaatatgc ttcttttccaa tacccctaaac   60 aataacttta ttttcagtgg aaaacctcca cagagacatt cttatagttt cctccccaag    120
aaaatccagg ccagaagtgt tgcaaactca tccaaaacat ttcaagtcaa agaagaagaa    180
ttctcatcta agacagagaa attcatcttg cctaagtttg actttgaaga atatatgaaa    240
atgaaggcaa ttaaggtaaa caaagcacta gatgatgcaa taccaatgca agagcctata    300
aaaattcatg aagccatgag atactcactt ctagctgggg gaaaacgcgt ccggccgatc    360
ctatgcatgg cttcttgtga agtagtagga ggggatgaat ccttagctat tcctgcagct    420
tgctcggttg agatgatcca caccatgtca ctcatccacg acgatcttcc ttgcatggac    480
aacgatgatc tacgtcgtgg caagcccacg agccacaagg ctttcgggga agacactgca    540
gttctaacag gggatgcact tttgtctttg gcctttgaac atgtagcttc caagactaaa    600
gatgtgacac cccaaagagt ggttcaagcc gttggcgaat tgggttcagc cgttggctcg    660
aaagggcttg tggcggggca gattgtgac atagctagtg agggaaaaca agtgagccta    720
actgaattag agtacattca caaccataag acagggaaac tattggaggc tgctgtggtt    780
tgtggggcaa taattggggg agggaatgag attgaggtgg agagaatgag gaactatgct    840
agatgccttg gactgttgtt tcaagtggta gatgatattc ttgatgttac taagtcatca    900
gaagagttgg gaaagacagc tggtaaagac ctagtgactg ataaggctac atatcctaag    960
ttgatggggc tagaaaaagc tcgggagctc gccggagagc tggtggctaa ggccatggat   1020
gagctgagct actttgatgc tgccaaggcg gcacctcttt atcattttgc taattatatt   1080
gcacatcgcc agaattga                                                 1098
```

<210> SEQ ID NO 48

-continued

<211> LENGTH: 9552
<212> TYPE: DNA
<213> ORGANISM: Nicotiana sp.

<400> SEQUENCE: 48

| | | | | | |
|---|---|---|---|---|---|
| atgatacttg | gactgagaag | caaaatcata | ccacttcctg | atcataagtt | gggaaatatc | 60 |
| aaattaggtt | cagtaaccag | taagacacat | aattttttatt | actatacgtt | acaagaagat | 120 |
| aagtatcatt | caattctttt | ataactaatt | tcagtctctt | ttttgataaa | atttctgtgt | 180 |
| ctccttgttc | gaagaagatg | caatttgcca | cagaccatgt | agagtaagat | gcagccacag | 240 |
| tactgcttca | tcaatggtat | gctatttctt | tttgcataca | aatttagcca | actggagtaa | 300 |
| ctgagacaga | attttaaaaa | gtggcctaga | aaaggccatt | tgtgtaaatg | cccttaataa | 360 |
| agcaatggtg | gttgcaggaa | gaggcaaagg | agagaataag | ggaaacattt | ggaaaaatag | 420 |
| agctatctcc | ttcttcctat | gacacagcat | gggtagctat | ggtcccttca | agatattcta | 480 |
| tgaaccaacc | atgttttcct | cagtgcttag | attggattct | tgaaaatcaa | agagaagatg | 540 |
| gatcttgggg | cctaaatcct | agccatccat | tgcttgtaaa | agactcccctt | tcttccactc | 600 |
| tagcatcttt | gcttgccctt | cgcaaatgga | gaattggaga | taaccaagtc | caagaggta | 660 |
| aatgacaccg | agtttagaag | aacgatttct | ttgaaatttg | tggttgtaaa | tatgcaatga | 720 |
| tattttttg | gttataaaac | aaaaaattta | aagttaaatt | ttatccaaat | atataaaggt | 780 |
| gtcactcatt | ttaaaactga | cctgaagaaa | ttacatcatt | tgaattaatt | ttttctgtgt | 840 |
| agtgtcagaa | tattaaaatt | ttaattgttt | acaaatcagt | tatatatctt | agtgtagctt | 900 |
| agctccaaag | gttaaataat | atatgaataa | aagatatatc | ttgtaagcta | attgatctcc | 960 |
| cattagcaag | cgttcagggt | ggtcctttgt | aacaggtcac | agaccaacag | taagaagttt | 1020 |
| gcttgtctgt | atcttgtttg | aagcggtttt | gattttatgt | ctcccatctg | tgtactaatt | 1080 |
| aatttatttt | tactatataa | ggtaggagat | aatgccgaac | cccatcatca | tgggccagca | 1140 |
| tagcgcaggg | tgaatggctt | caattaaaaa | aaattaaccct | tagtagagaa | aaattaaaga | 1200 |
| gaaaaacaga | atgtgtgtat | atcacttaac | catatggtta | aataataata | taatatatga | 1260 |
| ataaaagatg | catgcattca | ttagtttgtg | taaacactaa | gcagaataaa | atgtttagtt | 1320 |
| accatcttgc | atgttataat | tgtcaagtat | ctagacgatg | tgcaaaaaca | agtaatgcta | 1380 |
| ttgacatggt | tcaagaaaga | gtgagcaaag | gagtttgcat | tttgtagtat | tattaattac | 1440 |
| ttgaatagtt | ccttcatttt | tcttttaggc | cttggcttta | ttgaaacgca | tggttgggca | 1500 |
| gtcgataaca | aggatcagat | ttcacccttta | ggatttgaaa | ttatatttcc | ctgcatgatc | 1560 |
| aactatgcag | agaaacttaa | tttggatcta | cctttggatc | ctaaccttgt | aaatatgatg | 1620 |
| ctctgcgaac | gtgaattaac | aattgaaagg | tatgcttctt | tattaaatgg | tcattttaca | 1680 |
| tattatggaa | attattagtt | ttgcagccctt | gcgcaaaaac | tcctaatgta | taaaacaatt | 1740 |
| ataggggaag | ttcaacaata | ttagtcgtct | gaagctaaat | cttaataaaa | ggcctaagcg | 1800 |
| taatctcatt | cgattcatat | attaataaga | aaaggacat | atttttttata | tctatagatc | 1860 |
| aataatcaaa | catgacaaag | agaaatatca | aaaaaacttt | gttgaaattg | gaaagataaa | 1920 |
| tgactagaaa | taggaaaaac | gaatggatat | atgcatgaaa | ggaaatatca | tagagggtag | 1980 |
| gagaggtaaa | tgtactacta | gtagttaata | atctttttgga | agaagtttac | acatctactc | 2040 |
| atccgtccaa | acagtaaaaa | gctaacataa | attttgaaac | aacttataag | tgatagttat | 2100 |
| ttcctttgtt | tcaatttatg | cggcaacatt | ttgttttttgg | tccatttttat | aaaaaatagt | 2160 |
| gactttctaa | atttgagaag | attaaacttc | tcatttttat | tcttaatgag | aaattttttat | 2220 |

```
atatatcctc acaaatgtct atgattttt tatcataaat ttcaaaagta tcctttattt    2280
caaactccat agtaattcaa attttaccac ataaagtctc ccatggtggt atataataac    2340
tgtaattttt tgcctgtaat tattgagacc aaaagtacta acttcatttg tcttgccttt    2400
aatcgatcac acgaacaatt atacgacggt gtttgactag gtactgaact taaggaagat    2460
tgaatgactt ttgccacatg tctaaagtgc gctagactta cacatgacat agcatttatt    2520
tgattataaa agtatctcat taaggataaa ttaaaagttt acaaaagtt atcaaataaa    2580
gaatgggatt cttcttttgt gaaaagacat taaaaaaaac atgtcatata aatggaaca    2640
aaggaatata gaatttgccc tctccacgaa tttgtatgca gatttgtaaa ttgacttata    2700
aaactcctaa ctttatggag taagtctctt gggaaaatgt cattctgaag aatgataaag    2760
caaaaaaaaa tagtttaaaa tttgtagagt gcaaaacttc atttttaatt taaacatgac    2820
tgcaacactc accccttcca aaaatagaaa gaggtcattc ttttttttgta cagactaaaa    2880
agaaaatagg ttcacataaa ttgaaacgaa aggagtacta gattttgata ctctagcttc    2940
aactcatcaa tttgttgggc cattttttaa ccaatagagc cttaaagaat gaattcgagg    3000
ggaatatggc aaatgtagaa tattttgctg aagggctcgg tgaattatgt cattggaaag    3060
agatgatgct tcgtcagaga cacaacgggt cgctctttga ttcaccagcc actactgcag    3120
ctgccttgat ttaccatcag tacgatgaga atgctttgg gtacttgaac tcaatcttga    3180
aactgcacga taattggggt atgcactact aagatcatct caatacttcc ccattatctg    3240
cctaaaggaa atactttc atatctcttc ttagaattcg ttggaattaa gttttaatta    3300
tgttagtatg tttactatat gttcgatatg tttgatagga gactaatagt tttagggtac    3360
tagaaaatat aaagtacttc tactgataag aaatttatgt tagtatgata atttagcgct    3420
tgtgacgcat ggtgacatcc ttaccgcttc tccccacaag tacaaatgta catctacgaa    3480
caactcacat attgactcaa atcatgcttt agagaaaatc acaagaagag taagtctaat    3540
aaacttacct ctcaagtcca aactctgaca tagtactacg atgaaccaat ttatttaaaa    3600
agctcggacg tcatcaacaa agggatatct acatatatgt ggaaaatggc agaattctga    3660
ccgccaaaac agtcggaatt cacgaatttc ctactacttt ccgaccaaaa ttggtcggtc    3720
gaaaaacagt tggtcggaaa ataattttcg atcaaatccg ttagtgattt ccgaccaaag    3780
tagtcggaac gttcgaaagg ttagacgacc aaatattttc aaatttccga ccaaagtggt    3840
cggaatttac cgaccgaatc agtcgtaata atataaataa aataattatt tatttaaaat    3900
taaataatat aaatatataa tttccgaccg aatcggtcgg aaattaatat ttaaaaaata    3960
taatttccga ccgaatcggt cggaaattaa tatttaaaaa atatatttta tttaatttcc    4020
gacgaaatcc gtcgaaaact ttttaatttt tttttaaaat ttccgaccgc atcggtcgaa    4080
aatctgggaa tttttggcaa aatgtgggca gctgtccgac tgtttccgtc ggaaatcagt    4140
cggaattttc tgtaaaactg agcagcattc tgcccaattt ggagctacac cacgtgtcaa    4200
actattacaa tataataacg ccaacaacca atcaaccatt aacacaatct aaaccaacaa    4260
taccaatcat taacataatc taaactaaca ataccaacta ttaaaataat ctaaaccaac    4320
cattaacaca acctaaacta acaataccaa ccattaaacc taacaatttt ggacataaaa    4380
atatccaaat agtagcccac attcaagttt aaaaataaaa cataaagttg tctctcacaa    4440
tcaagtttac caatcaacca aaataccaca cctaaactac tacacatcag attcagtttg    4500
ttcatcctca tcatcagata gatcatgccc atgttttctc atgaatttct ggcagtggag    4560
```

```
ggtcgtcgac ggagctgcag cgaggcggca tcgccggtga gtggcattgg tgatggcagc      4620
ggcgggttgg gtgggggga gagggaggt ttgagtgtga gagagagaag agagaaggaa       4680 gaaacaggg aaagaaaaaa gaaagggtc agggggttt taaaagaaaa taggtcaaat       4740
agtcgaacct cgttttaata aaaaattccg accgaattag tcgataacag ttatgcggta      4800
tttttcgcca aaatttacga cggatataga cggaatatca gccgtaatta ttattaaaaa      4860
ttgaaaaata tattttatg caatttccga ccgatttcgt cagaaatttg cgactacttt      4920
ttccggtcgg aatatttcgg tcggaaattg gccgttttt agtagtgata tatgagttca      4980
tatatcaata acgcttcata acaataccaa ctaagtaagt agcacttagg tccaacttca      5040
catgactttc acaaaaattc ttatttcacc atttgatatc aatccttgaa ttttaactcc      5100
aattcatcta ttaaatgtgt tatggaatct agccatttca ttagaagttc aaaacgatat      5160
cgttcaaata agtccaacac tattcatctt ccctattaat aaactttcag tgtcaaagct      5220
atgataggag ggttcatcta ttccacccct ctaactactt tttcagctca taataatat       5280 taaaacactc acttatactt cataaataag gttcatgtag taaaaattat ctttgtaaga      5340
aaatcctaga aaatctctct tttggtgttt ttggttgatt taataaaatt tagcaaacta      5400
aaggaagttt caatgttaat actagaatta attaacttta tgagcacaa aacatcgata      5460 aaaacttgcc ttgtatgacc caaatgaacc cttggtcaaa atcctctcga tcctaaatca      5520
tctaactaat aatgagttgt acacctgagt atttaaagac actgtaaact aacttctaac      5580
taataactaa ctaacagcta attacaaaga tcaataacta acactaattt atgaaccttc      5640
tagaagtgta ctcctttaaa taatacactg tacaacctgt ctaagctaca tatttcagca      5700
ttactaatat aatcttttc gttattctta tagtccccac tatttgccct acaaagatac      5760
attcaaatct cttcttagtt gatgcccttc aaaatcttgg agtagatcgg tattttaaaa      5820
cagaagtcaa aagagtacta gatgaaatat acaggtaatt tgaaatgatc ttcatggttt      5880
atacaattta tcttttttaaa acttttatta atattaatgc tgaattatga ataggctttg      5940
gctagaaaag aatgaagaaa tttttcaga cgttgctcat tgtgccatgg cgtttcgact      6000
tttacggatg aataactatg aagtttcctc aggtttgtaa ctaaaaactc agaaaattaa      6060 attttacct atgcaccaat aatataaggg gtgtcttgtc gtaattggta aagttgtttg      6120
tcgtaattgg taaagttgtt ggtcacaagt tcaggccgtg caaatagcct cttgcaaaaa      6180
tgcagggtaa ggctgcttag aatatacct tatggttcga cccttcccg gacctcgcgc       6240 atagcgggag cttaatgcac cgggctgtcc ttttacttat gcaccaataa attgttactt      6300
tctttctgca gaagaacttg aaggatttgt cgaccaagaa catttcttta caacatcaag      6360
tgggaaactt atgaatcacg ttgcaattct cgaacttcac cgagcttcac aggtggctat      6420
tcatgaaagg aaagatcaca ttttagataa aataagtact tggacaagga attttatgga      6480
gcaaaaactc ttggacaagc acatccctga taggtcaaag aaggaggtat cacctgtata      6540
taaattaggc cattcaaaaa acattctttg taattttcaa ttttatgata ttccattact      6600
agcgagtcaa ttaaatatca gatggaattt gctatgagga aattttatgg cacatttgat      6660
cgagtggaaa ctagacgtta catcgagtca tacaaaatgg acagttttaa gatcttaaaa      6720
gcggcttaca ggtataattc tgacactatt actataagat tttagataat atgtaccgtc      6780
agcgggttac atttgccaat tattgcaggt aatctatatt gttttcaaga ttataaatct      6840 cacatttaa ggaggcttac ctgtaaatat tatttgagtg acggtaaaaa aaactttaca      6900
ttaatgatgt atgtaacgta aactcttact aaaagtagta tatatgtttt gtttattctt      6960
```

```
attattctct tctgcattta aacgtgtgga caggggcaga tttataggag agattatggg    7020
gcacgcaaac ccatgatctc ctcaaaatta gatattttat gtacatattt tttaaaattg    7080
gtataatatt aactattggc atccatgctt ctatttaata tattttcct cttttttattt    7140 tagtaataca ttcatgtact gaaaatccta gatccacatc tgtatatggg cggatcagag    7200
ttacggttgt agcaatgccc accgccttca acttaaacaa catatgtcag tgaacattgg    7260
tatgctaacg cttaatatgg gtagcaagaa aaaatacaag ctactttaaa taaaatgtaa    7320
tggtacattt tctatcgaag ttggaagtcc ttaaaaattg gtcatattat tatgtggggt    7380
ctctctcttt ctctctttta ggtcttccgg tattaacaac atagacttgc taaagttctc    7440
agaacacgat tttaacttgt gccaaacccg acacaaagaa gaacttcaac agatgaaaag    7500 gtatctcacac tggttagctt gactagacct tgtcattctt aaacaacttc attttgttga    7560
taattatata tatatatata tatatatata tatatatgaa tgtaggtggt tcacagattg    7620
caaactcgaa caagtaggat tatcacaaca gtacttatac actagttact tcataattgc    7680
tgccatactc tttgaacctg aatatgctga tgctcgtcta gcatatgcaa agtacgccat    7740
aataataaca gcggtggatg atttcttcga ttgttttatt tgcaaagaag aactgcaaaa    7800
catcatcgaa ttagtagaga ggtattgtta tctcttttct tataatatat caacaaaatc    7860
ctttgaccta tgttgttcaa ctcacatttt ttagaggcac ttgagtttat gataaagaat    7920
gttacacttg tccctcatca attttgtacg ggcttttaaa agggttcaaa tgatcctagg    7980
ctacttcatt catagcttta tggttttgga tttatactaa tattctttca catggtatca    8040
gagccaaaac tttctttttt tcattcagac cattaagcca ctaacattgc tatggcctaa    8100
cttatcaatt atcatgttga gcctaatcta cttaactctt gaagatcaca atttgttgag    8160
actcttctct ttctacgtta aaaataataa ccaaaacaga aacaaaccgt agaaccgggc    8220
tgtgttgcaa gagagtatta gagaatgtta cacttgtccc ttagatactc cacccgatta    8280
ccttgaaatt ttggattaga tactcatact cttttcacata ttatgttaac actttcacta    8340
tagatgggag ggatactcaa ccgtcggatt ccgttcagag agggttagaa ttttcttttt    8400
ggcactttac aaaatggtag aggaaattgc ggcaaaggcg gaaactaagc aaggtcgatg    8460
tgtcaaagat caccttatta acttggtatg aagaagtaca ttaattatta tatattctct    8520
aaatcaattt tttttcatg cttatatttc tttcttttcg attgactaga aatatatctt    8580
gttatagtgg attgatatgt tgaagtgtat gctggtggaa ttggacctt ggaaaattaa    8640 atcaactacc ccaagcatag aggagtactt gtctgttgca tgtgtaacta ttggtgttcc    8700
atgttttgtt ctcacatcac tatatcttct tggaccaaaa ctgtccaagg atgtcataga    8760
aagttctgag gtcagtgcct tatgcaattg tacagctgct gtggcccgat tgattaatga    8820
tatacacagt tacaaggtaa tattattttc ttcgttagaa gaatatttta tcaaatgttg    8880
gctattgatt tttgacaatc ttttttcaat atattgaact gagataaaat tttacataaa    8940
atattctttt ttcgaaacac taacttcttc aaatcaaatt ttattccaaa aattactaaa    9000
atttacattt gaaagtgaga agtgacacaa aaacaaagcc ttgtccggct agattgatat    9060
ttgataaatt aatataatat aatgtgctgc tggttcattt tcttcttatt aagctcgtct    9120
cactaagttt tcgcgctaga aggatcagac cacgttgaat ttattttgta cgcttttttt    9180
tcaagtagac atacagtgt ataattataa cattaatcct tattatttcg tgtgttcttg    9240
cagagagaac aagcagaaag ttcaacaaat atggtatcaa tattaataac acaaagtcag    9300
```

```
ggaactatct ctgaagaaga ggctataaga cagataaagg aaatgatgga aagtaagaga      9360
agagagttgc tagggatggt tctacaaaat aaagaaagcc aattgccaca agtgtgcaag      9420
gatctttttt ggacgacaat caacgcagct tattctatac atacacatgg cgatgggtat      9480
cgcttcccag aggaattcaa gaaccatatc aacgatgtaa tttacaaacc actcaatcaa      9540
tattccccat aa                                                          9552

<210> SEQ ID NO 49
<211> LENGTH: 494
<212> TYPE: PRT
<213> ORGANISM: Nicotiana tabacum

<400> SEQUENCE: 49

Met Ser Val Phe Ala Val Ile Ser Phe Phe Leu Leu Phe Phe Leu
1               5                   10                  15

Phe Lys Ser Tyr Leu Pro Ser Ser Lys Thr Lys Asn Ser Pro Pro
                20                  25                  30

Ser Pro Ser Lys Leu Pro Leu Ile Gly His Phe His Lys Leu Gly Leu
                35                  40                  45

Gln Pro His Arg Ser Leu Gln Lys Leu Ser Asn Glu His Gly Pro Met
50                  55                  60

Met Met Leu Gln Phe Gly Ser Val Pro Val Leu Ile Ala Ser Ser Ala
65                  70                  75                  80

Glu Ala Ala Ser Glu Ile Met Lys Thr Gln Asp Leu Ser Phe Ala Asn
                85                  90                  95

Lys Pro Ile Ser Thr Ile Pro Ser Lys Leu Phe Phe Gly Pro Lys Asp
                100                 105                 110

Val Ala Phe Thr Pro Tyr Gly Asp Tyr Trp Arg Asn Ala Arg Ser Ile
                115                 120                 125

Cys Met Leu Gln Leu Leu Asn Asn Lys Arg Val Gln Ser Phe Arg Lys
                130                 135                 140

Ile Arg Glu Glu Glu Thr Ser Leu Leu Leu Gln Arg Ile Arg Glu Ser
145                 150                 155                 160

Pro Asn Ser Glu Val Asp Leu Thr Glu Leu Phe Val Ser Met Thr Asn
                165                 170                 175

Asp Ile Val Cys Arg Val Ala Leu Gly Arg Lys Tyr Cys Asp Gly Glu
                180                 185                 190

Glu Gly Arg Lys Phe Lys Ser Leu Leu Leu Glu Phe Val Glu Leu Leu
                195                 200                 205

Gly Val Phe Asn Ile Gly Asp Tyr Met Pro Trp Leu Ala Trp Met Asn
                210                 215                 220

Arg Phe Asn Gly Leu Asn Ala Lys Val Asp Lys Val Ala Lys Glu Phe
225                 230                 235                 240

Asp Ala Phe Leu Glu Asp Val Ile Glu Glu His Gly Gly Asn Lys Lys
                245                 250                 255

Ser Asp Thr Glu Ala Glu Gly Ala Asp Phe Val Asp Ile Leu Leu Gln
                260                 265                 270

Val His Lys Glu Asn Lys Ala Gly Phe Gln Val Glu Met Asp Ala Ile
                275                 280                 285

Lys Ala Ile Ile Met Asp Met Phe Ala Ala Gly Thr Asp Thr Thr Ser
                290                 295                 300

Thr Leu Leu Glu Trp Thr Met Asn Glu Leu Leu Arg Asn Pro Lys Thr
305                 310                 315                 320

Leu Asn Lys Leu Arg Asp Glu Val Arg Gln Val Thr Gln Gly Lys Thr
```

```
                    325                 330                 335
Glu Val Thr Glu Asp Asp Leu Glu Lys Met Pro Tyr Leu Arg Ala Ala
                340                 345                 350

Val Lys Glu Ser Ser Arg Leu His Ser Pro Val Pro Leu Leu Pro Arg
                355                 360                 365

Glu Ala Ile Lys Asp Ala Lys Val Leu Gly Tyr Asp Ile Ala Ala Gly
370                 375                 380

Thr Gln Val Leu Val Cys Pro Trp Ala Ile Ser Arg Asp Pro Asn Leu
385                 390                 395                 400

Trp Glu Asn Pro Glu Glu Phe Gln Pro Glu Arg Phe Leu Asp Thr Ser
                405                 410                 415

Ile Asp Tyr Lys Gly Leu His Phe Glu Leu Ile Pro Phe Gly Ala Gly
                420                 425                 430

Arg Arg Gly Cys Pro Gly Ile Thr Phe Ala Lys Phe Val Asn Glu Leu
                435                 440                 445

Ala Leu Ala Arg Leu Met Phe His Phe Asp Phe Ser Leu Pro Lys Gly
                450                 455                 460

Val Lys His Glu Asp Leu Asp Val Glu Glu Ala Ala Gly Ile Thr Val
465                 470                 475                 480

Arg Arg Lys Phe Pro Leu Leu Ala Val Ala Thr Pro Cys Ser
                485                 490

<210> SEQ ID NO 50
<211> LENGTH: 321
<212> TYPE: PRT
<213> ORGANISM: Nicotiana tabacum

<400> SEQUENCE: 50

Met Ala Glu Lys Ile Thr Ser His Glu Asn Thr Arg Tyr Ala Val Val
1               5                   10                  15

Thr Gly Gly Asn Lys Gly Ile Gly Tyr Glu Thr Cys Arg Gln Leu Ala
                20                  25                  30

Lys Glu Gly Ile Val Val Leu Thr Ala Arg Asp Glu Arg Arg Gly
            35                  40                  45

Ile Glu Ala Leu Glu Lys Leu Lys Glu Glu Tyr Ser Ser Asn Lys Thr
50                  55                  60

Asp Asp Asp Gln Ile Leu Phe His Gln Leu Asp Val Met Asp Pro Ala
65                  70                  75                  80

Ser Ile Ser Ser Leu Val Asp Phe Ile Lys Thr Lys Phe Gly Lys Leu
                85                  90                  95

Asp Ile Leu Val Asn Asn Ala Gly Ile Gly Gly Leu Met Val Glu Gly
                100                 105                 110

Asp Val Val Ile Ile Lys Asp Leu Ile Glu Gly Asp Phe Val Thr Ile
                115                 120                 125

Ser Ala Glu Asn Gly Glu Glu Asp Gly Ile Lys Lys Ser Ile Glu Gly
130                 135                 140

Ile Glu Arg Ile Val Thr Asp Tyr Glu Leu Thr Lys Gln Cys Leu Glu
145                 150                 155                 160

Thr Asn Phe Tyr Gly Ala Lys Arg Met Ile Glu Ala Phe Ile Pro Leu
                165                 170                 175

Leu Gln Leu Ser Asn Ser Pro Arg Ile Val Asn Val Ala Ser Phe Leu
                180                 185                 190

Gly Lys Leu Lys Leu Leu Cys Asn Gln Trp Ala Ile Gly Met Leu Ser
                195                 200                 205
```

```
Asp Ala Lys Ser Leu Arg Glu Glu Arg Val Asp Glu Val Leu Asn Glu
    210                 215                 220

Phe Ile Lys Asp Phe Lys Glu Lys Ser Ile Glu Ala Lys Gly Trp Pro
225                 230                 235                 240

Thr Tyr Phe Ser Ala Tyr Lys Val Ser Lys Ala Ser Leu Ile Ala Tyr
                245                 250                 255

Thr Arg Val Leu Ala Thr Lys Tyr Pro Asn Phe Arg Ile Asn Ser Val
                260                 265                 270

Cys Pro Gly Phe Cys Lys Thr Asp Val Asn Cys Asn Thr Gly Ser Leu
                275                 280                 285

Thr Ala Glu Glu Gly Ala Glu Ser Leu Val Lys Leu Ala Leu Val Pro
                290                 295                 300

Asn Asp Gly Pro Ser Gly Leu Phe Phe Tyr Arg Lys Glu Val Thr Ser
305                 310                 315                 320

Phe

<210> SEQ ID NO 51
<211> LENGTH: 598
<212> TYPE: PRT
<213> ORGANISM: Nicotiana sylvestris

<400> SEQUENCE: 51

Met Ser Gln Ser Ile Ser Pro Leu Ile Cys Ser His Phe Ala Lys Phe
1               5                   10                  15

Gln Ser Asn Ile Trp Arg Cys Asn Thr Ser Gln Leu Arg Val Ile His
                20                  25                  30

Ser Ser Tyr Ala Ser Phe Gly Gly Arg Lys Glu Arg Val Arg Arg
            35                  40                  45

Met Asn Arg Ala Met Asp Leu Ser Ser Ser Arg His Leu Ala Asp
    50                  55                  60

Phe Pro Ser Thr Ile Trp Gly Asp His Phe Leu Ser Tyr Asn Ser Glu
65                  70                  75                  80

Ile Thr Glu Ile Thr Thr Gln Glu Lys Asn Glu His Glu Met Leu Lys
                85                  90                  95

Glu Ile Val Arg Lys Met Leu Val Glu Thr Pro Asp Asn Ser Thr Gln
                100                 105                 110

Lys Leu Val Leu Ile Asp Thr Ile Gln Arg Leu Gly Leu Ala Tyr His
            115                 120                 125

Phe Asn Asp Glu Ile Glu Asn Ser Ile Gln Asn Ile Phe Asn Leu Ser
    130                 135                 140

Gln Asn Ser Glu Asp Asp Glu His Asn Leu Tyr Val Ala Ala Leu
145                 150                 155                 160

Arg Phe Arg Leu Ala Arg Gln Gln Gly Tyr Tyr Met Ser Ser Asp Val
                165                 170                 175

Phe Lys Gln Phe Thr Asn His Asp Gly Lys Phe Lys Glu Asn His Thr
            180                 185                 190

Asn Asp Val Gln Gly Leu Leu Ser Leu Tyr Glu Ala Ala His Met Arg
    195                 200                 205

Val His Asp Glu Glu Ile Leu Glu Glu Ala Leu Ile Phe Thr Thr Thr
210                 215                 220

His Leu Glu Ser Val Ile Pro Asn Leu Ser Asn Ser Leu Lys Val Gln
225                 230                 235                 240

Val Thr Glu Ala Leu Ser His Pro Ile Arg Lys Ala Ile Pro Arg Val
                245                 250                 255
```

Gly Ala Arg Lys Tyr Ile His Ile Tyr Glu Asn Ile Gly Thr His Asn
             260                 265                 270

Asp Leu Leu Leu Lys Phe Ala Lys Leu Asp Phe Asn Met Leu Gln Lys
             275                 280                 285

Leu His Arg Lys Glu Leu Asn Glu Leu Thr Ser Trp Trp Lys Asp Leu
             290                 295                 300

Asp Arg Ala Asn Lys Phe Pro Tyr Ala Lys Asp Arg Leu Val Glu Ala
305                 310                 315                 320

Tyr Phe Trp Thr Val Gly Ile Tyr Phe Glu Pro Gln Tyr Ser Arg Ser
                 325                 330                 335

Arg Ser Leu Val Thr Lys Val Lys Met Asn Ser Ile Ile Asp Asp
             340                 345                 350

Thr Tyr Asp Ala Tyr Ala Thr Phe Asp Glu Leu Val Leu Phe Thr Asp
             355                 360                 365

Ala Ile Gln Arg Trp Asp Glu Gly Ala Met Asp Leu Leu Pro Thr Tyr
             370                 375                 380

Leu Arg Pro Ile Tyr Gln Gly Leu Leu Asp Val Phe Asn Glu Met Glu
385                 390                 395                 400

Glu Val Leu Ala Lys Glu Gly Lys Ala Asp His Ile Tyr Tyr Ala Lys
                 405                 410                 415

Lys Glu Met Lys Lys Val Ala Glu Val Tyr Phe Lys Glu Ala Glu Trp
             420                 425                 430

Leu Asn Ala Asn Tyr Ile Pro Lys Cys Glu Glu Tyr Met Lys Asn Gly
             435                 440                 445

Leu Val Ser Ser Thr Gly Pro Met Tyr Gly Ile Ile Ser Leu Val Val
             450                 455                 460

Met Glu Glu Ile Ile Thr Lys Glu Ala Phe Glu Trp Leu Thr Asn Glu
465                 470                 475                 480

Pro Leu Ile Leu Arg Ala Ala Ser Thr Ile Cys Arg Leu Met Asp Asp
                 485                 490                 495

Met Ala Asp His Glu Val Glu Gln Gln Arg Gly His Val Ala Ser Phe
             500                 505                 510

Val Glu Cys Tyr Met Lys Glu Tyr Gly Val Ser Lys Gln Glu Ala Tyr
             515                 520                 525

Val Glu Met Arg Lys Lys Ile Thr Asn Ala Trp Lys Asp Ile Asn Lys
             530                 535                 540

Glu Leu Leu Arg Pro Thr Ala Val Pro Met Phe Ile Leu Glu Arg Ser
545                 550                 555                 560

Leu Asn Phe Ser Arg Leu Ala Asp Thr Phe Leu Lys Asp Asp Gly
                 565                 570                 575

Tyr Thr Asn Pro Lys Ser Lys Val Lys Asp Leu Ile Ala Ser Leu Phe
             580                 585                 590

Val Glu Ser Val Asp Ile
             595

<210> SEQ ID NO 52
<211> LENGTH: 792
<212> TYPE: PRT
<213> ORGANISM: Nicotiana tabacum

<400> SEQUENCE: 52

Met Val Leu Gly Leu Arg Ser Lys Ile Pro Leu Pro Asp His Lys
1               5                   10                  15

Leu Gly Asn Ile Lys Leu Gly Ser Val Thr Asn Ala Ile Cys His Arg
             20                  25                  30

```
Pro Cys Arg Val Arg Cys Ser His Ser Thr Ala Ser Ser Met Glu Glu
        35                  40                  45

Ala Lys Glu Arg Ile Arg Glu Thr Phe Gly Lys Ile Glu Leu Ser Pro
 50                  55                  60

Ser Ser Tyr Asp Thr Ala Trp Val Ala Met Val Pro Ser Arg Tyr Ser
 65                  70                  75                  80

Met Asn Gln Pro Cys Phe Pro Gln Cys Leu Asp Trp Ile Leu Glu Asn
                 85                  90                  95

Gln Arg Glu Asp Gly Ser Trp Gly Leu Asn Pro Ser His Pro Leu Leu
                100                 105                 110

Val Lys Asp Ser Leu Ser Ser Thr Leu Ala Ser Leu Leu Ala Leu Arg
            115                 120                 125

Lys Trp Arg Ile Gly Asp Asn Gln Val Gln Arg Gly Leu Gly Phe Ile
        130                 135                 140

Glu Thr His Gly Trp Ala Val Asp Asn Lys Asp Gln Ile Ser Pro Leu
145                 150                 155                 160

Gly Phe Glu Ile Ile Phe Pro Cys Met Ile Asn Tyr Ala Glu Lys Leu
                165                 170                 175

Asn Leu Asp Leu Pro Leu Asp Pro Asn Leu Val Asn Met Met Leu Cys
                180                 185                 190

Glu Arg Glu Leu Thr Ile Glu Arg Ala Leu Lys Asn Glu Phe Glu Gly
            195                 200                 205

Asn Met Ala Asn Val Glu Tyr Phe Ala Glu Gly Leu Gly Glu Leu Cys
        210                 215                 220

His Trp Lys Glu Met Met Leu Arg Gln Arg His Asn Gly Ser Leu Phe
225                 230                 235                 240

Asp Ser Pro Ala Thr Thr Ala Ala Leu Ile Tyr His Gln Tyr Asp
                245                 250                 255

Glu Lys Cys Phe Gly Tyr Leu Asn Ser Ile Leu Lys Leu His Asp Asn
                260                 265                 270

Trp Val Pro Thr Ile Cys Pro Thr Lys Ile His Ser Asn Leu Phe Leu
            275                 280                 285

Val Asp Ala Leu Gln Asn Leu Gly Val Asp Arg Tyr Phe Lys Thr Glu
        290                 295                 300

Val Lys Arg Val Leu Asp Glu Ile Tyr Arg Leu Trp Leu Glu Lys Asn
305                 310                 315                 320

Glu Glu Ile Phe Ser Asp Val Ala His Cys Ala Met Ala Phe Arg Leu
                325                 330                 335

Leu Arg Met Asn Asn Tyr Glu Val Ser Ser Glu Glu Leu Glu Gly Phe
            340                 345                 350

Val Asp Gln Glu His Phe Phe Thr Thr Ser Ser Gly Lys Leu Met Asn
        355                 360                 365

His Val Ala Ile Leu Glu Leu His Arg Ala Ser Gln Val Ala Ile His
    370                 375                 380

Glu Arg Lys Asp His Ile Leu Asp Lys Ile Ser Thr Trp Thr Arg Asn
385                 390                 395                 400

Phe Met Glu Gln Lys Leu Leu Asp Lys His Ile Pro Asp Arg Ser Lys
                405                 410                 415

Lys Glu Met Glu Phe Ala Met Arg Lys Phe Tyr Gly Thr Phe Asp Arg
                420                 425                 430

Val Glu Thr Arg Arg Tyr Ile Glu Ser Tyr Lys Met Asp Ser Phe Lys
            435                 440                 445
```

```
Ile Leu Lys Ala Ala Tyr Arg Ser Ser Gly Ile Asn Asn Ile Asp Leu
450                 455                 460

Leu Lys Phe Ser Glu His Asp Phe Asn Leu Cys Gln Thr Arg His Lys
465                 470                 475                 480

Glu Glu Leu Gln Gln Met Lys Arg Trp Phe Thr Asp Cys Lys Leu Glu
                485                 490                 495

Gln Val Gly Leu Ser Gln Gln Tyr Leu Tyr Thr Ser Tyr Phe Ile Ile
            500                 505                 510

Ala Ala Ile Leu Phe Glu Pro Glu Tyr Ala Asp Ala Arg Leu Ala Tyr
                515                 520                 525

Ala Lys Tyr Ala Ile Ile Thr Ala Val Asp Asp Phe Phe Asp Cys
530                 535                 540

Phe Ile Cys Lys Glu Glu Leu Gln Asn Ile Ile Glu Leu Val Glu Arg
545                 550                 555                 560

Trp Glu Gly Tyr Ser Thr Val Gly Phe Arg Ser Glu Arg Val Arg Ile
                565                 570                 575

Phe Phe Leu Ala Leu Tyr Lys Met Val Glu Glu Ile Ala Ala Lys Ala
                580                 585                 590

Glu Thr Lys Gln Gly Arg Cys Val Lys Asp His Leu Ile Asn Leu Trp
            595                 600                 605

Ile Asp Met Leu Lys Cys Met Leu Val Glu Leu Asp Leu Trp Lys Ile
            610                 615                 620

Lys Ser Thr Thr Pro Ser Ile Glu Glu Tyr Leu Ser Val Ala Cys Val
625                 630                 635                 640

Thr Ile Gly Val Pro Cys Phe Val Leu Thr Ser Leu Tyr Leu Leu Gly
                645                 650                 655

Pro Lys Leu Ser Lys Asp Val Ile Glu Ser Ser Glu Val Ser Ala Leu
                660                 665                 670

Cys Asn Cys Thr Ala Ala Val Ala Arg Leu Ile Asn Asp Ile His Ser
            675                 680                 685

Tyr Lys Arg Glu Gln Ala Glu Ser Ser Thr Asn Met Val Ser Ile Leu
            690                 695                 700

Ile Thr Gln Ser Gln Gly Thr Ile Ser Glu Glu Glu Ala Ile Arg Gln
705                 710                 715                 720

Ile Lys Glu Met Met Glu Ser Lys Arg Arg Glu Leu Leu Gly Met Val
                725                 730                 735

Leu Gln Asn Lys Glu Ser Gln Leu Pro Gln Val Cys Lys Asp Leu Phe
                740                 745                 750

Trp Thr Thr Ile Asn Ala Ala Tyr Ser Ile His Thr His Gly Asp Gly
            755                 760                 765

Tyr Arg Phe Pro Glu Glu Phe Lys Asn His Ile Asn Asp Val Ile Tyr
770                 775                 780

Lys Pro Leu Asn Gln Tyr Ser Pro
785                 790

<210> SEQ ID NO 53
<211> LENGTH: 365
<212> TYPE: PRT
<213> ORGANISM: Nicotiana sp.

<400> SEQUENCE: 53

Met Ala Phe Leu Ala Thr Ile Ser Gly His Glu Asn Met Leu Leu Ser
1               5                   10                  15

Asn Thr Leu Asn Asn Asn Phe Ile Phe Ser Gly Lys Pro Pro Gln Arg
                20                  25                  30
```

```
His Ser Tyr Ser Phe Leu Pro Lys Lys Ile Gln Ala Arg Ser Val Ala
             35                  40                  45

Asn Ser Ser Lys Thr Phe Gln Val Lys Glu Glu Phe Ser Ser Lys
 50                  55                  60

Thr Glu Lys Phe Ile Leu Pro Lys Phe Asp Phe Glu Glu Tyr Met Lys
 65                  70                  75                  80

Met Lys Ala Ile Lys Val Asn Lys Ala Leu Asp Asp Ala Ile Pro Met
                 85                  90                  95

Gln Glu Pro Ile Lys Ile His Glu Ala Met Arg Tyr Ser Leu Leu Ala
                100                 105                 110

Gly Gly Lys Arg Val Arg Pro Ile Leu Cys Met Ala Ser Cys Glu Val
                115                 120                 125

Val Gly Gly Asp Glu Ser Leu Ala Ile Pro Ala Ala Cys Ser Val Glu
                130                 135                 140

Met Ile His Thr Met Ser Leu Ile His Asp Asp Leu Pro Cys Met Asp
145                 150                 155                 160

Asn Asp Asp Leu Arg Arg Gly Lys Pro Thr Ser His Lys Ala Phe Gly
                165                 170                 175

Glu Asp Thr Ala Val Leu Thr Gly Asp Ala Leu Leu Ser Leu Ala Phe
                180                 185                 190

Glu His Val Ala Ser Lys Thr Lys Asp Val Thr Pro Gln Arg Val Val
                195                 200                 205

Gln Ala Val Gly Glu Leu Gly Ser Ala Val Gly Ser Lys Gly Leu Val
                210                 215                 220

Ala Gly Gln Ile Val Asp Ile Ala Ser Glu Gly Lys Gln Val Ser Leu
225                 230                 235                 240

Thr Glu Leu Glu Tyr Ile His Asn His Lys Thr Gly Lys Leu Leu Glu
                245                 250                 255

Ala Ala Val Val Cys Gly Ala Ile Ile Gly Gly Gly Asn Glu Ile Glu
                260                 265                 270

Val Glu Arg Met Arg Asn Tyr Ala Arg Cys Leu Gly Leu Leu Phe Gln
                275                 280                 285

Val Val Asp Asp Ile Leu Asp Val Thr Lys Ser Ser Glu Glu Leu Gly
                290                 295                 300

Lys Thr Ala Gly Lys Asp Leu Val Thr Asp Lys Ala Thr Tyr Pro Lys
305                 310                 315                 320

Leu Met Gly Leu Glu Lys Ala Arg Glu Leu Ala Gly Glu Leu Val Ala
                325                 330                 335

Lys Ala Met Asp Glu Leu Ser Tyr Phe Asp Ala Ala Lys Ala Ala Pro
                340                 345                 350

Leu Tyr His Phe Ala Asn Tyr Ile Ala His Arg Gln Asn
                355                 360                 365

<210> SEQ ID NO 54
<211> LENGTH: 354
<212> TYPE: DNA
<213> ORGANISM: Nicotiana tabacum

<400> SEQUENCE: 54
atggctaggc tattctatac tatgatcatt ctcttgcttg ctttagcaac atcagcaatt    60
gctgaacctt cttgtaaaac tgttgcaaaa gggatagtac cttgtgtgtc ttatattaga   120
gggaaacatc ataatcgga caagccatca aatatgtgct gcaaaggact gaatgacata   180
gccaatgtga taaaaaatgg caaggatcgt gtagctgttt gcaagtgtat aaagatggca   240
```

```
ctttcacgta ttcattatga tcccactcgt atcacacttg cttcacaaca gtgtcatacg        300
ccttcatctc tgccttccgt tggccaaaac actaattgtg caagggcgat ctga              354
```

<210> SEQ ID NO 55
<211> LENGTH: 351
<212> TYPE: DNA
<213> ORGANISM: Nicotiana tabacum

<400> SEQUENCE: 55

```
atggcaagag agaaatctgt aatgtgtatg gtgatggttt tgggggttgc cttaattatt         60
cagggcactg gtgctgctga agaatgtagc acagtgacag cactggtagc agcatgctcc        120
agctttgtga actatggcac accagatccg actccaggtg cgccatgctg cgttgctatg        180
acgaccctaa gcaacatagc tagctccacc gaaatgcgcc aggccgtctg tagatgtgtt        240
atggacctta ttactactta caacccaaat gctactgcca ttgccacttt gcctggtttc        300
tgtggtgttt ctcttggttt caccattgac cctaacactg actgtgaata g                351
```

<210> SEQ ID NO 56
<211> LENGTH: 462
<212> TYPE: DNA
<213> ORGANISM: Nicotiana tabacum

<400> SEQUENCE: 56

```
atggcaagag agaaatctgt aatgtgtatg gtgatggttt tgggggttgc cataataatt         60
cagggcactg gagctgctga agaatgtagc acagtgacag cactggtagc agcatgctcc        120
agctttgtga actatggcac accagatcca actccaggtg caccatgctg cgtcgctatg        180
acgaccctaa gcaacatagc tagctccacc gagatgcgcc aggccgtctg tagatgcgtg        240
atggacctta ttactactta caacccaaat gctactgcca ttgccactct gcctggtttc        300
tgtggtgttt ctcttggttt caccattgac cctaacactg actccatccg atattcaagg        360
tccactggtc ctattaatcg tgatttgctc tggttaaaga agttctctac tcccgggtgt        420
ctcataacaa tatggtctct ggaaagtgat gctgaagaat ga                           462
```

<210> SEQ ID NO 57
<211> LENGTH: 480
<212> TYPE: DNA
<213> ORGANISM: Nicotiana tabacum

<400> SEQUENCE: 57

```
atgaagatgt tagctagtgc aagttcaatt tttgtagcta ttgtccttct ttcattacat         60
gttagtgctc agtcggattg ccaacaagtg atcgttggtt tagccccgtg tctgcaatac        120
attcaaggaa atgcgacaac cccatcatca ggatgttgca ctcaacttgc tactatagtg        180
aaaaatcagc cacaatgctt atgtcaagtt gttaatggtg gtggttcaaa tttaggaatt        240
aatgttaatc aaacacagac tatggctctt cccaaagctt gtaatgtcca aacaccctct        300
attagccttt gcaaaggtac tactccttca ggttcaccgg ggtctccatc cactccttca        360
ggtggatcga agggtgagcc aagtggaaat tcatcaggaa actcagtcaa gatgccatac        420
tctctcttat ttacccttgt agctatcgcg tttttcgcca cagtcttcac caccatctga        480
```

<210> SEQ ID NO 58
<211> LENGTH: 495
<212> TYPE: DNA
<213> ORGANISM: Nicotiana tabacum

<400> SEQUENCE: 58

| | | |
|---|---|---|
| atgcagatat cagcgagcac aataagtgca ataatagttg tggcagtggc tcttctttca | 60 |
| ttacatgtca tcagcgctca atcggattgc gaacaggtgg ttgttgggtt agctccgtgc | 120 |
| ctgcaataca tagaagggaa tgccacgagc ccgtcatcag gatgctgcac tcagctcgcc | 180 |
| actatagtga agacgcagcc tcagtgcttg tgtcacgttt gaatggcga gggctcatcc | 240 |
| tttggagtta atatcaatca gacacttgct ttggctcttc ctacagcttg taatgcccac | 300 |
| actccctttc ttactctatg taaagcaact tccccaactg gttctccgga aatctctccg | 360 |
| tccattcctt caggagacag atattcaaga ttttcgccaa atggagattc attgaagctg | 420 |
| cagccatact ctctgttatt taccttaat gtagccactt tgtcatatgt cacaatattc | 480 |
| agctccatct tataa | 495 |

<210> SEQ ID NO 59
<211> LENGTH: 336
<212> TYPE: DNA
<213> ORGANISM: Nicotiana tabacum

<400> SEQUENCE: 59

| | | |
|---|---|---|
| atggcaaaaa tccttatagc tttgtttgct ttgtctctaa ttttaggcca aacaaatgca | 60 |
| gatattcagt gtagtgatgt tatatcaaaa gtgagctctt gtgaagggta tttgctaggt | 120 |
| aaagttgcag cacctagccc aaattgttgc tttggattgc aagatttggc taaagtggct | 180 |
| gatgactcac aaccagatcg tcaaactatt tgtcaatgct taaagctgc catgcaaact | 240 |
| ttccctgtgg acttccaaaa agctaaacaa cttcctcaga tttgccattt caagagtact | 300 |
| ataccaattg aacccaatgt tgattgctca aagtaa | 336 |

<210> SEQ ID NO 60
<211> LENGTH: 354
<212> TYPE: DNA
<213> ORGANISM: Nicotiana tabacum

<400> SEQUENCE: 60

| | | |
|---|---|---|
| atggctaaag tagcattgtt ggtggtggtg tgcatggcag cagtagctgt gatgctaacg | 60 |
| ccccatgcag acgctgacat ctcttgtggg caggttgttg cgagcttgtc accatgcatt | 120 |
| agctatgtga ggcaaggtgg tgctattcca gcaccatgct gcagtggaat taattccctc | 180 |
| aacaaccaag ctaccagcac tcctgatcga cagacggctt gtaactgtat aaatctgct | 240 |
| gctgcaggca tcagtggcat caacttcagt cttgctggta gtcttcctag caaatgtggt | 300 |
| gtcaatcttc cctataagat tagcccttcc attgactgct ccacggtgca gtaa | 354 |

<210> SEQ ID NO 61
<211> LENGTH: 345
<212> TYPE: DNA
<213> ORGANISM: Nicotiana tabacum

<400> SEQUENCE: 61

| | | |
|---|---|---|
| atggaaatgg taggtaagat tgcatgcttt gtggttttgt gcatggtggt ggttgcaccc | 60 |
| catgcagagg cactgagctg cggccaagtt cagtccggct tggctccttg tctcccttat | 120 |
| ttgcagggcc gcggccctt ggggagctgt tgtggtggtg ttaaaggtct gttgggtgca | 180 |
| gccaagtccc catctgaccg gaagactgca tgcacttgcc tgaaatcggc tgctaatgct | 240 |
| attaagggta ttgatatggg caagccgct ggtctccctg gtgcttgtgg tgtcaacatt | 300 |
| ccttacaaga tcagcccctc cacagactgc tctaaggtcc agtaa | 345 |

<210> SEQ ID NO 62
<211> LENGTH: 294
<212> TYPE: DNA
<213> ORGANISM: Nicotiana tabacum

<400> SEQUENCE: 62

| | |
|---|---|
| atgaagaagg gtggtaattc ttttgcggca ataatcttgg ttgtgacact agtccttttt | 60 |
| cttggcgaat ttctagtgac agaggcagta acgtgcagtg tcgtggagct gagtccgtgt | 120 |
| gccggggcga tctcgtcgcc acagccaccc tcttcggcat gttgcgctaa gttgaaagag | 180 |
| cagaagcctt gtctttgtgg gtacctcaaa aatccaaacc taaggcctta tgtcaattct | 240 |
| cctaatgcca agagagttgc taaatcctgt ggagtaccca ctcccagctg ttag | 294 |

<210> SEQ ID NO 63
<211> LENGTH: 354
<212> TYPE: DNA
<213> ORGANISM: Nicotiana tabacum

<400> SEQUENCE: 63

| | |
|---|---|
| atggctaggc tattctatac tatgatcatt ctcttgcttg ctttagcaac atcagcaatt | 60 |
| gctgaacctt cttgtaaaac tgttgcaaaa gggatagtac cttgtgtgtc ttatattaga | 120 |
| gggaaacatc ataaatcgga caagccatca aatatgtgct gcaaaggact gaatgacata | 180 |
| gccaatgtga taaaaaatgg caaggatcgt gtagctgttt gcaagtgtat aaagatggca | 240 |
| ctttcacgta ttcattatga tcccactcgt atcacacttg cttcacaaca gtgtcatacg | 300 |
| ccttcatctc tgccttccgt tggccaaaac actaattgtg caagggcgat ctga | 354 |

<210> SEQ ID NO 64
<211> LENGTH: 351
<212> TYPE: DNA
<213> ORGANISM: Nicotiana tabacum

<400> SEQUENCE: 64

| | |
|---|---|
| atggcaagag agaaatctgt aatgtgtatg gtgatggttt tgggggttgc cttaattatt | 60 |
| cagggcactg gtgctgctga agaatgtagc acagtgacag cactggtagc agcatgctcc | 120 |
| agctttgtga actatggcac accagatccg actccaggtg cgccatgctg cgttgctatg | 180 |
| acgaccctaa gcaacatagc tagctccacc gaaatgcgcc aggccgtctg tagatgtgtt | 240 |
| atggacctta ttactactta caacccaaat gctactgcca ttgccacttt gcctggtttc | 300 |
| tgtggtgttt ctcttggttt caccattgac cctaacactg actgtgaata g | 351 |

<210> SEQ ID NO 65
<211> LENGTH: 655
<212> TYPE: DNA
<213> ORGANISM: Nicotiana tabacum

<400> SEQUENCE: 65

| | |
|---|---|
| atggcaagag agaaatctgt aatgtgtatg gtgatggttt tgggggttgc cataataatt | 60 |
| cagggcactg gagctgctga agaatgtagc acagtgacag cactggtagc agcatgctcc | 120 |
| agctttgtga actatggcac accagatcca actccaggtg caccatgctg cgtcgctatg | 180 |
| acgaccctaa gcaacatagc tagctccacc gagatgcgcc aggccgtctg tagatgcgtg | 240 |
| atggacctta ttactactta caacccaaat gctactgcca ttgccactct gcctggtttc | 300 |
| tgtggtgttt ctcttggttt caccattgac cctaacactg actgtgaata gtaagtaaga | 360 |

| | |
|---|---|
| caaccataag tttcttatca cctaatattt catactttgt tgttggttt agccatccga | 420 |
| tattcaaggt ccactggtcc tattaatcgt gatttgctct ggttaaagaa gttctctact | 480 |
| cccggggtga aacccgaaa actttgtctt aagaggtgga ggtattctaa ccatccacca | 540 |
| cacaccttgg tggttaatat ttcatagttt tatcacaatg tctgatcaat cttttctttt | 600 |
| ctctttgcag tgtctcataa caatatggtc tctggaaagt gatgctgaag aatga | 655 |

<210> SEQ ID NO 66
<211> LENGTH: 1174
<212> TYPE: DNA
<213> ORGANISM: Nicotiana tabacum

<400> SEQUENCE: 66

| | |
|---|---|
| atgaagatgt tagctagtgc aagttcaatt tttgtagcta ttgtccttct ttcattacat | 60 |
| gttagtgctc agtcggattg ccaacaagtg atcgttggtt tagccccgtg tctgcaatac | 120 |
| attcaaggaa atgcgacaac cccatcatca ggatgttgca ctcaacttgc tactatagtg | 180 |
| aaaaatcagc acaatgctt atgtcaagtt gttaatggtg tggttcaaa tttaggaatt | 240 |
| aatgttaatc aaacacagac tatggctctt cccaaagctt gtaatgtcca aacaccctct | 300 |
| attagccttt gcaaaggtat gttatgttta tcaataatat tctgctttct ttttctcttt | 360 |
| tcttttcact ttttcacttt tgttcaaact tgatgtatat tttgtataat gacattttct | 420 |
| agataaatat ttttttaaa gaagtcattt tttaagaaat acatttccaa tcaaagtga | 480 |
| agaatgactt cccttggacg aaatttgttt tccttacaac aatattaagt tgtaacttta | 540 |
| tattaattat tacttgtttt atttagagat tattattaat atttaatgct taaattttta | 600 |
| tcagatttaa tattattatt attattcatt ttctactgga tattttttgt ccaaaaaata | 660 |
| tcacttttca aaaaaatata tttcatggaa atgacttct gatatgttaa acacactcga | 720 |
| gtgaagattt tcaagtttat aacaagtttt aatttgtctt atattatcaa tataaacatt | 780 |
| tcaggtacta ctccttcagg ttcaccgggg tctccatcca ctccttcagg tacgataat | 840 |
| acgagcaaaa cttcttttc tagtaatata tacgaacaaa actcatcttt gtctaaacca | 900 |
| tacttagccc accttattac accgcgtggc ttcaagtagt tcccctacta gtaacacgcg | 960 |
| tatcaaaccc accttatctc actgcatgtg tatcaaccct ttggatgtta ttttttcttc | 1020 |
| ctattaacaa aattaatctt gtatacttt ggcaggtgga tcgaagggtg agccaagtgg | 1080 |
| aaattcatca ggaaactcag tcaagatgcc atactctctc ttatttaccc ttgtagctat | 1140 |
| cgcgttttc gccacagtct tcaccaccat ctga | 1174 |

<210> SEQ ID NO 67
<211> LENGTH: 1817
<212> TYPE: DNA
<213> ORGANISM: Nicotiana tabacum

<400> SEQUENCE: 67

| | |
|---|---|
| atgcagatat cagcgagcac aataagtgca ataatagttg tggcagtggc tcttctttca | 60 |
| ttacatgtca tcagcgctca atcggattgc gaacaggtgg ttgttgggtt agctccgtgc | 120 |
| ctgcaataca tagaagggaa tgccacgagc ccgtcatcag gatgctgcac tcagctcgcc | 180 |
| actatagtga agacgcagcc tcagtgcttg tgtcacgttt tgaatggcga gggctcatcc | 240 |
| tttggagtta atatcaatca gacacttgct ttggctcttc ctacagcttg taatgcccac | 300 |
| actccctttc ttactctatg taaggtacg ctaaagttat cactacttct ttaattccca | 360 |
| aacactagtc gtttgactaa ctaaattttc ttaatatatt tgtctttaaa aaaaacttga | 420 |

```
agtatttatt actttctctg tctcaattta tgtaaagttg attatacgga gggtaagaaa      480
gaaatataaa cctttgaaat ttgtattcta aaacacgctt tagatattta tatgtctata      540
aattatttta ttaaggataa aatggatatt ttgaagtcaa ttaaattact tccaaaacta      600
gaaaggtaat attcttttta ggacaaacta aaaagttttt ccaaacacat cttaactaca      660
atatccgtta aggacgttta cgggtcgttt ggtacatgag ataaaaataa taattttggg      720
ataaagtttg ggattaaatt tatctcatgt ttcatttgga atattagcta atcttgggat      780
taacttttac actaaaattg tgggattagt tatccaatat agaaggcggg ataactaatc      840
gcatgagata ttccacccca taggatattc tcggatatcc caccattata ccaaacgatc      900
cataagagaa aaataaataa caacttataa ttactttat aattaaagtc attcaatatc       960
tttaagggtc tgtttggaaa gccttgtgta attacttggt tgtgtaatta ctaggatagt     1020
aattacacag cctggtaatt acgtagtatt gtaattacaa tggcttgttt gtttgtcatg     1080
gtgtaattac agtgtaatta catgtgtcat gtttggttgt acaagtgtaa ttatataaat     1140
aaataaatat ttttactgt atgataaata tttatatgta taatagatat taaatactat      1200
tatatattga ataaaaaaaa aggaattgga aaggttgcct caccaaattc tttaccgcct     1260
tttgagaatt ggagagtgta attaccctct cccaattaca ctcaattcat caccaatcaa     1320
ataattactt ggttaaataa atatgccaaa gtgtataatt acacccaatt cacttaatt     1380 tcaatttcca tgtggctttc caaacaggct ctaaggggta gcaacgtctt tgcccttctt     1440 tcttttatt ttttcccgaa gcttttcatt tccctctaat tatgacgaaa gatcattgtt      1500
ttaatttgta ctgtgaatat aaacatttca gcaacttccc caactggttc tccggaaatc     1560
tctccgtcca ttccttcagg tacgaatacg aacaaatcgt gcactgtaac aactgcactt     1620
tttccatgtt ttttttcctg caccaattc aacatttata taatgggtgt gagaattata      1680
tacttgtgag cgcaggagac agatattcaa gattttcgcc aaatggagat tcattgaagc     1740
tgcagccata ctctctgtta tttaccctta atgtagccac tttgtcatat gtcacaatat     1800
tcagctccat cttataa                                                   1817
```

<210> SEQ ID NO 68
<211> LENGTH: 336
<212> TYPE: DNA
<213> ORGANISM: Nicotiana tabacum

<400> SEQUENCE: 68

```
atggcaaaaa tccttatagc tttgtttgct ttgtctctaa ttttaggcca aacaaatgca       60
gatattcagt gtagtgatgt tatatcaaaa gtgagctctt gtgaagggta tttgctaggt      120
aaagttgcag cacctagccc aaattgttgc tttggattgc aagatttggc taaagtggct      180
gatgactcac aaccagatcg tcaaactatt tgtcaatgct taaagctgc catgcaaact       240 ttccctgtgg acttccaaaa agctaaacaa cttcctcaga tttgccattt caagagtact      300
ataccaattg aacccaatgt tgattgctca agtaa                                 336
```

<210> SEQ ID NO 69
<211> LENGTH: 354
<212> TYPE: DNA
<213> ORGANISM: Nicotiana tabacum

<400> SEQUENCE: 69

```
atggctaaag tagcattgtt ggtggtggtg tgcatggcag cagtagctgt gatgctaacg       60
```

```
ccccatgcag acgctgacat ctcttgtggg caggttgttg cgagcttgtc accatgcatt      120
agctatgtga ggcaaggtgg tgctattcca gcaccatgct gcagtggaat taattccctc      180
aacaaccaag ctaccagcac tcctgatcga cagacggctt gtaactgtat aaatctgct       240 gctgcaggca tcagtggcat caacttcagt cttgctggta gtcttcctag caaatgtggt      300
gtcaatcttc cctataagat tagcccttcc attgactgct ccacggtgca gtaa            354

<210> SEQ ID NO 70
<211> LENGTH: 345
<212> TYPE: DNA
<213> ORGANISM: Nicotiana tabacum

<400> SEQUENCE: 70
atggaaatgg taggtaagat tgcatgcttt gtggttttgt gcatggtggt ggttgcaccc      60
catgcagagg cactgagctg cggccaagtt cagtccggct tggctccttg tctcccttat     120
ttgcagggcc gcggccctt t ggggagctgt tgtggtggtg ttaaaggtct gttgggtgca    180
gccaagtccc catctgaccg aagactgca tgcacttgcc tgaaatcggc tgctaatgct      240
attaagggta ttgatatggg caaagccgct ggtctccctg gtgcttgtgg tgtcaacatt     300
ccttacaaga tcagcccctc cacagactgc tctaaggtcc agtaa                     345

<210> SEQ ID NO 71
<211> LENGTH: 294
<212> TYPE: DNA
<213> ORGANISM: Nicotiana tabacum

<400> SEQUENCE: 71
atgaagaagg gtggtaattc ttttgcggca ataatcttgg ttgtgacact agtccttttt      60
cttggcgaat ttctagtgac agaggcagta acgtgcagtg tcgtggagct gagtccgtgt     120
gccggggcga tctcgtcgcc acagccaccc tcttcggcat gttgcgctaa gttgaaagag     180
cagaagcctt gtctttgtgg gtacctcaaa aatccaaacc taaggcctta tgtcaattct     240
cctaatgcca agagagttgc taaatcctgt ggagtaccca ctcccagctg ttag           294

<210> SEQ ID NO 72
<211> LENGTH: 117
<212> TYPE: PRT
<213> ORGANISM: Nicotiana tabacum

<400> SEQUENCE: 72

Met Ala Arg Leu Phe Tyr Thr Met Ile Ile Leu Leu Ala Leu Ala
1               5                   10                  15

Thr Ser Ala Ile Ala Glu Pro Ser Cys Lys Thr Val Ala Lys Gly Ile
            20                  25                  30

Val Pro Cys Val Ser Tyr Ile Arg Gly Lys His Lys Ser Asp Lys
        35                  40                  45

Pro Ser Asn Met Cys Cys Lys Gly Leu Asn Asp Ile Ala Asn Val Ile
    50                  55                  60

Lys Asn Gly Lys Asp Arg Val Ala Val Cys Lys Cys Ile Lys Met Ala
65                  70                  75                  80

Leu Ser Arg Ile His Tyr Asp Pro Thr Arg Ile Thr Leu Ala Ser Gln
                85                  90                  95

Gln Cys His Thr Pro Ser Ser Leu Pro Ser Val Gly Gln Asn Thr Asn
            100                 105                 110

Cys Ala Arg Ala Ile
        115
```

<210> SEQ ID NO 73
<211> LENGTH: 116
<212> TYPE: PRT
<213> ORGANISM: Nicotiana tabacum

<400> SEQUENCE: 73

Met Ala Arg Glu Lys Ser Val Met Cys Met Val Met Val Leu Gly Val
1               5                   10                  15

Ala Leu Ile Ile Gln Gly Thr Gly Ala Ala Glu Glu Cys Ser Thr Val
            20                  25                  30

Thr Ala Leu Val Ala Ala Cys Ser Ser Phe Val Asn Tyr Gly Thr Pro
        35                  40                  45

Asp Pro Thr Pro Gly Ala Pro Cys Cys Val Ala Met Thr Thr Leu Ser
    50                  55                  60

Asn Ile Ala Ser Ser Thr Glu Met Arg Gln Ala Val Cys Arg Cys Val
65                  70                  75                  80

Met Asp Leu Ile Thr Thr Tyr Asn Pro Asn Ala Thr Ala Ile Ala Thr
                85                  90                  95

Leu Pro Gly Phe Cys Gly Val Ser Leu Gly Phe Thr Ile Asp Pro Asn
            100                 105                 110

Thr Asp Cys Glu
        115

<210> SEQ ID NO 74
<211> LENGTH: 153
<212> TYPE: PRT
<213> ORGANISM: Nicotiana tabacum

<400> SEQUENCE: 74

Met Ala Arg Glu Lys Ser Val Met Cys Met Val Met Val Leu Gly Val
1               5                   10                  15

Ala Ile Ile Ile Gln Gly Thr Gly Ala Ala Glu Glu Cys Ser Thr Val
            20                  25                  30

Thr Ala Leu Val Ala Ala Cys Ser Ser Phe Val Asn Tyr Gly Thr Pro
        35                  40                  45

Asp Pro Thr Pro Gly Ala Pro Cys Cys Val Ala Met Thr Thr Leu Ser
    50                  55                  60

Asn Ile Ala Ser Ser Thr Glu Met Arg Gln Ala Val Cys Arg Cys Val
65                  70                  75                  80

Met Asp Leu Ile Thr Thr Tyr Asn Pro Asn Ala Thr Ala Ile Ala Thr
                85                  90                  95

Leu Pro Gly Phe Cys Gly Val Ser Leu Gly Phe Thr Ile Asp Pro Asn
            100                 105                 110

Thr Asp Ser Ile Arg Tyr Ser Arg Ser Thr Gly Pro Ile Asn Arg Asp
        115                 120                 125

Leu Leu Trp Leu Lys Lys Phe Ser Thr Pro Gly Cys Leu Ile Thr Ile
    130                 135                 140

Trp Ser Leu Glu Ser Asp Ala Glu Glu
145                 150

<210> SEQ ID NO 75
<211> LENGTH: 159
<212> TYPE: PRT
<213> ORGANISM: Nicotiana tabacum

<400> SEQUENCE: 75

```
Met Lys Met Leu Ala Ser Ala Ser Ser Ile Phe Val Ala Ile Val Leu
1               5                   10                  15

Leu Ser Leu His Val Ser Ala Gln Ser Asp Cys Gln Gln Val Ile Val
            20                  25                  30

Gly Leu Ala Pro Cys Leu Gln Tyr Ile Gln Gly Asn Ala Thr Thr Pro
        35                  40                  45

Ser Ser Gly Cys Cys Thr Gln Leu Ala Thr Ile Val Lys Asn Gln Pro
    50                  55                  60

Gln Cys Leu Cys Gln Val Val Asn Gly Gly Ser Asn Leu Gly Ile
65              70                  75                  80

Asn Val Asn Gln Thr Gln Thr Met Ala Leu Pro Lys Ala Cys Asn Val
                85                  90                  95

Gln Thr Pro Ser Ile Ser Leu Cys Lys Gly Thr Thr Pro Ser Gly Ser
            100                 105                 110

Pro Gly Ser Pro Ser Thr Pro Ser Gly Gly Ser Lys Gly Glu Pro Ser
            115                 120                 125

Gly Asn Ser Ser Gly Asn Ser Val Lys Met Pro Tyr Ser Leu Leu Phe
    130                 135                 140

Thr Leu Val Ala Ile Ala Phe Phe Ala Thr Val Phe Thr Thr Ile
145                 150                 155

<210> SEQ ID NO 76
<211> LENGTH: 164
<212> TYPE: PRT
<213> ORGANISM: Nicotiana tabacum

<400> SEQUENCE: 76

Met Gln Ile Ser Ala Ser Thr Ile Ser Ala Ile Ile Val Val Ala Val
1               5                   10                  15

Ala Leu Leu Ser Leu His Val Ile Ser Ala Gln Ser Asp Cys Glu Gln
            20                  25                  30

Val Val Val Gly Leu Ala Pro Cys Leu Gln Tyr Ile Glu Gly Asn Ala
        35                  40                  45

Thr Ser Pro Ser Ser Gly Cys Cys Thr Gln Leu Ala Thr Ile Val Lys
    50                  55                  60

Thr Gln Pro Gln Cys Leu Cys His Val Leu Asn Gly Glu Gly Ser Ser
65              70                  75                  80

Phe Gly Val Asn Ile Asn Gln Thr Leu Ala Leu Ala Leu Pro Thr Ala
                85                  90                  95

Cys Asn Ala His Thr Pro Phe Leu Thr Leu Cys Lys Ala Thr Ser Pro
            100                 105                 110

Thr Gly Ser Pro Glu Ile Ser Pro Ser Ile Pro Ser Gly Asp Arg Tyr
            115                 120                 125

Ser Arg Phe Ser Pro Asn Gly Asp Ser Leu Lys Leu Gln Pro Tyr Ser
    130                 135                 140

Leu Leu Phe Thr Leu Asn Val Ala Thr Leu Ser Tyr Val Thr Ile Phe
145                 150                 155                 160

Ser Ser Ile Leu

<210> SEQ ID NO 77
<211> LENGTH: 111
<212> TYPE: PRT
<213> ORGANISM: Nicotiana tabacum

<400> SEQUENCE: 77

Met Ala Lys Ile Leu Ile Ala Leu Phe Ala Leu Ser Leu Ile Leu Gly
```

```
            1               5                   10                  15
         Gln Thr Asn Ala Asp Ile Gln Cys Ser Asp Val Ile Ser Lys Val Ser
                        20                  25                  30

Ser Cys Glu Gly Tyr Leu Leu Gly Lys Val Ala Ala Pro Ser Pro Asn
                        35                  40                  45

Cys Cys Phe Gly Leu Gln Asp Leu Ala Lys Val Ala Asp Asp Ser Gln
                        50                  55                  60

Pro Asp Arg Gln Thr Ile Cys Gln Cys Phe Lys Ala Ala Met Gln Thr
         65                     70                  75                  80

Phe Pro Val Asp Phe Gln Lys Ala Lys Gln Leu Pro Gln Ile Cys His
                             85                  90                  95

Phe Lys Ser Thr Ile Pro Ile Glu Pro Asn Val Asp Cys Ser Lys
                             100                 105                 110

<210> SEQ ID NO 78
<211> LENGTH: 117
<212> TYPE: PRT
<213> ORGANISM: Nicotiana tabacum

<400> SEQUENCE: 78

Met Ala Lys Val Ala Leu Leu Val Val Val Cys Met Ala Ala Val Ala
         1               5                   10                  15

Val Met Leu Thr Pro His Ala Asp Ala Asp Ile Ser Cys Gly Gln Val
                        20                  25                  30

Val Ala Ser Leu Ser Pro Cys Ile Ser Tyr Val Arg Gln Gly Gly Ala
                        35                  40                  45

Ile Pro Ala Pro Cys Cys Ser Gly Ile Asn Ser Leu Asn Asn Gln Ala
                        50                  55                  60

Thr Ser Thr Pro Asp Arg Gln Thr Ala Cys Asn Cys Ile Lys Ser Ala
         65                     70                  75                  80

Ala Ala Gly Ile Ser Gly Ile Asn Phe Ser Leu Ala Gly Ser Leu Pro
                             85                  90                  95

Ser Lys Cys Gly Val Asn Leu Pro Tyr Lys Ile Ser Pro Ser Ile Asp
                             100                 105                 110

Cys Ser Thr Val Gln
                     115

<210> SEQ ID NO 79
<211> LENGTH: 114
<212> TYPE: PRT
<213> ORGANISM: Nicotiana tabacum

<400> SEQUENCE: 79

Met Glu Met Val Gly Lys Ile Ala Cys Phe Val Val Leu Cys Met Val
         1               5                   10                  15

Val Val Ala Pro His Ala Glu Ala Leu Ser Cys Gly Gln Val Gln Ser
                        20                  25                  30

Gly Leu Ala Pro Cys Leu Pro Tyr Leu Gln Gly Arg Gly Pro Leu Gly
                        35                  40                  45

Ser Cys Cys Gly Gly Val Lys Gly Leu Leu Gly Ala Ala Lys Ser Pro
                        50                  55                  60

Ser Asp Arg Lys Thr Ala Cys Thr Cys Leu Lys Ser Ala Ala Asn Ala
         65                     70                  75                  80

Ile Lys Gly Ile Asp Met Gly Lys Ala Ala Gly Leu Pro Gly Ala Cys
                             85                  90                  95

Gly Val Asn Ile Pro Tyr Lys Ile Ser Pro Ser Thr Asp Cys Ser Lys
```

```
                    100                 105                 110

Val Gln

<210> SEQ ID NO 80
<211> LENGTH: 97
<212> TYPE: PRT
<213> ORGANISM: Nicotiana tabacum

<400> SEQUENCE: 80

Met Lys Lys Gly Gly Asn Ser Phe Ala Ala Ile Ile Leu Val Val Thr
1               5                   10                  15

Leu Val Leu Phe Leu Gly Glu Phe Leu Val Thr Glu Ala Val Thr Cys
            20                  25                  30

Ser Val Val Glu Leu Ser Pro Cys Ala Gly Ala Ile Ser Ser Pro Gln
        35                  40                  45

Pro Pro Ser Ser Ala Cys Cys Ala Lys Leu Lys Glu Gln Lys Pro Cys
    50                  55                  60

Leu Cys Gly Tyr Leu Lys Asn Pro Asn Leu Arg Pro Tyr Val Asn Ser
65                  70                  75                  80

Pro Asn Ala Lys Arg Val Ala Lys Ser Cys Gly Val Pro Thr Pro Ser
                85                  90                  95

Cys

<210> SEQ ID NO 81
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ser Asn Asn Ser Leu Ser Ile Lys Asn Pro Lys Val Ser Leu Ala
1               5                   10                  15

Phe Val Met Leu Pro Lys Ala Asn Met Trp Lys Glu Thr Lys Leu Lys
            20                  25                  30

Ile Ser Ile Met Leu Asn Lys Gln Leu Phe Met Ala Lys Asn Ile Met
        35                  40                  45

Lys Glu Met Val Gly Ser Ile Ala Cys Leu Leu Val Leu Cys Met Val
    50                  55                  60

Val Ala Ala Pro His Ala Ala Pro Ile Gln Arg His Ala Ala Ile
65                  70                  75                  80

Thr Cys Gly Gln Val Asp Ala Ser Leu Ala Pro Cys Leu Pro Tyr Leu
                85                  90                  95

Thr Gly Gly Gly Ala Pro Thr Arg Gly Pro Ser Ala Ala Cys Cys Ser
                100                 105                 110

Gly Val Lys Ser Leu Leu Gly Ala Ala Lys Thr Thr Ala Pro Asp Leu
                115                 120                 125

Asp Arg Gln Ala Ala Cys Asn Cys Leu Lys Ser Ala Ala Asn Arg Ile
    130                 135                 140

Phe Thr Gly Ile Asn Asp Ala Ala Ala Leu Pro Ser Lys Cys
145                 150                 155                 160

Gly Val Asn Tyr Leu Pro Phe Lys Ile Ser Pro Ser Thr Glu Pro Val
                165                 170                 175

Asp Cys Ser Lys Ile Gln Met Ser Thr Pro Ser Gly Asp Arg Asp Gly
                180                 185                 190
```

```
Leu Phe Ser Tyr Lys Phe Ser Gly Asp Ser Cys Lys Ile Gln Pro Tyr
            195                 200                 205

Ser Leu Leu Phe Thr Leu Glu Val Ala His Ala Phe Phe Ala Thr Ile
    210                 215                 220

Phe Pro Ser Ile Leu
225

<210> SEQ ID NO 82
<211> LENGTH: 88
<212> TYPE: PRT
<213> ORGANISM: Nicotiana tabacum

<400> SEQUENCE: 82

Ser Ala Ile Ala Glu Pro Ser Cys Lys Thr Val Ala Lys Gly Ile Val
1               5                   10                  15

Pro Cys Val Ser Tyr Ile Arg Gly Lys His His Lys Ser Asp Lys Pro
            20                  25                  30

Ser Asn Met Cys Cys Lys Gly Leu Asn Asp Ile Ala Asn Val Ile Lys
        35                  40                  45

Asn Gly Lys Asp Arg Val Ala Val Cys Lys Cys Ile Lys Met Ala Leu
    50                  55                  60

Ser Arg Ile His Tyr Asp Pro Thr Arg Ile Thr Leu Ala Ser Gln Gln
65                  70                  75                  80

Cys His Thr Pro Ser Ser Leu Pro
                85

<210> SEQ ID NO 83
<211> LENGTH: 91
<212> TYPE: PRT
<213> ORGANISM: Nicotiana tabacum

<400> SEQUENCE: 83

Ala Leu Ile Ile Gln Gly Thr Gly Ala Ala Glu Glu Cys Ser Thr Val
1               5                   10                  15

Thr Ala Leu Val Ala Ala Cys Ser Ser Phe Val Asn Tyr Gly Thr Pro
            20                  25                  30

Asp Pro Thr Pro Gly Ala Pro Cys Cys Val Ala Met Thr Thr Leu Ser
        35                  40                  45

Asn Ile Ala Ser Ser Thr Glu Met Arg Gln Ala Val Cys Arg Cys Val
    50                  55                  60

Met Asp Leu Ile Thr Thr Tyr Asn Pro Asn Ala Thr Ala Ile Ala Thr
65                  70                  75                  80

Leu Pro Gly Phe Cys Gly Val Ser Leu Gly Phe
                85                  90

<210> SEQ ID NO 84
<211> LENGTH: 91
<212> TYPE: PRT
<213> ORGANISM: Nicotiana tabacum

<400> SEQUENCE: 84

Ala Ile Ile Ile Gln Gly Thr Gly Ala Ala Glu Glu Cys Ser Thr Val
1               5                   10                  15

Thr Ala Leu Val Ala Ala Cys Ser Ser Phe Val Asn Tyr Gly Thr Pro
            20                  25                  30

Asp Pro Thr Pro Gly Ala Pro Cys Cys Val Ala Met Thr Thr Leu Ser
        35                  40                  45

Asn Ile Ala Ser Ser Thr Glu Met Arg Gln Ala Val Cys Arg Cys Val
```

```
                50                  55                  60

Met Asp Leu Ile Thr Thr Tyr Asn Pro Asn Ala Thr Ala Ile Ala Thr
 65                  70                  75                  80

Leu Pro Gly Phe Cys Gly Val Ser Leu Gly Phe
                 85                  90

<210> SEQ ID NO 85
<211> LENGTH: 86
<212> TYPE: PRT
<213> ORGANISM: Nicotiana tabacum

<400> SEQUENCE: 85

Leu Leu Ser Leu His Val Ser Ala Gln Ser Asp Cys Gln Gln Val Ile
 1               5                  10                  15

Val Gly Leu Ala Pro Cys Leu Gln Tyr Ile Gln Gly Asn Ala Thr Thr
                20                  25                  30

Pro Ser Ser Gly Cys Cys Thr Gln Leu Ala Thr Ile Val Lys Asn Gln
            35                  40                  45

Pro Gln Cys Leu Cys Gln Val Val Asn Gly Gly Ser Asn Leu Gly
        50                  55                  60

Ile Asn Val Asn Gln Thr Gln Thr Met Ala Leu Pro Lys Ala Cys Asn
 65                  70                  75                  80

Val Gln Thr Pro Ser Ile
                 85

<210> SEQ ID NO 86
<211> LENGTH: 87
<212> TYPE: PRT
<213> ORGANISM: Nicotiana tabacum

<400> SEQUENCE: 86

Leu Leu Ser Leu His Val Ile Ser Ala Gln Ser Asp Cys Glu Gln Val
 1               5                  10                  15

Val Val Gly Leu Ala Pro Cys Leu Gln Tyr Ile Glu Gly Asn Ala Thr
                20                  25                  30

Ser Pro Ser Ser Gly Cys Cys Thr Gln Leu Ala Thr Ile Val Lys Thr
            35                  40                  45

Gln Pro Gln Cys Leu Cys His Val Leu Asn Gly Glu Gly Ser Ser Phe
        50                  55                  60

Gly Val Asn Ile Asn Gln Thr Leu Ala Leu Ala Leu Pro Thr Ala Cys
 65                  70                  75                  80

Asn Ala His Thr Pro Phe Leu
                 85

<210> SEQ ID NO 87
<211> LENGTH: 87
<212> TYPE: PRT
<213> ORGANISM: Nicotiana tabacum

<400> SEQUENCE: 87

Leu Gly Gln Thr Asn Ala Asp Ile Gln Cys Ser Asp Val Ile Ser Lys
 1               5                  10                  15

Val Ser Ser Cys Glu Gly Tyr Leu Leu Gly Lys Val Ala Ala Pro Ser
                20                  25                  30

Pro Asn Cys Cys Phe Gly Leu Gln Asp Leu Ala Lys Val Ala Asp Asp
            35                  40                  45

Ser Gln Pro Asp Arg Gln Thr Ile Cys Gln Cys Phe Lys Ala Ala Met
        50                  55                  60
```

```
Gln Thr Phe Pro Val Asp Phe Gln Lys Ala Lys Gln Leu Pro Gln Ile
65                  70                  75                  80

Cys His Phe Lys Ser Thr Ile
                85
```

<210> SEQ ID NO 88
<211> LENGTH: 88
<212> TYPE: PRT
<213> ORGANISM: Nicotiana tabacum

<400> SEQUENCE: 88

```
Met Leu Thr Pro His Ala Asp Ala Asp Ile Ser Cys Gly Gln Val Val
1               5                   10                  15

Ala Ser Leu Ser Pro Cys Ile Ser Tyr Val Arg Gln Gly Gly Ala Ile
                20                  25                  30

Pro Ala Pro Cys Cys Ser Gly Ile Asn Ser Leu Asn Asn Gln Ala Thr
            35                  40                  45

Ser Thr Pro Asp Arg Gln Thr Ala Cys Asn Cys Ile Lys Ser Ala Ala
        50                  55                  60

Ala Gly Ile Ser Gly Ile Asn Phe Ser Leu Ala Gly Ser Leu Pro Ser
65                  70                  75                  80

Lys Cys Gly Val Asn Leu Pro Tyr
                85
```

<210> SEQ ID NO 89
<211> LENGTH: 86
<212> TYPE: PRT
<213> ORGANISM: Nicotiana tabacum

<400> SEQUENCE: 89

```
Val Val Ala Pro His Ala Glu Ala Leu Ser Cys Gly Gln Val Gln Ser
1               5                   10                  15

Gly Leu Ala Pro Cys Leu Pro Tyr Leu Gln Gly Arg Gly Pro Leu Gly
                20                  25                  30

Ser Cys Cys Gly Gly Val Lys Gly Leu Leu Gly Ala Ala Lys Ser Pro
            35                  40                  45

Ser Asp Arg Lys Thr Ala Cys Thr Cys Leu Lys Ser Ala Ala Asn Ala
        50                  55                  60

Ile Lys Gly Ile Asp Met Gly Lys Ala Ala Gly Leu Pro Gly Ala Cys
65                  70                  75                  80

Gly Val Asn Ile Pro Tyr
                85
```

<210> SEQ ID NO 90
<211> LENGTH: 78
<212> TYPE: PRT
<213> ORGANISM: Nicotiana tabacum

<400> SEQUENCE: 90

```
Val Leu Phe Leu Gly Glu Phe Leu Val Thr Glu Ala Val Thr Cys Ser
1               5                   10                  15

Val Val Glu Leu Ser Pro Cys Ala Gly Ala Ile Ser Ser Pro Gln Pro
                20                  25                  30

Pro Ser Ser Ala Cys Cys Ala Lys Leu Lys Glu Gln Lys Pro Cys Leu
            35                  40                  45

Cys Gly Tyr Leu Lys Asn Pro Asn Leu Arg Pro Tyr Val Asn Ser Pro
        50                  55                  60
```

```
Asn Ala Lys Arg Val Ala Lys Ser Cys Gly Val Pro Thr Pro
 65                  70                  75
```

<210> SEQ ID NO 91
<211> LENGTH: 86
<212> TYPE: PRT
<213> ORGANISM: Nicotiana tabacum

<400> SEQUENCE: 91

```
Val Val Ala Pro His Ala Glu Ala Leu Thr Cys Gly Gln Val Gln Ser
  1               5                  10                  15

Ser Leu Ala Pro Cys Val Pro Tyr Leu Leu Gly Arg Gly Pro Leu Gly
                 20                  25                  30

Gly Cys Cys Gly Gly Val Lys Arg Leu Leu Gly Ala Ala Arg Thr Pro
             35                  40                  45

Ala Asp Arg Lys Thr Ala Cys Asn Cys Leu Lys Ser Ala Ala Asn Thr
         50                  55                  60

Phe Lys Gly Ile Asp Met Gly Asn Ala Ala Arg Leu Pro Gly Thr Cys
 65                  70                  75                  80

Gly Val Asn Ile Pro Tyr
                 85
```

<210> SEQ ID NO 92
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Val Ala Ala Pro His Ala Ala Pro Ile Gln Arg His Ala Ala Ile
  1               5                  10                  15

Thr Cys Gly Gln Val Asp Ala Ser Leu Ala Pro Cys Leu Pro Tyr Leu
                 20                  25                  30

Thr Gly Gly Gly Ala Pro Thr Arg Gly Pro Ser Ala Ala Cys Cys Ser
             35                  40                  45

Gly Val Lys Ser Leu Leu Gly Ala Ala Lys Thr Thr Ala Pro Asp Leu
         50                  55                  60

Asp Arg Gln Ala Ala Cys Asn Cys Leu Lys Ser Ala Ala Asn Arg Ile
 65                  70                  75                  80

Phe Thr Gly Ile Asn Asp Asp Ala Ala Ala Leu Pro Ser Lys Cys
                 85                  90                  95

Gly Val Asn Tyr Leu Pro Phe
                100
```

<210> SEQ ID NO 93
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(48)
<223> OTHER INFORMATION: This region may be absent

<400> SEQUENCE: 93

```
Met Ser Asn Asn Ser Leu Ser Ile Lys Asn Pro Lys Val Ser Leu Ala
  1               5                  10                  15
```

```
Phe Val His Asn Thr Gln Gly Asn Asn Ile Cys Ser Thr Ile Pro Leu
            20              25              30

Tyr Phe Val Gln Thr Thr Leu Tyr Cys Ser Leu Ile Phe Leu Leu Arg
        35              40              45

Met Glu Met Val Ser Lys Ile Ala Cys Phe Val Val Leu Cys Met Val
    50              55              60

Val Val Ala Pro His Ala Glu Ala Leu Thr Cys Gly Gln Val Gln Ser
65              70              75              80

Ser Leu Ala Pro Cys Val Pro Tyr Leu Leu Gly Arg Gly Pro Leu Gly
            85              90              95

Gly Cys Cys Gly Gly Val Lys Arg Leu Leu Gly Ala Ala Arg Thr Pro
            100             105             110

Ala Asp Arg Lys Thr Ala Cys Asn Cys Leu Lys Ser Ala Ala Asn Thr
        115             120             125

Phe Lys Gly Ile Asp Met Gly Asn Ala Ala Arg Leu Pro Gly Thr Cys
        130             135             140

Gly Val Asn Ile Pro Tyr Lys Ile Ser Pro Ser Thr Asp Cys Ser Lys
145             150             155             160

Val Gln
```